(12) United States Patent
Everard et al.

(10) Patent No.: US 11,390,876 B2
(45) Date of Patent: Jul. 19, 2022

(54) COMPOSITIONS AND METHODS FOR MODIFICATION OF FATTY ACIDS IN SOYBEAN

(71) Applicant: PIONEER HI-BRED INTERNATIONAL, INC., Johnston, IA (US)

(72) Inventors: John D Everard, Grimes, IA (US); Anthony J Kinney, Wilmington, DE (US); Zhan-Bin Liu, Clive, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/977,608

(22) PCT Filed: Mar. 1, 2019

(86) PCT No.: PCT/US2019/020207
§ 371 (c)(1),
(2) Date: Sep. 2, 2020

(87) PCT Pub. No.: WO2019/173125
PCT Pub. Date: Sep. 12, 2019

(65) Prior Publication Data
US 2020/0399648 A1     Dec. 24, 2020

Related U.S. Application Data

(60) Provisional application No. 62/753,718, filed on Oct. 31, 2018, provisional application No. 62/721,331, filed on Aug. 22, 2018, provisional application No. 62/640,682, filed on Mar. 9, 2018.

(51) Int. Cl.
*C12N 15/82* (2006.01)
*C12Q 1/6895* (2018.01)

(52) U.S. Cl.
CPC ..... *C12N 15/8247* (2013.01); *C12N 15/8213* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2014/0090116 A1\* 3/2014 Ainley ............... C12N 15/102
800/312

FOREIGN PATENT DOCUMENTS

| WO | 2014039684 A1 | 3/2014 |
| WO | 2014039692 A2 | 3/2014 |
| WO | 2014039702 A2 | 3/2014 |
| WO | 2014039872 A1 | 3/2014 |
| WO | 2015026886 A1 | 2/2015 |
| WO | 2017134601 A1 | 8/2017 |

OTHER PUBLICATIONS

Demorest et al 2016 (BMC Plant Biology 16:225, p. 1-8) (Year: 2016).\*
Pham et al 2012 (Theor Appl Genet 125: p. 503-515) (Year: 2012).\*
Xing et al 2014 (BMC Plant Biology 14:327 p. 1-12) (Year: 2014).\*
Cai et al 2015 (PLOS One 10:8 p. 1-13) (Year: 2015).\*
International Search Report and Written Opinion dated Apr. 24, 2019 for PCT/US2019/020207.
Pham, et al.; "Combinations of mutant FAD2 and FAD3 genes to produce high oleic acid and low linolenic acid soybean oil"; Theoretical and Applied Genetics—International Journal of Plant Breeding (2012) 125(3):503-515 Springer; Berlin DE.
Demorest, et al.; "Direct stacking of sequence-specific nuclease-induced mutations to produce high oleic and low inolenic soybean oil"; BMC Plant Biology (2016) 16(1):10 DOI: 10.1186/s12870-016-0906-1.

\* cited by examiner

*Primary Examiner* — Matthew R Keogh

(57) ABSTRACT

Methods and compositions to modify the fatty acid profiles of seeds and the oils produced therefrom include the modification of four or more alleles of fatty acid desaturases in the genome of a plant. Compositions, polynucleotide constructs, transformed and modified host cells, and plants and seeds exhibiting altered fatty characteristics are provided.

12 Claims, 9 Drawing Sheets
Specification includes a Sequence Listing.

1.1 GTGGAAGTTCAAGGGAAGAAGC------------GTTCCAAACACAAAGCCACCATTCACTGT SEQ ID NO. 36 11bp deletion
1.2 GTGGAAGTTCAAGGGAAGAAGCCCTCTC--------TTCCAAACACAAAGCCACCATTCACTGT SEQ ID NO. 37 7bp deletion
1.3 GTGGAAGTTCAAGGGAAGAAGCCCTCTC-------TCCAAACACAAAGCCACCATTCACTGT SEQ ID NO. 38 8bp deletion
6.1 GTGGAAGTTCAAGGGAAGAAGCCCTCTC-----GGTTCCAAACACAAAGCCACCATTCACTGT SEQ ID NO. 39 5bp deletion
1.4 GTGGAAGTTCAAGGGAAGAAGCCCTCTC-------TTCCAAACACAAAGCCACCATTCACTGT SEQ ID NO. 40 7bp deletion
1.5 GTGGAAGTTCAAGGGAAGAAGCCCTCTCT----GGTTCCAAACACAAAGCCACCATTCACTGT SEQ ID NO. 41 4bp deletion
1.6 GTGGAAGTTCAAGGGAAGAAGCCCTCTCT-AAGGGTTCCAAACACAAAGCCACCATTCACTGT SEQ ID NO. 42 1bp deletion
1.7 GTGGAAGTTCAAGGGAAG--------------------------AAAGCCACCATTCACTGT SEQ ID NO. 43 26bp deletion

FIG. 1A

| | | |
|---|---|---|
| WT | GTTGAAATTCAGCAGAAGAAGCCTCTCTCAAGGGTTCCAAACACAAAGCCACCATTCACTGT | SEQ ID NO. 44 |
| 1.1 | GTTGAAATTCAGCAGAAGAAGCCTCTC----GGGTTCCAAACACAAAGCCACCATTCACTGT | SEQ ID NO. 45  4bp deletion |
| 1.2 | GTTGAAATTCAGCAGAAGAAGCCTCT-----------CAAACACAAAGCCACCATTCACTGT | SEQ ID NO. 46  11bp deletion |
| 1.3 | GTTGAAATTCAGCAGAAGAAGCCTC----------------CACAAAGCCACCATTCACTGT | SEQ ID NO. 47  16bp deletion |
| 6.1 | GTTGAAATTCAGCAGAAGAAGCCTCT-----------CAAACACAAAGCCACCATTCACTGT | SEQ ID NO. 48  11bp deletion |
| 1.4 | GTTGAAATTCAGCAGAAGAAGCCTCTCTTCAAGGGTTCCAAACACAAAGCCACCATTCACTGT | SEQ ID NO. 49  1bp Insertion |
| 1.5 | GTTGAAATTCAGCAGAAGAAGCCTCTC-------TTCCAAACACAAAGCCACCATTCACTGT | SEQ ID NO. 50  7bp deletion |
| 1.6 | GTTGAAATTCAGCAGAAGAAGCCTCTC--------TCCAAACACAAAGCCACCATTCACTGT | SEQ ID NO. 51  8bp deletion |
| 1.7 | GTTGAAATTCAGCAGAAGAAGCCTCTC--------TCCAAACACAAAGCCACCATTCACTGT | SEQ ID NO. 52  8bp deletion |

FIG. 1B

Edited FAD2-1A Gene
WT   GTGGAAGTTCAAGGGAAGAAGCCTCTCTCAAGGGTTCCAAACACAAAGCCACCATTCACTGT    SEQ ID NO. 53
3.1  GTGGAAGTTCAAGGGAAGAAGCCTCTC------TTCCAAACACAAAGCCACCATTCACTGT    SEQ ID NO. 54 7bp deletion
5.3  GTGGAAGTTCAAGGGAAGAAGCC------AGGGTTCCAAACACAAAGCCACCATTCACTGT    SEQ ID NO. 55 7bp deletion
1.5a GTGGAAGTTCAAGGGAAGAAGCCT-------------CAAACACAAAGCCACCATTCACTGT   SEQ ID NO. 77 13bp deletion Edited FAD2-1B Gene
WT   GTTGAAATTCAGCAGAAGAAGCCTCTCTCAAGGGTTCCAAACACAAAGCCACCATTCACTGT   SEQ ID NO. 56
3.1  GTTGAAATTCAGCAGAAGAAGCCTCTC-----GGTTCCAAACACAAAGCCACCATTCACTGT   SEQ ID NO. 57 5bp deletion
5.3  GTTGAAATTCAGCAGAAGAAGCCTCTC-------TTCCAAACACAAAGCCACCATTCACTGT   SEQ ID NO. 58 7bp deletion
1.5a GTTGAAATTCAGCAGAAGAAGCCTCTC-----GGTTCCAAACACAAAGCCACCATTCACTGT   SEQ ID NO. 57 5bp deletion Edited FAD3a Gene
WT   GCTGGGTCAAGAATCCATGGAGATCCCTCAGTTATGTTCTCAGGGATGTGCTTGTAATTGCT   SEQ ID NO. 59
3.1  GCTGGGTCAAGAATCCATGG--ATCCCTCAGTTATGTTCTCAGGGATGTGCTTGTAATTGCT   SEQ ID NO. 60 2bp deletion
5.3  GCTGGGTCAAGAATCCATGG----CCCTCAGTTATGTTCTCAGGGATGTGCTTGTAATTGCT   SEQ ID NO. 61 4bp deletion
1.5a GCTGGGTCAAGAATCCATGGA----CCTCAGTTATGTTCTCAGGGATGTGCTTGTAATTGCT   SEQ ID NO. 78 4bp deletion Edited FAD3b Gene
WT   GCTGGGTCAAGAATCCATGGAGATCCCTCAGTTATGTTCTCAGGGATGTGCTTGTAATTGCT   SEQ ID NO. 62
3.1  GCTGGGTCAAGAATCCATGG--ATCCCTCAGTTATGTTCTCAGTGTTCTCAGGGATGTGCTTGTAATTGCT   SEQ ID NO. 63 2bp deletion
5.3  GCTGGGTCAAGAATCCATGG--ATCCCTCAGTTATGTTCTCAGGGATGTGCTTGTAATTGCT   SEQ ID NO. 64 2bp deletion
1.5a GCTGGGTCAAGAATCCATGGA--TCCCTCAGTTATGTTCTCAGGGATGTGCTTGTAATTGCT   SEQ ID NO. 79 2bp deletion

FIG. 2

| | | |
|---|---|---|
| WT | GTGGAAGTTCAAGGGAAGAAGCCTCTCTCAAGGGTTCCAAACACAAAGCCACCATTCACTGT | SEQ ID NO: 83 |
| 1.1 | GTGGAAGTTCAAGGGAAGAAGCCTCTC-------TTCCAAACACAAAGCCACCATTCACTGT | SEQ ID NO: 84 7bp deletion |
| 1.2 | GTGGAAGTTCAAGGGAAGAAGCCTCTCT--AGGGTTCCAAACACAAAGCCACCATTCACTGT | SEQ ID NO: 85 2bp deletion |
| 1.3 | GTGGAAGTTCAAGGGAAGAAGCCTCTCT-----GTTCCAAACACAAAGCCACCATTCACTGT | SEQ ID NO: 86 5bp deletion |
| 1.4 | GTGGAAGTTCAAGGGAAGAAGCCTCT-----------CAAACACAAAGCCACCATTCACTGT | SEQ ID NO: 87 11bp deletion |
| 1.5 | GTGGAAGTTCAAGGGAAGAAGCCTC--------GTTCCAAACACAAAGCCACCATTCACTGT | SEQ ID NO: 88 8bp deletion |
| 1.6 | GTGGAAGTTCAAGGGAAGAAGCCTCTCT----GGTTCCAAACACAAAGCCACCATTCACTGT | SEQ ID NO: 89 4bp deletion |
| 1.7 | GTGGAAGTTCAAGGGAAGAAGCCTCTC--------TCCAAACACAAAGCCACCATTCACTGT | SEQ ID NO: 90 8bp deletion |
| 1.8 | GTGGAAGTTCAAGGGAAGAAGCCTCT-------GTTCCAAACACAAAGCCACCATTCACTGT | SEQ ID NO: 91 7bp deletion |

FIG. 3A

| | | | |
|---|---|---|---|
| WT | GTTGAAATTCAGCAGAAGAAGCCTCTCTCAAGGGTTCCAAACACAAAGCCACCATTCACTGT | SEQ ID NO: 92 | |
| 1.1 | GTTGAAATTCAGCAGAAGAAGCCTCTC-------TTCCAAACACAAAGCCACCATTCACTGT | SEQ ID NO: 93 | 7bp deletion |
| 1.2 | GTTGAAATTCAGCAGAAGAAGCC----------------AACACAAAGCCACCATTCACTGT | SEQ ID NO: 94 | 16bp deletion |
| 1.3 | GTTGAAATTCAGCAGAAGAAGCCTCTCT-----GTTCCAAACACAAAGCCACCATTCACTGT | SEQ ID NO: 95 | 5bp deletion |
| 1.4 | GTTGAAATTCAGCAGAAGAAGCCTCTCT----GGTTCCAAACACAAAGCCACCATTCACTGT | SEQ ID NO: 96 | 4bp deletion |
| 1.5 | GTTGAAATTCAGCAGAAGAAGCCTCTC-----GGTTCCAAACACAAAGCCACCATTCACTGT | SEQ ID NO: 97 | 5bp deletion |
| 1.6 | GTTGAAATTCAGCAGAAGAAGCCTCT--------TTCCAAACACAAAGCCACCATTCACTGT | SEQ ID NO: 98 | 8bp deletion |
| 1.7 | GTTGAAATTCAGCAGAAGAAGCCTCT---CAAGGGTTCCAAACACAAAGCCACCATTCACTGT | SEQ ID NO: 99 | 2bp deletion |
| 1.8 | GTTGAAATTCAGCAGAAGAAGCC-------AGGGTTCCAAACACAAAGCCACCATTCACTGT | SEQ ID NO: 100 | 7bp deletion |

FIG. 3B

| | | | |
|---|---|---|---|
| WT | GTGGAAGTTCAAGGGAAGAAGCCTCTCTCAAGGGTTCCAAACACAAAGCCACCATTCACTGT | SEQ ID NO: | 101 |
| 1.1 | GTGGAAGTTCAAGGGAAGAAGCCTCTCT--AGGGTTCCAAACACAAAGCCACCATTCACTGT | SEQ ID NO: | 102 2bp deletion |
| 1.2 | GTGGAAGTTCAAGGGAAGAAGCCTCTC--------TCCAAACACAAAGCCACCATTCACTGT | SEQ ID NO: | 103 8bp deletion |
| 1.3 | GTGGAAGTTCAAGGGAAGAAGCCTCTCT-----GTTCCAAACACAAAGCCACCATTCACTGT | SEQ ID NO: | 104 5bp deletion |
| 1.4 | GTGGAAGTTCAAGGGAAGAAGCCTCTC-------TTCCAAACACAAAGCCACCATTCACTGT | SEQ ID NO: | 105 7bp deletion |
| 1.5 | GTGGAAGTTCAAGGGAAGAAGCCT-------GGTTCCAAACACAAAGCCACCATTCACTGT | SEQ ID NO: | 106 7bp deletion |
| 1.6 | GTGGAAGTTCAAGGGAAGAAGCCTCTC-----GGTTCCAAACACAAAGCCACCATTCACTGT | SEQ ID NO: | 107 5bp deletion |
| 1.7 | GTGGAAGTTCAAGGGAAGAAGCCTCTCT--CAAGGGTTCCAAACACAAAGCCACCATTCACTGT | SEQ ID NO: | 108 2bp deletion |
| 1.8 | GTGGAAGTTCAAGGGAAGAAGCCTCTCT----------AAACACAAAGCCACCATTCACTGT | SEQ ID NO: | 109 10bp deletion |
| 1.9 | GTGGAAGTTCAAGGGAAGAAGCCTCTC----------CAAACACAAAGCCACCATTCACTGT | SEQ ID NO: | 136 10bp deletion |

FIG. 4A

| | Sequence | SEQ ID NO | Mutation |
|---|---|---|---|
| WT | GTTGAAATTCAGCAGAAGAAGCCTCTCTCAAGGGTTCCAAACACAAAGCCACCATTCACTGT | SEQ ID NO: 110 | |
| 1.1 | GTTGAAATTCAGCAGAAGAAGCCTCTC-------TTCCAAACACAAAGCCACCATTCACTGT | SEQ ID NO: 111 | 7bp deletion |
| 1.2 | GTTGAAATTCAGCAGAAGAAGCCTCT--CAAGGGTTCCAAACACAAAGCCACCATTCACTGT | SEQ ID NO: 112 | 2bp deletion |
| 1.3 | GTTGAAATTCAGCAGAAGAAGCCTCT-----GTTCCAAACACAAAGCCACCATTCACTGT | SEQ ID NO: 113 | 5bp deletion |
| 1.4 | GTTGAAATTCAGCAGAAGAAGCCTCT----------CAAACACAAAGCCACCATTCACTGT | SEQ ID NO: 114 | 10bp deletion |
| 1.5 | GTTGAAATTCAGCAGAAGAAGCCTCTC--------TCCAAACACAAAGCCACCATTCACTGT | SEQ ID NO: 115 | 8bp deletion |
| 1.6 | GTTGAAATTCAGCAGAAGAA-------------GTTCCAAACACAAAGCCACCATTCACTGT | SEQ ID NO: 116 | 13bp deletion |
| 1.7 | GTTGAAATTCAGCAGAAGAAGC-----TCAAGGGTTCCAAACACAAAGCCACCATTCACTGT | SEQ ID NO: 117 | 5bp deletion |
| 1.8 | GTTGAAATTCAGCAGAAGAAGCCTCT----GGTTCCAAACACAAAGCCACCATTCACTGT | SEQ ID NO: 118 | 4bp deletion |
| 1.9 | GTTGAAATTCAGCAGAAGAAGCCT----------TTCCAAACACAAAGCCACCATTCACTGT | SEQ ID NO: 137 | 10bp deletion |
| 1.10 | GTTGAAATTCAGCAGAAGAAGCCTCTC----GGGTTCCAAACACAAAGCCACCATTCACTGT | SEQ ID NO: 138 | 4bp deletion |
| 1.11 | GTTGAAATTCAGCAGAAGAAGCCTCTCTTCAAGGGTTCCAAACACAAAGCCACCATTCACTGT | SEQ ID NO: 139 | 1bp insert |
| 1.12 | GTTGAAATTCAGCAGAAGAAGCCTCTC--------CAAACACAAAGCCACCATTCACTGT | SEQ ID NO: 140 | 8bp deletion |
| 1.13 | GTTGAAATTCAGCAGAAGAAGCCTCT-------GTTCCAAACACAAAGCCACCATTCACTGT | SEQ ID NO: 141 | 7bp deletion |
| 1.14 | GTTGAAATTCAGCAGAAGAAGCCT----------------------AGCCACCATTCACTGT | SEQ ID NO: 142 | 22bp deletion |

FIG. 4B

WT  GCTGGGTCAAGAATCCATGGAGATCCCTCAGTTATGTTCTCAGGGATGTGCTTGTAATTGCT  SEQ ID NO: 119
1.1 GCTGGGTCAAGAATCCATGG---ATCCCTCAGTTATGTTCTCAGGGATGTGCTTGTAATTGCT SEQ ID NO: 120 2bp deletion
1.2 GCTGGGTCAAGAATCCATGG-----CCCTCAGTTATGTTCTCAGGGATGTGCTTGTAATTGCT SEQ ID NO: 121 4bp deletion
1.3 GCTGGGTCAAGAATCCATGG------CCTCAGTTATGTTCTCAGGGATGTGCTTGTAATTGCT SEQ ID NO: 122 5bp deletion
1.4 GCTGGGTCAAGAATCCAT--------CCTCAGTTATGTTCTCAGGGATGTGCTTGTAATTGCT SEQ ID NO: 123 7bp deletion
1.5 GCTGGGTCAAGAATCCATGGA-----CCTCAGTTATGTTCTCAGGGATGTGCTTGTAATTGCT SEQ ID NO: 124 4bp deletion
1.6 GCTGGGTCAAGAATCCATGGA-ATCCCTCAGTTATGTTCTCAGGGATGTGCTTGTAATTGCT  SEQ ID NO: 125 1bp deletion
1.7 GCTGGGTCAAGAATCCATG---------TCAGTTATGTTCTCAGGGATGTGCTTGTAATTGCT SEQ ID NO: 143 8bp deletion
1.8 GCTGGGTCAAGAATCCATGG-GATCCCTCAGTTATGTTCTCAGGGATGTGCTTGTAATTGCT  SEQ ID NO: 144 1bp deletion
1.9 GCTGGGTCAAGAATCCATGGAAGATCCCTCAGTTATGTTCTCAGGGATGTGCTTGTAATTGCT SEQ ID NO: 145 1bp insert

FIG. 5A

| | | | |
|---|---|---|---|
| WT  | GCTGGGTCAAGAATCCATGGAGAGATCCCTCAGTTATGTTCTCAGGGATGTGCTTGTAATTGCT | SEQ ID NO: 126 | |
| 1.1 | GCTGGGTCAAGAATCCATGG--ATCCCTCAGTTATGTTCTCAGGGATGTGCTTGTAATTGCT | SEQ ID NO: 127 | 2bp deletion |
| 1.2 | GCTGGGTCAAGAATCCATGGA----CCCTCAGTTATGTTCTCAGGGATGTGCTTGTAATTGCT | SEQ ID NO: 128 | 4bp deletion |
| 1.3 | GCTGGGTCAAGAATCCATGGA-----------TATGTTCTCAGGGATGTGCTTGTAATTGCT | SEQ ID NO: 129 | 11bp deletion |
| 1.4 | GCTGGGTCAAGAATCCAT--AGATCCCTCAGTTATGTTCTCAGGGATGTGCTTGTAATTGCT | SEQ ID NO: 130 | 2bp deletion |
| 1.5 | GCTGGGTCAAGAATCCATGG----CCCTCAGTTATGTTCTCAGGGATGTGCTTGTAATTGCT | SEQ ID NO: 131 | 4bp deletion |
| 1.6 | GCTGGGTCAAGAATCCATGGA-------CAGTTATGTTCTCAGGGATGTGCTTGTAATTGCT | SEQ ID NO: 132 | 7bp deletion |
| 1.7 | GCTGGGTCAAGAATCCATGG-----CCTCAGTTATGTTCTCAGGGATGTGCTTGTAATTGCT | SEQ ID NO: 133 | 5bp deletion |
| 1.8 | GCTGGGTCAAGAATCCAT-------CCTCAGTTATGTTCTCAGGGATGTGCTTGTAATTGCT | SEQ ID NO: 134 | 7bp deletion |
| 1.9 | GCTGGGTCAAGAATCCATGGA-ATCCCTCAGTTATGTTCTCAGGGATGTGCTTGTAATTGCT | SEQ ID NO: 135 | 1bp deletion |

FIG. 5B

SEQUENCE LISTING

```
<160> NUMBER OF SEQ ID NOS: 145

<210> SEQ ID NO 1
<211> LENGTH: 4137
<212> TYPE: DNA
<213> ORGANISM: Artificial Sequence
<220> FEATURE:
<223> OTHER INFORMATION: Synthetic

<400> SEQUENCE: 1
atggacaaaa agtactcaat agggctcgac atagggacta actccgttgg atgggccgtc      60
atcaccgacg agtacaaggt gccctccaag aagttcaagg tgttgggaaa caccgacagg     120
cacagcataa agaagaattt gatcggtgcc ctcctcttcg actccggaga gaccgctgag     180
gctaccaggc tcaagaggac cgctagaagg cgctacacca gaaggaagaa cagaatctgc     240
tacctgcagg agatcttctc caacgagatg gccaaggtgg acgactcctt cttccaccgc     300
cttgaggaat cattcctggt ggaggaggat aaaaagcacg agagacaccc aatcttcggg     360
aacatcgtcg acgaggtggc ctaccatgaa aagtaccctg ccatctacca cctgaggaag     420
```

```
aagctggtcg actctaccga caaggctgac ttgcgcttga tttacctggc tctcgctcac    480
atgataaagt tccgcggaca cttcctcatt gagggagacc tgaacccaga caactccgac    540
gtggacaagc tcttcatcca gctcgttcag acctacaacc agcttttcga ggagaaccca    600
atcaacgcca gtggagttga cgccaaggct atcctctctg ctcgtctgtc aaagtccagg    660
aggcttgaga acttgattgc ccagctgcct ggcgaaaaga gaacggact gttcggaaac     720 ttgatcgctc tctccctggg attgactccc aacttcaagt ccaacttcga cctcgccgag    780
gacgctaagt tgcagttgtc taaagacacc tacgacgatg acctcgacaa cttgctggcc    840
cagataggcg accaatacgc cgatctcttc ctcgccgcta agaacttgtc cgacgcaatc    900
ctgctgtccg acatcctgag agtcaacact gagattacca agctcctct gtctgcttcc     960 atgattaagc gctacgacga gcaccaccaa gatctgaccc tgctcaaggc cctggtgaga   1020
cagcagctgc ccgagaagta caaggagatc ttttcgacc agtccaagaa cggctacgcc   1080
ggatacattg acggaggcgc ctcccaggaa gagttctaca agttcatcaa gcccatcctt   1140
gagaagatgg acggtaccga ggagctgttg gtgaagttga acagagagga cctgttgagg   1200
aagcagagaa ccttcgacaa cggaagcatc cctcaccaaa tccacctggg agagctccac   1260
gccatcttga ggaggcagga ggatttctat cccttcctga aggacaaccg cgagaagatt   1320
gagaagatct tgaccttcag aattccttac tacgtcgggc cactcgccag aggaaactct   1380
aggttcgcct ggatgacccg caaatctgaa gagaccatta ctccctggaa cttcgaggaa   1440
gtcgtggaca agggcgcttc cgctcagtct ttcatcgaga ggatgaccaa cttcgataaa   1500
aatctgccca acgagaaggt gctgcccaag cactccctgt tgtacgagta tttcacagtg   1560
tacaacgagc tcaccaaggt gaagtacgtc acagagggaa tgaggaagcc tgccttcttg   1620
tccggagagc agaagaaggc catcgtcgac ctgctcttca agaccaacag gaaggtgact   1680
gtcaagcagc tgaaggagga ctacttcaag aagatcgagt gcttcgactc cgtcgagatc   1740
tctggtgtcg aggacaggtt caacgcctcc cttgggactt accacgatct gctcaagatt   1800
attaaagaca aggacttcct ggacaacgag gagaacgagg acatccttga ggacatcgtg   1860
ctcaccctga ccttgttcga agacaggaa atgatcgaag agaggctcaa gacctacgcc    1920
cacctcttcg acgacaaggt gatgaaacag ctgaagagac gcagatatac cggctgggga   1980
aggctctccc gcaaattgat caacgggatc agggacaagc agtcagggaa gactatactc   2040
gacttcctga agtccgacgg attcgccaac aggaacttca tgcagctcat tcacgacgac   2100
tccttgacct tcaaggagga catccagaag gctcaggtgt ctggacaggg tgactccttg   2160
catgagcaca ttgctaactt ggccggctct cccgctatta agaagggcat tttgcagacc   2220
gtgaaggtcg ttgacgagct cgtgaaggtg atgggacgcc acaagccaga gaacatcgtt   2280
attgagatgg ctcgcgagaa ccaaactacc agaaagggc agaagaattc ccgcgagagg    2340
atgaagcgca ttgaggaggg cataaaagag cttggctctc agatcctcaa ggagcacccc   2400
gtcgagaaca ctcagctgca gaacgagaag ctgtacctgt actacctcca aaacggaagg   2460
gacatgtacg tggaccagga gctggacatc aacaggttgt ccgactacga cgtcgaccac   2520
atcgtgcctc agtccttcct gaaggatgac tccatcgaca taaagtgct gacacgctcc    2580 gataaaaata gaggcaagtc cgacaacgtc ccctccgagg aggtcgtgaa gaagatgaaa   2640
aactactgga gacagctctt gaacgccaag ctcatcaccc agcgtaagtt cgacaacctg   2700
actaaggctg agagaggagg attgtccgag ctcgataagg ccggattcat caagagacag   2760
```

| | |
|---|---|
| ctcgtcgaaa cccgccaaat taccaagcac gtggcccaaa ttctggattc ccgcatgaac | 2820 |
| accaagtacg atgaaaatga caagctgatc cgcgaggtca aggtgatcac cttgaagtcc | 2880 |
| aagctggtct ccgacttccg caaggacttc cagttctaca aggtgaggga gatcaacaac | 2940 |
| taccaccacg cacacgacgc ctacctcaac gctgtcgttg aaccgccct catcaaaaaa | 3000 |
| tatcctaagc tggagtctga gttcgtctac ggcgactaca aggtgtacga cgtgaggaag | 3060 |
| atgatcgcta agtctgagca ggagatcggc aaggccaccg ccaagtactt cttctactcc | 3120 |
| aacatcatga acttcttcaa gaccgagatc actctcgcca acggtgagat caggaagcgc | 3180 |
| ccactgatcg agaccaacgg tgagactgga gatcgtgt gggacaaagg gagggatttc | 3240 |
| gctactgtga ggaaggtgct ctccatgcct caggtgaaca tcgtcaagaa gaccgaagtt | 3300 |
| cagaccggag gattctccaa ggagtccatc ctccccaaga gaaactccga caagctgatc | 3360 |
| gctagaaaga aagactggga ccctaagaag tacgaggct tcgattctcc taccgtggcc | 3420 |
| tactctgtgc tggtcgtggc caaggtggag aagggcaagt ccaagaagct gaaatccgtc | 3480 |
| aaggagctcc tcgggattac catcatggag aggagttcct cgagaagaa ccctatcgac | 3540 |
| ttcctggagg ccaagggata taagaggtg aagaaggacc tcatcatcaa gctgcccaag | 3600 |
| tactccctct tcgagttgga gaacggaagg aagaggatgc tggcttctgc cggagagttg | 3660 |
| cagaagggaa atgagctcgc ccttccctcc aagtacgtga acttcctgta cctcgcctct | 3720 |
| cactatgaaa agttgaaggg ctctcctgag gacaacgagc gaagcagct cttcgtggag | 3780 |
| cagcacaagc actacctgga cgaaattatc gagcagatct ctgagttctc caagcgcgtg | 3840 |
| atattggccg acgccaacct cgacaaggtg ctgtccgcct acaacaagca cagggataag | 3900 |
| cccattcgcg agcaggctga aaacattatc cacctgttta ccctcacaaa cttgggagcc | 3960 |
| cctgctgcct tcaagtactt cgacaccacc attgacagga agatatacac ctccaccaag | 4020 |
| gaggtgctcg acgcaacact catccaccaa tccatcaccg gcctctatga acaaggatt | 4080 |
| gacttgtccc agctgggagg cgactctaga gccgatccca agaagaagag aaaggtg | 4137 |

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Met Ala Pro Lys Lys Arg Lys Val
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Lys Arg Pro Arg Asp Arg His Asp Gly Glu Leu Gly Gly Arg Lys Arg
1               5                   10                  15

Ala Arg

<210> SEQ ID NO 4
<211> LENGTH: 1501
<212> TYPE: DNA
<213> ORGANISM: Glycine max

<400> SEQUENCE: 4

```
gggtttactt attttgtggg tatctatact tttattagat ttttaatcag gctcctgatt      60
tcttttttatt tcgattgaat tcctgaactt gtattattca gtagatcgaa taaattataa    120
aaagataaaa tcataaaata atattttatc ctatcaatca tattaaagca atgaatatgt    180
aaaattaatc ttatctttat tttaaaaaat catataggtt tagtattttt ttaaaaataa    240
agataggatt agttttacta ttcactgctt attactttta aaaaaatcat aaaggtttag    300
tattttttta aaataaatat aggaatagtt ttactattca ctgctttaat agaaaaatag    360
tttaaaattt aagatagttt taatcccagc atttgccacg tttgaacgtg agccgaaacg    420
atgtcgttac attatcttaa cctagctgaa acgatgtcgt cataatatcg ccaaatgcca    480
actggactac gtcgaaccca caaatcccac aaagcgcgtg aaatcaaatc gctcaaacca    540
caaaaagaa caacgcgttt gttacacgct caatcccacg cgagtagagc acagtaacct    600
tcaaataagc gaatggggca taatcagaaa tccgaaataa acctagggg attatcggaa    660
atgaaaagta gctcactcaa tataaaaatc taggaaccct agttttcgtt atcactctgt    720
gctccctcgc tctatttctc agtctctgtg tttgcggctg aggattccga acgagtgacc    780
ttcttcgttt ctcgcaaagg taacagcctc tgctcttgtc tcttcgattc gatctatgcc    840
tgtctcttat ttacgatgat gtttcttcgg ttatgtttt ttatttatgc tttatgctgt    900
tgatgttcgg ttgtttgttt cgctttgttt ttgtggttca gttttttagg attcttttgg    960
tttttgaatc gattaatcgg aagagatttt cgagttattt ggtgtgttgg aggtgaatct   1020
tttttttgag gtcatagatc tgttgtattt gtgttataaa catgcgactt tgtatgattt   1080
tttacgaggt tatgatgttc tggttgtttt attatgaatc tgttgagaca gaaccatgat   1140
ttttgttgat gttcgtttac actattaaag gtttgtttta acaggattaa aagtttttta   1200
agcatgttga aggagtcttg tagatatgta accgtcgata gttttttttgt gggtttgttc   1260
acatgttatc aagcttaatc ttttactatg tatgcgacca tatctggatc cagcaaaggc   1320
gattttttaa ttccttgtga aacttttgta atatgaagtt gaaatttttgt tattggtaaa   1380
ctataaatgt gtgaagttgg agtataacctt taccttctta tttggctttg tgatagttta   1440
atttatatgt attttgagtt ctgacttgta tttctttgaa ttgattctag tttaagtaat   1500
c                                                                   1501
```

<210> SEQ ID NO 5
<211> LENGTH: 434
<212> TYPE: DNA
<213> ORGANISM: Glycine max

<400> SEQUENCE: 5

```
ccgggtgtga tttagtataa agtgaagtaa tggtcaaaag aaaaagtgta aaacgaagta     60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttagtcccca caccgtctaa acttattaaa ttattaatgt ttataactag    420
atgcacaaca acaa                                                     434
```

<210> SEQ ID NO 6
<211> LENGTH: 20
<212> TYPE: DNA
<213> ORGANISM: Glycine max

<400> SEQUENCE: 6
gtgtttggaa cccttgagag                                                    20

<210> SEQ ID NO 7
<211> LENGTH: 20
<212> TYPE: DNA
<213> ORGANISM: Glycine max

<400> SEQUENCE: 7
gcataactga gggatctcca                                                    20

<210> SEQ ID NO 8
<211> LENGTH: 9174
<212> TYPE: DNA
<213> ORGANISM: Artificial Sequence
<220> FEATURE:
<223> OTHER INFORMATION: Synthetic

<400> SEQUENCE: 8
atgagaaagc gccacgcttc ccgaagggag aaaggcggac aggtatccgg taagcggcag         60
ggtcggaaca ggagagcgca cgagggagct tccaggggga aacgcctggt atctttatag        120
tcctgtcggg tttcgccacc tctgacttga gcgtcgattt tgtgatgct cgtcaggggg         180 gcggagccta tggaaaaacg ccagcaacgc ggccttttta cggttcctgg ccttttgctg        240
gccttttgct cacatgttct ttcctgcgtt atcccctgat tctgtggata accgtattac        300
cgcctttgag tgagctgata ccgctcgccg cagccgaacg accgagcgca gcgagtcagt        360
gagcgaggaa gcggaagagc gcccaatacg caaaccgcct ctccccgcgc gttggccgat        420
tcattaatgc aggttgatca gatctcgatc ccgcgaaatt aatacgactc actataggga        480
gaccacaacg gtttccctct agaataatt tgtttaact ttaagaagga gatatacca         540 tggaaaagcc tgaactcacc gcgacgtctg tcgagaagtt tctgatcgaa aagttcgaca        600
gcgtctccga cctgatgcag ctctcggagg gcgaagaatc tcgtgctttc agcttcgatg        660
taggagggcg tggatatgtc ctgcgggtaa atagctgcgc cgatggtttc tacaaagatc        720
gttatgttta tcggcacttt gcatcggccg cgctcccgat tccggaagtg cttgacattg        780
gggaattcag cgagagcctg acctattgca tctcccgccg tgcacagggt gtcacgttgc        840
aagacctgcc tgaaaccgaa ctgcccgctg ttctgcagcc ggtcgcggag gctatggatg        900
cgatcgctgc ggccgatctt agccagacga gcgggttcgg cccattcgga ccgcaaggaa        960
tcggtcaata cactacatgg cgtgatttca tatgcgcgat tgctgatccc catgtgtatc       1020
actggcaaac tgtgatggac gacaccgtca gtgcgtccgt cgcgcaggct ctcgatgagc       1080
tgatgctttg gccgaggac tgccccgaag tccggcacct cgtgcacgcg gatttcggct       1140
ccaacaatgt cctgacggac aatggccgca taacagcggt cattgactgg agcgaggcga       1200
tgttcgggga ttcccaatac gaggtcgcca acatcttctt ctggaggccg tggttggctt       1260
gtatggagca gcagacgcgc tacttcgagc ggaggcatcc ggagcttgca ggatcgccgc       1320
ggctccgggc gtatatgctc cgcattggtc ttgaccaact ctatcagagc ttggttgacg       1380
gcaatttcga tgatgcagct tgggcgcagg tcgatgcgca cgcaatcgtc cgatccgga        1440 ccgggactgt cgggcgtaca caaatcgccc gcagaagcgc ggccgtctgg accgatggct       1500

```
gtgtagaagt actcgccgat agtggaaacc gacgcccag cactcgtccg agggcaaagg    1560
aatagtgagg tacagcttgg atcgatccgg ctgctaacaa agcccgaaag gaagctgagt    1620
tggctgctgc caccgctgag caataactag cataacccct tggggcctct aaacgggtct    1680
tgaggggttt tttgctgaaa ggaggaacta tatccggatg ctcgggcgcg ccggtacccg    1740
ggtgtgattt agtataaagt gaagtaatgg tcaaagaaa aagtgtaaaa cgaagtacct    1800
agtaataagt aatattgaac aaaataaatg gtaaagtgtc agatatataa aataggcttt    1860
aataaaagga agaaaaaaaa caaacaaaaa ataggttgca atggggcaga gcagagtcat    1920
catgaagcta gaaaggctac cgatagataa actatagtta attaaataca ttaaaaaata    1980
cttggatctt tctcttaccc tgtttatatt gagacctgaa acttgagaga gatacactaa    2040
tcttgccttg ttgtttcatt ccctaactta caggactcag cgcatgtcat gtggtctcgt    2100
tccccattta agtcccacac cgtctaaact tattaaatta ttaatgttta taactagatg    2160
cacaacaaca aagcttgtgt ttggaaccct tgagaggttt tagagctaga aatagcaagt    2220
taaaataagg ctagtccgtt atcaacttga aaaagtggca ccgagtcggt gcttttttt    2280 gcggccgcaa ttggatcggg tttacttatt ttgtgggtat ctatactttt attagatttt    2340
taatcaggct cctgatttct ttttatttcg attgaattcc tgaacttgta ttattcagta    2400
gatcgaataa attataaaaa gataaaatca taaaataata ttttatccta tcaatcatat    2460
taaagcaatg aatatgtaaa attaatctta tctttatttt aaaaaatcat ataggtttag    2520
tattttttta aaaataaaga taggattagt tttactattc actgcttatt acttttaaaa    2580
aaatcataaa ggtttagtat tttttaaaa taaatatagg aatagtttta ctattcactg    2640
ctttaataga aaaatagttt aaaatttaag atagttttaa tcccagcatt tgccacgttt    2700
gaacgtgagc cgaaacgatg tcgttacatt atcttaacct agctgaaacg atgtcgtcat    2760
aatatcgcca aatgccaact ggactacgtc gaacccacaa atcccacaaa gcgcgtgaaa    2820
tcaaatcgct caaaccacaa aaaagaacaa cgcgtttgtt acacgctcaa tcccacgcga    2880
gtagagcaca gtaaccttca aataagcgaa tggggcataa tcagaaatcc gaaataaacc    2940 tagggcatt atcggaaatg aaaagtagct cactcaatat aaaaatctag gaaccctagt    3000
tttcgttatc actctgtgct ccctcgctct atttctcagt ctctgtgttt gcggctgagg    3060
attccgaacg agtgaccttc ttcgtttctc gcaaaggtaa cagcctctgc tcttgtctct    3120
tcgattcgat ctatgcctgt ctcttattta cgatgatgtt tcttcggtta tgtttttta    3180 tttatgcttt atgctgttga tgttcggttg tttgtttcgc tttgttttg tggttcagtt    3240 ttttaggatt cttttggttt ttgaatcgat taatcggaag agattttcga gttatttggt    3300
gtgttggagg tgaatctttt ttttgaggtc atagatctgt tgtatttgtg ttataaacat    3360
gcgactttgt atgattttt acgaggttat gatgttctgg ttgttttatt atgaatctgt    3420
tgagacagaa ccatgatttt tgttgatgtt cgtttacact attaaaggtt tgttttaaca    3480
ggattaaaag tttttttaagc atgttgaagg agtcttgtag atatgtaacc gtcgatagtt    3540
tttttgtggg tttgttcaca tgttatcaag cttaatcttt tactatgtat gcgaccatat    3600
ctggatccag caaaggcgat ttttaattc cttgtgaaac ttttgtaata tgaagttgaa    3660
attttgttat tggtaaacta taaatgtgtg aagttggagt ataccttac cttcttattt    3720 ggctttgtga tagtttaatt tatatgtatt ttgagttctg acttgtattt ctttgaattg    3780
attctagttt aagtaatcca tggcaccgaa gaagaagcgc aaggtgatgg acaaaaagta    3840
```

```
ctcaataggg ctcgacatag ggactaactc cgttggatgg gccgtcatca ccgacgagta   3900
caaggtgccc tccaagaagt tcaaggtgtt gggaaacacc gacaggcaca gcataaagaa   3960
gaatttgatc ggtgccctcc tcttcgactc cggagagacc gctgaggcta ccaggctcaa   4020
gaggaccgct agaaggcgct acaccagaag gaagaacaga atctgctacc tgcaggagat   4080
cttctccaac gagatggcca aggtggacga ctccttcttc caccgccttg aggaatcatt   4140
cctggtggag gaggataaaa agcacgagag acacccaatc ttcgggaaca tcgtcgacga   4200
ggtggcctac catgaaaagt accctaccat ctaccacctg aggaagaagc tggtcgactc   4260
taccgacaag gctgacttgc gcttgattta cctggctctc gctcacatga taaagttccg   4320
cggacacttc ctcattgagg gagacctgaa cccagacaac tccgacgtgg acaagctctt   4380
catccagctc gttcagacct acaaccagct tttcgaggag aacccaatca cgccagtgg   4440
agttgacgcc aaggctatcc tctctgctcg tctgtcaaag tccaggaggc ttgagaactt   4500
gattgcccag ctgcctggcg aaaagaagaa cggactgttc ggaaacttga tcgctctctc   4560
cctgggattg actcccaact tcaagtccaa cttcgacctc gccgaggacg ctaagttgca   4620
gttgtctaaa gacacctacg acgatgacct cgacaacttg ctggcccaga taggcgacca   4680
atacgccgat ctcttcctcg ccgctaagaa cttgtccgac gcaatcctgc tgtccgacat   4740
cctgagagtc aacactgaga ttaccaaagc tcctctgtct gcttccatga ttaagcgcta   4800
cgacgagcac caccaagatc tgaccctgct caaggccctg gtgagacagc agctgcccga   4860
gaagtacaag gagatctttt cgaccagtc caagaacggc tacgccggat acattgacgg   4920
aggcgcctcc caggaagagt tctacaagtt catcaagccc atccttgaga gatggacgg   4980
taccgaggag ctgttggtga agttgaacag agaggacctg ttgaggaagc agagaaacctt   5040
cgacaacgga agcatccctc accaaatcca cctgggagag ctccacgcca tcttgaggag   5100
gcaggaggat ttctatccct tcctgaagga caaccgcgag aagattgaga agatcttgac   5160
cttcagaatt ccttactacg tcgggccact cgccagagga aactctaggt tcgcctggat   5220
gacccgcaaa tctgaagaga ccattactcc ctggaacttc gaggaagtcg tggacaaggg   5280
cgcttccgct cagtctttca tcgagaggat gaccaacttc gataaaaatc tgcccaacga   5340
gaaggtgctg cccaagcact ccctgttgta cgagtatttc acagtgtaca acgagctcac   5400
caaggtgaag tacgtcacag agggaatgag gaagcctgcc ttcttgtccg agagcagaa   5460
gaaggccatc gtcgacctgc tcttcaagac caacaggaag gtgactgtca gcagctgaa   5520
ggaggactac ttcaagaaga tcgagtgctt cgactccgtc gagatctctg tgtcgagga   5580
caggttcaac gcctcccttg ggacttacca cgatctgctc aagattatta aagacaagga   5640
cttcctggac aacgaggaga acgaggacat ccttgaggac atcgtgctca ccctgacctt   5700
gttcgaagac agggaaatga tcgaagagag gctcaagacc tacgcccacc tcttcgacga   5760
caaggtgatg aaacagctga agagacgcag atataccggc tggggaaggc tctcccgcaa   5820
attgatcaac gggatcaggg acaagcagtc agggaagact atactcgact tcctgaagtc   5880
cgacggattc gccaacagga acttcatgca gctcattcac gacgactcct tgaccttcaa   5940
ggaggacatc cagaaggctc aggtgtctgg acagggtgac tccttgcatg agcacattgc   6000
taacttggcc ggctctcccg ctattaagaa gggcattttg cagaccgtga aggtcgttga   6060
cgagctcgtg aaggtgatgg gacgccacaa gccagagaac atcgttattg agatggctcg   6120
cgagaaccaa actacccaga aagggcagaa gaattcccgc gagaggatga gcgcattga   6180
ggagggcata aaagagcttg gctctcagat cctcaaggag cacccgtcg agaacactca   6240
```

```
gctgcagaac gagaagctgt acctgtacta cctccaaaac ggaagggaca tgtacgtgga    6300
ccaggagctg gacatcaaca ggttgtccga ctacgacgtc gaccacatcg tgcctcagtc    6360
cttcctgaag gatgactcca tcgacaataa agtgctgaca cgctccgata aaaatagagg    6420
caagtccgac aacgtcccct ccgaggaggt cgtgaagaag atgaaaaact actggagaca    6480
gctcttgaac gccaagctca tcacccagcg taagttcgac aacctgacta aggctgagag    6540
aggaggattg tccgagctcg ataaggccgg attcatcaag agacagctcg tcgaaacccg    6600
ccaaattacc aagcacgtgg cccaaattct ggattcccgc atgaacacca agtacgatga    6660
aaatgacaag ctgatccgcg aggtcaaggt gatcaccttg aagtccaagc tggtctccga    6720
cttccgcaag gacttccagt tctacaaggt gagggagatc aacaactacc accacgcaca    6780
cgacgcctac ctcaacgctg tcgttggaac cgccctcatc aaaaaatatc ctaagctgga    6840
gtctgagttc gtctacggcg actacaaggt gtacgacgtg aggaagatga tcgctaagtc    6900
tgagcaggag atcggcaagg ccaccgccaa gtacttcttc tactccaaca tcatgaactt    6960
cttcaagacc gagatcactc tcgccaacgg tgagatcagg aagcgcccac tgatcgagac    7020
caacggtgag actggagaga tcgtgtggga caaaggaggg gatttcgcta ctgtgaggaa    7080
ggtgctctcc atgcctcagg tgaacatcgt caagaagacc gaagttcaga ccggaggatt    7140
ctccaaggag tccatcctcc ccaagagaaa ctccgacaag ctgatcgcta aaagaaaga    7200 ctgggaccct aagaagtacg gaggcttcga ttctcctacc gtggcctact ctgtgctggt    7260
cgtggccaag gtggagaagg gcaagtccaa gaagctgaaa tccgtcaagg agctcctcgg    7320
gattaccatc atggagagga gttccttcga gaagaaccct atcgacttcc tggaggccaa    7380
gggatataaa gaggtgaaga aggacctcat catcaagctg cccaagtact ccctcttcga    7440
gttggagaac ggaaggaaga ggatgctggc ttctgccgga gagttgcaga agggaaatga    7500
gctcgccctt ccctccaagt acgtgaactt cctgtacctc gcctctcact atgaaaagtt    7560
gaagggctct cctgaggaca cgagcagaa gcagctcttc gtggagcagc acaagcacta    7620
cctggacgaa attatcgagc agatctctga gttctccaag cgcgtgatat tggccgacgc    7680
caacctcgac aaggtgctgt ccgcctacaa caagcacagg ataagccca ttcgcgagca    7740 ggctgaaaac attatccacc tgtttaccct cacaaacttg ggagcccctg ctgccttcaa    7800
gtacttcgac accaccattg acaggaagag atacacctcc accaaggagg tgctcgacgc    7860
aacactcatc caccaatcca tcaccggcct ctatgaaaca aggattgact tgtcccagct    7920
gggaggcgac tctagagccg atcccaagaa gaagagaaag gtgaagagac acgggaccg    7980 ccacgatggc gagctgggag ccgcaagcg ggcaaggtag gttaacctag acttgtccat    8040
cttctggatt ggccaactta attaatgtat gaaataaaag gatgcacaca tagtgacatg    8100
ctaatcacta taatgtgggc atcaaagttg tgtgttatgt gtaattacta gttatctgaa    8160
taaaagagaa agagatcatc catatttctt atcctaaatg aatgtcacgt gtctttataa    8220
ttctttgatg aaccagatgc atttcattaa ccaaatccat atacatataa atattaatca    8280
tatataatta atatcaattg ggttagcaaa acaaatctag tctaggtgtg ttttgcgaat    8340
tcgatatcaa gcttatcgat accgtcgagg ggggcccgg taccggcgcg ccgttctata    8400
gtgtcaccta atcgtatgt gtatgataca taggttatg tattaattgt agccgcgttc    8460
taacgacaat atgtccatat ggtgcactct cagtacaatc tgctctgatg ccgcatagtt    8520
aagccagccc cgacacccgc caacacccgc tgacgcgccc tgacgggctt gtctgctccc    8580
```

| | |
|---|---|
| ggcatccgct tacagacaag ctgtgaccgt ctccgggagc tgcatgtgtc agaggttttc | 8640 |
| accgtcatca ccgaaacgcg cgagacgaaa gggcctcgtg atacgcctat ttttataggt | 8700 |
| taatgtcatg accaaaatcc cttaacgtga gttttcgttc cactgagcgt cagaccccgt | 8760 |
| agaaaagatc aaaggatctt cttgagatcc ttttttttctg cgcgtaatct gctgcttgca | 8820 |
| aacaaaaaaa ccaccgctac cagcggtggt ttgtttgccg gatcaagagc taccaactct | 8880 |
| ttttccgaag gtaactggct tcagcagagc gcagatacca aatactgttc ttctagtgta | 8940 |
| gccgtagtta ggccaccact tcaagaactc tgtagcaccg cctacatacc tcgctctgct | 9000 |
| aatcctgtta ccagtggctg ctgccagtgg cgataagtcg tgtcttaccg ggttggactc | 9060 |
| aagacgatag ttaccggata aggcgcagcg gtcgggctga acggggggtt cgtgcacaca | 9120 |
| gcccagcttg gagcgaacga cctacaccga actgagatac ctacagcgtg agct | 9174 |

<210> SEQ ID NO 9
<211> LENGTH: 9174
<212> TYPE: DNA
<213> ORGANISM: Artificial Sequence
<220> FEATURE:
<223> OTHER INFORMATION: Synthetic

<400> SEQUENCE: 9

| | |
|---|---|
| cggtaccggc gcgccgttct atagtgtcac ctaaatcgta tgtgtatgat acataaggtt | 60 |
| atgtattaat tgtagccgcg ttctaacgac aatatgtcca tatggtgcac tctcagtaca | 120 |
| atctgctctg atgccgcata gttaagccag ccccgacacc cgccaacacc cgctgacgcg | 180 |
| ccctgacggg cttgtctgct cccggcatcc gcttacagac aagctgtgac cgtctccggg | 240 |
| agctgcatgt gtcagaggtt ttcaccgtca tcaccgaaac gcgcgagacg aaagggcctc | 300 |
| gtgatacgcc tatttttata ggttaatgtc atgaccaaaa tcccttaacg tgagttttcg | 360 |
| ttccactgag cgtcagaccc cgtagaaaag atcaaaggat cttcttgaga tccttttttt | 420 |
| ctgcgcgtaa tctgctgctt gcaaacaaaa aaaccaccgc taccagcggt ggtttgtttg | 480 |
| ccggatcaag agctaccaac tcttttttccg aaggtaactg gcttcagcag agcgcagata | 540 |
| ccaaatactg ttcttctagt gtagccgtag ttaggccacc acttcaagaa ctctgtagca | 600 |
| ccgcctacat acctcgctct gctaatcctg ttaccagtgg ctgctgccag tggcgataag | 660 |
| tcgtgtctta ccgggttgga ctcaagacga tagttaccgg ataaggcgca gcggtcgggc | 720 |
| tgaacggggg gttcgtgcac acagcccagc ttggagcgaa cgacctacac cgaactgaga | 780 |
| tacctacagc gtgagctatg agaaagcgcc acgcttcccg aagggagaaa ggcggacagg | 840 |
| tatccggtaa gcggcagggt cggaacagga gagcgcacga gggagcttcc agggggaaac | 900 |
| gcctggtatc tttatagtcc tgtcgggttt cgccacctct gacttgagcg tcgatttttg | 960 |
| tgatgctcgt caggggggcg gagcctatgg aaaaacgcca gcaacgcggc ctttttacgg | 1020 |
| ttcctggcct tttgctggcc ttttgctcac atgttctttc ctgcgttatc ccctgattct | 1080 |
| gtggataacc gtattaccgc ctttgagtga gctgataccg ctcgccgcag ccgaacgacc | 1140 |
| gagcgcagcg agtcagtgag cgaggaagcg gaagagcgcc caatacgcaa accgcctctc | 1200 |
| cccgcgcgtt ggccgattca ttaatgcagg ttgatcagat ctcgatcccg cgaaattaat | 1260 |
| acgactcact ataggggagac cacaacggtt tccctctaga ataattttg tttaacttta | 1320 |
| agaaggagat atacccatgg aaaagcctga actcaccgcg acgtctgtcg agaagtttct | 1380 |
| gatcgaaaag ttcgacagcg tctccgacct gatgcagctc tcgagggcg aagaatctcg | 1440 |
| tgctttcagc ttcgatgtag gagggcgtgg atatgtcctg cgggtaaata gctgcgccga | 1500 |

```
tggtttctac aaagatcgtt atgtttatcg gcactttgca tcggccgcgc tcccgattcc    1560
ggaagtgctt gacattgggg aattcagcga gagcctgacc tattgcatct cccgccgtgc    1620
acagggtgtc acgttgcaag acctgcctga aaccgaactg cccgctgttc tgcagccggt    1680
cgcggaggct atggatgcga tcgctgcggc cgatcttagc cagacgagcg ggttcggccc    1740
attcggaccg caaggaatcg gtcaatacac tacatggcgt gatttcatat gcgcgattgc    1800
tgatccccat gtgtatcact ggcaaactgt gatggacgac accgtcagtg cgtccgtcgc    1860
gcaggctctc gatgagctga tgctttgggc cgaggactgc cccgaagtcc ggcacctcgt    1920
gcacgcggat ttcggctcca acaatgtcct gacggacaat ggccgcataa cagcggtcat    1980
tgactggagc gaggcgatgt tcggggattc ccaatacgag gtcgccaaca tcttcttctg    2040
gaggccgtgg ttggcttgta tggagcagca gacgcgctac ttcgagcgga ggcatccgga    2100
gcttgcagga tcgccgcggc tccgggcgta tatgctccgc attggtcttg accaactcta    2160
tcagagcttg gttgacggca atttcgatga tgcagcttgg gcgcagggtc gatgcgacgc    2220
aatcgtccga tccggagccg ggactgtcgg gcgtacacaa atcgcccgca gaagcgcggc    2280
cgtctggacc gatggctgtg tagaagtact cgccgatagt ggaaaccgac gccccagcac    2340
tcgtccgagg gcaaaggaat agtgaggtac agcttggatc gatccggctg ctaacaaagc    2400
ccgaaaggaa gctgagttgg ctgctgccac cgctgagcaa taactagcat aaccccttgg    2460
ggcctctaaa cgggtcttga ggggtttttt gctgaaagga ggaactatat ccggatgctc    2520
gggcgcgccg gtacccgggt gtgatttagt ataaagtgaa gtaatggtca aaagaaaaag    2580
tgtaaaacga agtacctagt aataagtaat attgaacaaa ataaatggta aagtgtcaga    2640
tatataaaat aggctttaat aaaaggaaga aaaaaaacaa acaaaaaata ggttgcaatg    2700
gggcagagca gagtcatcat gaagctagaa aggctaccga tagataaact atagttaatt    2760
aaatacatta aaaatactt ggatctttct cttaccctgt ttatattgag acctgaaact    2820
tgagagagat acactaatct tgccttgttg tttcattccc taacttacag gactcagcgc    2880
atgtcatgtg gtctcgttcc ccatttaagt cccacaccgt ctaaacttat taaattatta    2940
atgtttataa ctagatgcac aacaacaaag cttgcataac tgagggatct ccagttttag    3000
agctagaaat agcaagttaa aataaggcta gtccgttatc aacttgaaaa agtggcaccg    3060
agtcggtgct ttttttgcg gccgcaattg gatcgggttt acttattttg tgggtatcta    3120 tactttatt agattttta tcaggctcct gatttctttt tatttcgatt gaattcctga    3180
acttgtatta ttcagtagat cgaataaatt ataaaaagat aaaatcataa ataatatttt    3240
tatcctatca atcatattaa agcaatgaat atgtaaaatt aatcttatct ttatttaaa    3300 aaatcatata ggtttagtat ttttttaaaa ataagatag gattagtttt actattcact    3360
gcttattact tttaaaaaaa tcataaaggt ttagtatttt tttaaaataa ataaggaat    3420 agttttacta ttcactgctt taatagaaaa atagtttaaa atttaagata gttttaatcc    3480
cagcatttgc cacgtttgaa cgtgagccga aacgatgtcg ttacattatc ttaacctagc    3540
tgaaacgatg tcgtcataat atcgccaaat gccaactgga ctacgtcgaa cccacaaatc    3600
ccacaaagcg cgtgaaatca aatcgctcaa accacaaaaa agaacaacgc gtttgttaca    3660
cgctcaatcc cacgcgagta gagcacagta accttcaaat aagcgaatgg ggcataatca    3720
gaaatccgaa ataaacctag ggcattatc ggaaatgaaa agtagctcac tcaatataaa    3780
aatctaggaa ccctagtttt cgttatcact ctgtgctccc tcgctctatt tctcagtctc    3840
```

```
tgtgtttgcg gctgaggatt ccgaacgagt gaccttcttc gtttctcgca aaggtaacag    3900
cctctgctct tgtctcttcg attcgatcta tgcctgtctc ttatttacga tgatgtttct    3960
tcggttatgt tttttatttt atgctttatg ctgttgatgt tcggttgttt gtttcgcttt    4020
gttttgtgg ttcagttttt taggattctt ttggttttg aatcgattaa tcggaagaga     4080
ttttcgagtt atttggtgtg ttggaggtga atcttttttt tgaggtcata gatctgttgt    4140
atttgtgtta taaacatgcg actttgtatg attttttacg aggttatgat gttctggttg    4200
ttttattatg aatctgttga gacagaacca tgattttgt tgatgttcgt ttacactatt     4260
aaaggtttgt tttaacagga ttaaaagttt tttaagcatg ttgaaggagt cttgtagata    4320
tgtaaccgtc gatagttttt ttgtgggttt gttcacatgt tatcaagctt aatcttttac    4380
tatgtatgcg accatatctg gatccagcaa aggcgatttt ttaattcctt gtgaaacttt    4440
tgtaatatga agttgaaatt tgttattgg taaactataa atgtgtgaag ttggagtata     4500
cctttacctt cttatttggc tttgtgatag tttaatttat atgtattttg agttctgact    4560
tgtatttctt tgaattgatt ctagtttaag taatccatgg caccgaagaa gaagcgcaag    4620
gtgatggaca aaaagtactc aataggctc gacataggga ctaactccgt tggatgggcc     4680
gtcatcaccg acgagtacaa ggtgcctcc aagaagttca aggtgttggg aaacaccgac     4740
aggcacagca taaagaagaa tttgatcggt gccctcctct tcgactccgg agagaccgct    4800
gaggctacca ggctcaagag gaccgctaga aggcgctaca ccagaaggaa gaacagaatc    4860
tgctacctgc aggagatctt ctccaacgag atggccaagg tggacgactc cttcttccac    4920
cgccttgagg aatcattcct ggtggaggag gataaaaagc acgagagaca cccaatcttc    4980
gggaacatcg tcgacgaggt ggcctaccat gaaaagtacc ctaccatcta ccacctgagg    5040
aagaagctgt cgactctac cgacaaggct gacttgcgct tgatttacct ggctctcgct     5100
cacatgataa agttccgcgg acacttcctc attgagggag acctgaaccc agacaactcc    5160
gacgtggaca gctcttcat ccagctcgtt cagacctaca accagctttt cgaggagaac     5220
ccaatcaacg ccagtggagt tgacgccaag gctatcctct ctgctcgtct gtcaaagtcc    5280
aggaggcttg agaacttgat tgcccagctg cctggcgaaa agaagaacgg actgttcgga    5340
aacttgatcg ctctctccct gggattgact cccaacttca agtccaactt cgacctcgcc    5400
gaggacgcta agttgcagtt gtctaaagac acctacgacg atgacctcga caacttgctg    5460
gcccagatag gcgaccaata cgccgatctc ttcctcgccg ctaagaactt gtccgacgca    5520
atcctgctgt ccgacatcct gagagtcaac actgagatta ccaaagctcc tctgtctgct    5580
tccatgatta agcgctacga cgagcaccac caagatctga ccctgctcaa ggccctggtg    5640
agacagcagc tgcccgagaa gtacaaggag atctttttcg accagtccaa gaacggctac    5700
gccggataca ttgacggagg cgcctcccag gaagagttct acaagttcat caagcccatc    5760
cttgagaaga tggacggtac cgaggagctg ttggtgaagt tgaacagaga ggacctgttg    5820
aggaagcaga gaaccttcga caacggaagc atccctcacc aaatccacct gggagagctc    5880
cacgccatct tgaggaggca ggaggatttc tatcccttcc tgaaggacaa ccgcgagaag    5940
attgagaaga tcttgacctt cagaattcct tactacgtcg gccactcgc cagaggaaac     6000
tctaggttcg cctggatgac ccgcaaatct gaagagacca ttactccctg gaacttcgag    6060
gaagtcgtgg acaagggcgc ttccgctcag tctttcatcg agaggatgac caacttcgat    6120
aaaaatctgc ccaacgagaa ggtgctgccc aagcactccc tgttgtacga gtatttcaca    6180
gtgtacaacg agctcaccaa ggtgaagtac gtcacagagg gaatgaggaa gcctgccttc    6240
```

```
ttgtccggag agcagaagaa ggccatcgtc gacctgctct tcaagaccaa caggaaggtg    6300
actgtcaagc agctgaagga ggactacttc aagaagatcg agtgcttcga ctccgtcgag    6360
atctctggtg tcgaggacag gttcaacgcc tcccttggga cttaccacga tctgctcaag    6420
attattaaag acaaggactt cctggacaac gaggagaacg aggacatcct tgaggacatc    6480
gtgctcaccc tgaccttgtt cgaagacagg gaaatgatcg aagagaggct caagacctac    6540
gcccacctct tcgacgacaa ggtgatgaaa cagctgaaga cgcagata taccggctgg    6600 ggaaggctct cccgcaaatt gatcaacggg atcagggaca gcagtcagg gaagactata    6660 ctcgacttcc tgaagtccga cggattcgcc aacaggaact tcatgcagct cattcacgac    6720
gactccttga ccttcaagga ggacatccag aaggctcagg tgtctggaca gggtgactcc    6780
ttgcatgagc acattgctaa cttggccggc tctcccgcta ttaagaaggg cattttgcag    6840
accgtgaagg tcgttgacga gctcgtgaag gtgatgggac gccacaagcc agagaacatc    6900
gttattgaga tggctcgcga gaaccaaact acccagaaag gcagaagaa ttcccgcgag    6960 aggatgaagc gcattgagga gggcataaaa gagcttggct ctcagatcct caaggagcac    7020
cccgtcgaga cactcagct gcagaacgag aagctgtacc tgtactacct ccaaaacgga    7080
agggacatgt acgtggacca ggagctggac atcaacaggt tgtccgacta cgacgtcgac    7140
cacatcgtgc ctcagtcctt cctgaaggat gactccatcg acaataaagt gctgacacgc    7200
tccgataaaa atagaggcaa gtccgacaac gtccctccg aggaggtcgt gaagaagatg    7260
aaaaactact ggagacagct cttgaacgcc aagctcatca cccagcgtaa gttcgacaac    7320
ctgactaagg ctgagagagg aggattgtcc gagctcgata aggccggatt catcaagaga    7380
cagctcgtcg aaacccgcca aattaccaag cacgtggccc aaattctgga ttcccgcatg    7440
aacaccaagt acgatgaaaa tgacaagctg atccgcgagg tcaaggtgat caccttgaag    7500
tccaagctgg tctccgactt ccgcaaggac ttccagttct acaaggtgag ggagatcaac    7560
aactaccacc acgcacacga cgcctacctc aacgctgtcg ttggaaccgc cctcatcaaa    7620
aaatatccta gctggagtc tgagttcgtc tacggcgact acaaggtgta cgacgtgagg    7680
aagatgatcg ctaagtctga gcaggagatc ggcaaggcca ccgccaagta cttcttctac    7740
tccaacatca tgaacttctt caagaccgag atcactctcg ccaacggtga gatcaggaag    7800
cgcccactga tcgagaccaa cggtgagact ggagagatcg tgtgggacaa agggagggat    7860
ttcgctactg tgaggaaggt gctctccatg cctcaggtga acatcgtcaa gaagaccgaa    7920
gttcagaccg gaggattctc caaggagtcc atcctcccca agagaaactc cgacaagctg    7980
atcgctagaa agaaagactg ggaccctaag aagtacggag gcttcgattc tcctaccgtg    8040
gcctactctg tgctggtcgt ggccaaggtg gagaagggca agtccaagaa gctgaaatcc    8100
gtcaaggagc tcctcgggat taccatcatg gagaggagtt ccttcgagaa gaaccctatc    8160
gacttcctgg aggccaaggg atataaagag gtgaagaagg acctcatcat caagctgccc    8220
aagtactccc tcttcgagtt ggagaacgga aggaagagga tgctggcttc tgccggagag    8280
ttgcagaagg gaaatgagct cgcccttccc tccaagtacg tgaacttcct gtacctcgcc    8340
tctcactatg aaaagttgaa gggctctcct gaggacaacg agcagaagca gctcttcgtg    8400
gagcagcaca gcactacct ggacgaaatt atcgagcaga tctctgagtt ctccaagcgc    8460
gtgatattgg ccgacgccaa cctcgacaag gtgctgtccg cctacaacaa gcacagggat    8520
aagcccattc gcgagcaggc tgaaaacatt atccacctgt ttaccctcac aaacttggga    8580
```

```
gcccctgctg ccttcaagta cttcgacacc accattgaca ggaagagata cacctccacc    8640
aaggaggtgc tcgacgcaac actcatccac caatccatca ccggcctcta tgaaacaagg    8700
attgacttgt cccagctggg aggcgactct agagccgatc ccaagaagaa gagaaaggtg    8760
aagagaccac gggaccgcca cgatggcgag ctgggaggcc gcaagcgggc aaggtaggtt    8820
aacctagact tgtccatctt ctggattggc caacttaatt aatgtatgaa ataaaaggat    8880
gcacacatag tgacatgcta atcactataa tgtgggcatc aaagttgtgt gttatgtgta    8940
attactagtt atctgaataa aagagaaaga gatcatccat atttcttatc ctaaatgaat    9000
gtcacgtgtc tttataattc tttgatgaac cagatgcatt tcattaacca aatccatata    9060
catataaata ttaatcatat ataattaata tcaattgggt tagcaaaaca aatctagtct    9120
aggtgtgttt tgcgaattcg atatcaagct tatcgatacc gtcgaggggg ggcc          9174
```

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tcgtgtggcc aaagtggaa                                                  19

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
tttgtgtttg gaacccttga ga                                              22

<210> SEQ ID NO 12
<211> LENGTH: 16
<212> TYPE: DNA
<213> ORGANISM: Artificial Sequence
<220> FEATURE:
<223> OTHER INFORMATION: Synthetic

<400> SEQUENCE: 12
ttcaagggaa gaagcc                                                     16

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
ccgtgtggcc aaagttgaa                                                  19

<210> SEQ ID NO 14
<211> LENGTH: 16
<212> TYPE: DNA
<213> ORGANISM: Artificial Sequence
<220> FEATURE:
<223> OTHER INFORMATION: Synthetic

<400> SEQUENCE: 14
ttcagcagaa gaagcc                                                     16

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
taatggatac caaaaggaag c                                              21

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
caagcacatc cctgagaaca taac                                           24

<210> SEQ ID NO 17
<211> LENGTH: 17
<212> TYPE: DNA
<213> ORGANISM: Artificial Sequence
<220> FEATURE:
<223> OTHER INFORMATION: Synthetic

<400> SEQUENCE: 17
aatccatgga gatccct                                                   17

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
ataccaacaa aagggttctt c                                              21

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
ccttcttcca ccgccttga                                                 19

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
tgggtgtctc tcgtgctttt t                                              21

<210> SEQ ID NO 21
<211> LENGTH: 19
<212> TYPE: DNA
<213> ORGANISM: Artificial Sequence
<220> FEATURE:

<223> OTHER INFORMATION: Synthetic

<400> SEQUENCE: 21
aatcattcct ggtggagga					19

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
tgatgcccac attatagtga ttagc				25

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
catcttctgg attggccaac tt				22

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
actatgtgtg catcctt					17

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
ttcaagttgg gcttttcag aag				23

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
tctccttggt gctctcatca ca				22

<210> SEQ ID NO 27
<211> LENGTH: 15
<212> TYPE: DNA
<213> ORGANISM: Artificial Sequence
<220> FEATURE:
<223> OTHER INFORMATION: Synthetic

<400> SEQUENCE: 27
ctgcagcaga accaa					15

```
<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
actacctggt ttaaaattga gggattg                                            27

<210> SEQ ID NO 29
<211> LENGTH: 27
<212> TYPE: DNA
<213> ORGANISM: Artificial Sequence
<220> FEATURE:
<223> OTHER INFORMATION: Synthetic

<400> SEQUENCE: 29
tgtcacttcc ctccattcat tttgtac                                            27

<210> SEQ ID NO 30
<211> LENGTH: 28
<212> TYPE: DNA
<213> ORGANISM: Artificial Sequence
<220> FEATURE:
<223> OTHER INFORMATION: Synthetic

<400> SEQUENCE: 30
atggcttatt ttccatgaga aataaggg                                           28

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
tctaggttat tacgcaccac ccacc                                              25

<210> SEQ ID NO 32
<211> LENGTH: 28
<212> TYPE: DNA
<213> ORGANISM: Artificial Sequence
<220> FEATURE:
<223> OTHER INFORMATION: Synthetic

<400> SEQUENCE: 32
aagttgtcta aagccaaatg aaatgagg                                           28

<210> SEQ ID NO 33
<211> LENGTH: 25
<212> TYPE: DNA
<213> ORGANISM: Artificial Sequence
<220> FEATURE:
<223> OTHER INFORMATION: Synthetic

<400> SEQUENCE: 33
ccctgagaaa agagaggaac cacac                                              25

<210> SEQ ID NO 34
<211> LENGTH: 31
<212> TYPE: DNA
<213> ORGANISM: Artificial Sequence
<220> FEATURE:
<223> OTHER INFORMATION: Synthetic
```

```
<400> SEQUENCE: 34
ttcaattcaa tcaatgaaga atgaaataat g                              31

<210> SEQ ID NO 35
<211> LENGTH: 62
<212> TYPE: DNA
<213> ORGANISM: Glycine max

<400> SEQUENCE: 35
gtggaagttc aagggaagaa gcctctctca agggttccaa acacaaagcc accattcact 60
gt                                                              62

<210> SEQ ID NO 36
<211> LENGTH: 51
<212> TYPE: DNA
<213> ORGANISM: Artificial Sequence
<220> FEATURE:
<223> OTHER INFORMATION: Synthetic

<400> SEQUENCE: 36
gtggaagttc aagggaagaa gcgttccaaa cacaaagcca ccattcactg t         51

<210> SEQ ID NO 37
<211> LENGTH: 55
<212> TYPE: DNA
<213> ORGANISM: Artificial Sequence
<220> FEATURE:
<223> OTHER INFORMATION: Synthetic

<400> SEQUENCE: 37
gtggaagttc aagggaagaa gcctctcttc aaacacaaa gccaccattc actgt     55

<210> SEQ ID NO 38
<211> LENGTH: 54
<212> TYPE: DNA
<213> ORGANISM: Artificial Sequence
<220> FEATURE:
<223> OTHER INFORMATION: Synthetic

<400> SEQUENCE: 38
gtggaagttc aagggaagaa gcctctctcc aaacacaaag ccaccattca ctgt     54

<210> SEQ ID NO 39
<211> LENGTH: 57
<212> TYPE: DNA
<213> ORGANISM: Artificial Sequence
<220> FEATURE:
<223> OTHER INFORMATION: Synthetic

<400> SEQUENCE: 39
gtggaagttc aagggaagaa gcctctcggt tccaaacaca agccaccat tcactgt   57

<210> SEQ ID NO 40
<211> LENGTH: 55
<212> TYPE: DNA
<213> ORGANISM: Artificial Sequence
<220> FEATURE:
<223> OTHER INFORMATION: Synthetic

<400> SEQUENCE: 40
gtggaagttc aagggaagaa gcctctcttc aaacacaaa gccaccattc actgt     55

<210> SEQ ID NO 41
<211> LENGTH: 58
```

```
<212> TYPE: DNA
<213> ORGANISM: Artificial Sequence
<220> FEATURE:
<223> OTHER INFORMATION: Synthetic

<400> SEQUENCE: 41
gtggaagttc aagggaagaa gcctctctgg ttccaaacac aaagccacca ttcactgt      58

<210> SEQ ID NO 42
<211> LENGTH: 61
<212> TYPE: DNA
<213> ORGANISM: Artificial Sequence
<220> FEATURE:
<223> OTHER INFORMATION: Synthetic

<400> SEQUENCE: 42
gtggaagttc aagggaagaa gcctctctaa gggttccaaa cacaaagcca ccattcactg    60
t                                                                    61

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
gtggaagttc aagggaagaa agccaccatt cactgt                              36

<210> SEQ ID NO 44
<211> LENGTH: 62
<212> TYPE: DNA
<213> ORGANISM: Glycine max

<400> SEQUENCE: 44
gttgaaattc agcagaagaa gcctctctca agggttccaa acacaaagcc accattcact    60
gt                                                                    62

<210> SEQ ID NO 45
<211> LENGTH: 58
<212> TYPE: DNA
<213> ORGANISM: Artificial Sequence
<220> FEATURE:
<223> OTHER INFORMATION: Synthetic

<400> SEQUENCE: 45
gttgaaattc agcagaagaa gcctctcggg ttccaaacac aaagccacca ttcactgt      58

<210> SEQ ID NO 46
<211> LENGTH: 51
<212> TYPE: DNA
<213> ORGANISM: Artificial Sequence
<220> FEATURE:
<223> OTHER INFORMATION: Synthetic

<400> SEQUENCE: 46
gttgaaattc agcagaagaa gcctctcaaa cacaaagcca ccattcactg t              51

<210> SEQ ID NO 47
<211> LENGTH: 46
<212> TYPE: DNA
<213> ORGANISM: Artificial Sequence
<220> FEATURE:
<223> OTHER INFORMATION: Synthetic
```

```
<400> SEQUENCE: 47
gttgaaattc agcagaagaa gcctccacaa agccaccatt cactgt          46

<210> SEQ ID NO 48
<211> LENGTH: 51
<212> TYPE: DNA
<213> ORGANISM: Artificial Sequence
<220> FEATURE:
<223> OTHER INFORMATION: Synthetic

<400> SEQUENCE: 48
gttgaaattc agcagaagaa gcctctcaaa cacaaagcca ccattcactg t     51

<210> SEQ ID NO 49
<211> LENGTH: 63
<212> TYPE: DNA
<213> ORGANISM: Artificial Sequence
<220> FEATURE:
<223> OTHER INFORMATION: Synthetic

<400> SEQUENCE: 49
gttgaaattc agcagaagaa gcctctcttc aagggttcca acacaaagc caccattcac   60 tgt                                                               63

<210> SEQ ID NO 50
<211> LENGTH: 55
<212> TYPE: DNA
<213> ORGANISM: Artificial Sequence
<220> FEATURE:
<223> OTHER INFORMATION: Synthetic

<400> SEQUENCE: 50
gttgaaattc agcagaagaa gcctctcttc caaacacaaa gccaccattc actgt      55

<210> SEQ ID NO 51
<211> LENGTH: 54
<212> TYPE: DNA
<213> ORGANISM: Artificial Sequence
<220> FEATURE:
<223> OTHER INFORMATION: Synthetic

<400> SEQUENCE: 51
gttgaaattc agcagaagaa gcctctctcc aaacacaaag ccaccattca ctgt        54

<210> SEQ ID NO 52
<211> LENGTH: 54
<212> TYPE: DNA
<213> ORGANISM: Artificial Sequence
<220> FEATURE:
<223> OTHER INFORMATION: Synthetic

<400> SEQUENCE: 52
gttgaaattc agcagaagaa gcctctctcc aaacacaaag ccaccattca ctgt        54

<210> SEQ ID NO 53
<211> LENGTH: 62
<212> TYPE: DNA
<213> ORGANISM: Glycine max

<400> SEQUENCE: 53
gtggaagttc aagggaagaa gcctctctca agggttccaa acacaaagcc accattcact   60
gt                                                                  62
```

```
<210> SEQ ID NO 54
<211> LENGTH: 55
<212> TYPE: DNA
<213> ORGANISM: Artificial Sequence
<220> FEATURE:
<223> OTHER INFORMATION: Synthetic

<400> SEQUENCE: 54
gtggaagttc aagggaagaa gcctctcttc caaacacaaa gccaccattc actgt      55

<210> SEQ ID NO 55
<211> LENGTH: 55
<212> TYPE: DNA
<213> ORGANISM: Artificial Sequence
<220> FEATURE:
<223> OTHER INFORMATION: Synthetic

<400> SEQUENCE: 55
gtggaagttc aagggaagaa gccagggttc caaacacaaa gccaccattc actgt      55

<210> SEQ ID NO 56
<211> LENGTH: 62
<212> TYPE: DNA
<213> ORGANISM: Glycine max

<400> SEQUENCE: 56
gttgaaattc agcagaagaa gcctctctca agggttccaa acacaaagcc accattcact  60
gt                                                                62

<210> SEQ ID NO 57
<211> LENGTH: 57
<212> TYPE: DNA
<213> ORGANISM: Artificial Sequence
<220> FEATURE:
<223> OTHER INFORMATION: Synthetic

<400> SEQUENCE: 57
gttgaaattc agcagaagaa gcctctcggt tccaaacaca aagccaccat tcactgt    57

<210> SEQ ID NO 58
<211> LENGTH: 55
<212> TYPE: DNA
<213> ORGANISM: Artificial Sequence
<220> FEATURE:
<223> OTHER INFORMATION: Synthetic

<400> SEQUENCE: 58
gttgaaattc agcagaagaa gcctctcttc caaacacaaa gccaccattc actgt      55

<210> SEQ ID NO 59
<211> LENGTH: 62
<212> TYPE: DNA
<213> ORGANISM: Glycine max

<400> SEQUENCE: 59
gctgggtcaa gaatccatgg agatccctca gttatgttct cagggatgtg cttgtaattg  60
ct                                                                62

<210> SEQ ID NO 60
<211> LENGTH: 60
<212> TYPE: DNA
<213> ORGANISM: Artificial Sequence
<220> FEATURE:
<223> OTHER INFORMATION: Synthetic
```

<400> SEQUENCE: 60

```
gctgggtcaa gaatccatgg atccctcagt tatgttctca gggatgtgct tgtaattgct    60
```

<210> SEQ ID NO 61
<211> LENGTH: 58
<212> TYPE: DNA
<213> ORGANISM: Artificial Sequence
<220> FEATURE:
<223> OTHER INFORMATION: Synthetic

<400> SEQUENCE: 61

```
gctgggtcaa gaatccatgg ccctcagtta tgttctcagg gatgtgcttg taattgct    58
```

<210> SEQ ID NO 62
<211> LENGTH: 62
<212> TYPE: DNA
<213> ORGANISM: Glycine max

<400> SEQUENCE: 62

```
gctgggtcaa gaatccatgg agatccctca gttatgttct cagggatgtg cttgtaattg    60
ct                                                                   62
```

<210> SEQ ID NO 63
<211> LENGTH: 60
<212> TYPE: DNA
<213> ORGANISM: Artificial Sequence
<220> FEATURE:
<223> OTHER INFORMATION: Synthetic

<400> SEQUENCE: 63

```
gctgggtcaa gaatccatgg atccctcagt tatgttctca gggatgtgct tgtaattgct    60
```

<210> SEQ ID NO 64
<211> LENGTH: 60
<212> TYPE: DNA
<213> ORGANISM: Artificial Sequence
<220> FEATURE:
<223> OTHER INFORMATION: Synthetic

<400> SEQUENCE: 64

```
gctgggtcaa gaatccatgg atccctcagt tatgttctca gggatgtgct tgtaattgct    60
```

<210> SEQ ID NO 65
<211> LENGTH: 1331
<212> TYPE: DNA
<213> ORGANISM: Glycine max

<400> SEQUENCE: 65

```
atggtcatga tttcactctc tctaatctct ccattcattt tgtagttgtc attatcttta    60
gatttttcac tacctggttt aaaattgagg gattgtagtt ctgttggtac atattacaca   120
ttcagcaaaa caactgaaac tcaactgaac ttgtttatac tttgacacag gtctagcaa   180
aggaaacaac aatgggaggt agaggtcgtg tggccaaagt ggaagttcaa gggaagaagc   240
ctctctcaag ggttccaaac acaaagccac cattcactgt tggccaactc aagaaagcaa   300
ttccaccaca ctgctttcag cgctcccctcc tcacttcatt ctcctatgtt gtttatgacc   360
tttcatttgc cttcattttc tacattgcca ccacctactt ccacctcctt cctcaaccct   420
tttccctcat tgcatggcca atctattggg ttctccaagg ttgccttctc actggtgtgt   480
gggtgattgc tcacgagtgt ggtcaccatg ccttcagcaa gtaccaatgg ttgatgatg   540
ttgtgggttt gaccccttcac tcaacacttt tagtccctta tttctcatgg aaaataagcc   600
```

| | | | | |
|---|---|---|---|---|
| atcgccgcca | tcactccaac | acaggttccc | ttgaccgtga | tgaagtgttt | gtcccaaaac | 660 |
| caaaatccaa | agttgcatgg | ttttccaagt | acttaaacaa | ccctctagga | agggctgttt | 720 |
| ctcttctcgt | cacactcaca | atagggtggc | ctatgtattt | agccttcaat | gtctctggta | 780 |
| gaccctatga | tagttttgca | agccactacc | acccttatgc | tcccatatat | tctaaccgtg | 840 |
| agaggcttct | gatctatgtc | tctgatgttg | ctttgttttc | tgtgacttac | tctctctacc | 900 |
| gtgttgcaac | cctgaaaggg | ttggtttggc | tgctatgtgt | ttatggggtg | cctttgctca | 960 |
| ttgtgaacgg | ttttcttgtg | actatcacat | atttgcagca | cacacacttt | gccttgcctc | 1020 |
| attacgattc | atcagaatgg | gactggctga | agggagcttt | ggcaactatg | acagagatt | 1080 |
| atgggattct | gaacaaggtg | tttcatcaca | taactgatac | tcatgtggct | caccatctct | 1140 |
| tctctacaat | gccacattac | catgcaatgg | aggcaaccaa | tgcaatcaag | ccaatattgg | 1200 |
| gtgagtacta | ccaatttgat | gacacaccat | tttacaaggc | actgtggaga | aagcgagag | 1260 |
| agtgcctcta | tgtggagcca | gatgaaggaa | catccgagaa | gggcgtgtat | tggtacagga | 1320 |
| acaagtattg | a | | | | | 1331 |

<210> SEQ ID NO 66
<211> LENGTH: 1324
<212> TYPE: DNA
<213> ORGANISM: Glycine max

<400> SEQUENCE: 66

| | | | | | | |
|---|---|---|---|---|---|---|
| atggtcatga | tttcactctc | tctaatctgt | cacttccctc | cattcatttt | gtacttctca | 60 |
| tatttttcac | ttcctggttg | aaaattgtag | ttctcttggt | acatactagt | attagacatt | 120 |
| cagcaacaac | aactgaactg | aacttcttta | tactttgaca | cagggtctag | caaaggaaac | 180 |
| aataatggga | ggtggaggcc | gtgtggccaa | agttgaaatt | cagcagaaga | agcctctctc | 240 |
| aagggttcca | acacaaagc | caccattcac | tgttggccaa | ctcaagaaag | ccattccacc | 300 |
| gcactgcttt | cagcgttccc | tcctcacttc | attgtcctat | gttgtttatg | accttttcatt | 360 |
| ggctttcatt | ttctacattg | ccaccaccta | cttccacctc | ctccctcacc | ccttttccct | 420 |
| cattgcatgg | ccaatctatt | gggttctcca | aggttgcatt | cttactggcg | tgtgggtgat | 480 |
| tgctcacgag | tgtggtcacc | atgccttcag | caagtaccca | tgggttgatg | atgttatggg | 540 |
| tttgaccgtt | cactcagcac | ttttagtccc | ttatttctca | tggaaaataa | gccatcgccg | 600 |
| ccaccactcc | aacacgggtt | cccttgaccg | tgatgaagtg | tttgtcccaa | aaccaaaatc | 660 |
| caaagttgca | tggtacacca | agtacctgaa | caaccctcta | ggaagggctg | cttctcttct | 720 |
| catcacactc | acaataggg | ggcctttgta | tttagccttc | aatgtctctg | gcagacccta | 780 |
| tgatggtttt | gctagccact | accacccctta | tgctcccata | tattcaaatc | gtgagaggct | 840 |
| tttgatctat | gtctctgatg | ttgctttgtt | ttctgtgact | tacttgctct | accgtgttgc | 900 |
| aactatgaaa | gggttggttt | ggctgctatg | tgtttatggg | gtgccattgc | tcattgtgaa | 960 |
| cggttttctt | gtgaccatca | catatctgca | gcacacacac | tatgccttgc | tcactatga | 1020 |
| ttcatcagaa | tgggattggc | tgaggggtgc | tttggcaact | atggacagag | attatggaat | 1080 |
| tctgaacaag | gtgtttcacc | acataactga | tactcatgtg | gctcaccatc | ttttctctac | 1140 |
| aatgccacat | taccatgcaa | cggaggcaac | caatgcaatg | aagccaatat | tgggtgagta | 1200 |
| ctaccgattt | gatgacacac | cattttacaa | ggcactgtgg | agagaagcaa | gagagtgcct | 1260 |
| ctatgtggag | ccagatgaag | gaacatccga | gaagggcgtg | tattggtaca | ggaacaagta | 1320 |

```
ttga                                                                  1324

<210> SEQ ID NO 67
<211> LENGTH: 3868
<212> TYPE: DNA
<213> ORGANISM: Glycine max

<400> SEQUENCE: 67
atggttaaag acacaaagcc tttagcctat gctgctaata atggatacca aaaggaagct      60
tttgatccca gtgctcctcc accgtttaag attgcagaaa tcagagttgc aataccaaaa     120
cattgctggg tcaagaatcc atggagatcc ctcagttatg ttctcaggga tgtgcttgta     180
attgctgcat tgatggctgc tgcaagtcac ttcaacaact ggcttctctg gctaatctat     240
tggcccattc aaggaacaat gttctgggct ctgtttgttc ttggacatga ttggtaatta     300
attaatttgt tgttactttt tgttataat atgaatctca cacactgctt tgttatgcct      360
acctcatttc atttggcttt agacaactta aatttgagat ctttattatg ttttttgctt     420
atatggtaaa gtgattcatt cttcacattg aattgaacag tggccatgga agcttttcag     480
acagcccttt tctaaatagc ctggtgggac acatcttgca ttcctcaatt cttgtgccat     540
accatggatg gttagttcat cccggctttt ttgtttgtca ttggaagttc ttttattgat     600
tcaattttta tagcgtgttc ggaaacgcgt ttcagaaaat aatgaaatac atcttgaatc     660
tgaaagttat aactttttagc ttcattgtca ttgaaagttc ttttattaat tatattttta    720
ttgcgtgttt ggaatcccat ttgagaaata agaaatcacg tttaaaatgt gaaagttata    780
actattaact tttgactaaa cttgaaaaaa tcacatttttt gatgtggaac caaatctgat   840
ttgagaacca agttgatttt gatggatttt gcaggagaat tagccacaga actcaccatc     900
aaaatcatgg acacattgag aaggatgaat cctgggttcc agtatgtgat taactacttc    960
ctctatagtt attttttgatt caattaaatt tatttattta ataagttcaa gaaaaaagga   1020
atctttatac ttcagataaa gctgttcttg aacatttttt tttgtcatta tcttagttaa    1080
ccgagaagat ttacaagaat ctagacaaca tgacaagact tgttagattc actgtgccat    1140
ttccattgtt tgtgtatcca attatttgg tgagtgcttt tttttttta cttggaagac      1200 tacaacacat tattattatt ataatatggt tcaaatcaat gacttttaat ttctttgtga    1260
tgtgcactcc attttcagtt ctcaagaagc cccggaaagg aaggttctca cttcaatccc    1320
tacagcaatc tgttcccacc cagtgagaga aagggaatag caatatcaac actgtgttgg    1380
gttaccatgt tttctatgct tatctatctc tccttcataa ctagtccagt tctattgctc    1440
aagctctatg gaattccata ttgggtaatt aaattactct tacattactt tttcctcttt    1500 tttttatgg gtcttaacta gtatcacaaa atatttggtt aaaaaatttt aaaaaaatat    1560
ttattatgta aatcataaaa gaacataaaa aaaatgatga ataacataat tttcgtctct    1620
tattaaaaat atttttattt taaatttctt aatcaatata tttagaatct ggttaacatt    1680
ttttgaatat ttcaattctc caattaaaaa tttgaaatag tcaccattaa ttatgtaatt    1740
gtttgaacac gtgcagatat ttgttatgtg gctggacttt gtcacatact tgcatcacca    1800
tggtcatcat cagaaactgc cttggtatcg cggcaaggta acaaaaataa atagaaaata    1860
gtgagtgaac acttaaatgt tagatactac cttcttcttc tttttttttt tttttgagg     1920 ttaatgctag ataatagcta gaaagagaaa gaaagacaaa tataggtaaa aataaataat    1980
ataacctggg aagaagaaaa cataaaaaaa gaaataatag agtctacgta atgtttggat    2040
ttttgagtga atggtgttc acctaccatt actcaaagat tctgttgtct acgtagtgtt     2100
```

```
tggactttgg agtgaaatgg tgttcaccta ccattactca gattctgttg tgtcccttag    2160
ttactgtctt atattcttag ggtatattct ttattttaca tccttttcac atcttacttg    2220
aaaagatttt taattattca ttgaaatatt aacgtgacag ttaaattaaa ataataaaaa    2280
attcgttaaa acttcaaata aataagagtg aaaggatcat cattttctt ctttctttta     2340 ttgcgttatt aatcatgctt ctcttctttt ttttcttcgc tttccaccca tatcaaattc    2400
atgtgaagta tgagaaaatc acgattcaat ggaaagctac aggaactttt tttgttttgt    2460
ttttataatc ggaattaatt tatactccat tttttcacaa taaatgttac ttagtgcctt    2520
aaagataata tttgaaaaat taaaaaaatt attaatacac tgtactacta tataatattt    2580
gacatatatt taacatgatt ttctattgaa aatttgtatt tattatttt taatcaaaac     2640 ccataaggca ttaatttaca agacccattt ttcatttata gctttacctg tgatcattta    2700
tagctttaag ggacttagat gttacaatct taattacaag taaatattta tgaaaaacat    2760
gtgtcttacc ccttaacctt acctcaacaa agaaagtgtg ataagtggca acacacgtgt    2820
tgcttttttg gcccagcaat aacacgtgtt tttgtggtgt acaaaaatgg acaggaatgg    2880
agttatttaa gaggtggtct cacaactgtg gatcgtgact atggttggat caataacatt    2940
caccatgaca ttggcaccca tgttattcac catcttttcc ctcaaattcc tcattatcac    3000
ctcgttgaag cggtatattt tactattatt actcacctaa aaagaatgca attagtacat    3060
ttgttttatc tcttggaagt tagtcatttt cagttgcatg attgtaatgt tctctctatt    3120
tttaaaccat gttttcacac ctacttcgtt taaaataaga atgtggatac tattctaatt    3180
tctattaact tcttttaaaa ataatgtaa aactagtatt aaaaaagagg aaatagatta    3240
cactctacta atactaatag tataaaaaaa attacattgt tatttatca caaataatta     3300 tatataatta attttttacaa tcattatctt aaaagtcatg tatgatatac agttttaca    3360 tgctttggta cttattgtaa agttagtgat ttattcatta tttatgttat ataattggca    3420
taaatatcat gtaaccagct cactatacta taatgggaac ttggtggtga aaggggttta    3480
caaccctctt ttctaggtgt aggtgctttg atacttctgg tccctttta tatcaatata     3540 aattatattt tgctgataaa aaaaacatta ttaatatata atcattaact tctttaaaaa    3600
ccgtacctaa aacttatat tattaaaaag aagattgaga tcagcaaaag aaaaaaaaat     3660
taacagtcat ttgaattcac tgcagacaca agcagcaaaa tcgttcttg gagagtatta    3720 ccgtgagcca gaaagatctg caccattacc atttcatcta ataaagtatt taattcagag    3780
tatgagacaa gaccacttcg taagtgacac tggagatgtg gtttattatc agactgattc    3840
tctgcacctt cactcgcacc gagactga                                       3868
```

<210> SEQ ID NO 68
<211> LENGTH: 3896
<212> TYPE: DNA
<213> ORGANISM: Glycine max

<400> SEQUENCE: 68

```
atggttaaag acacaaagcc tttagcctat gctgccaata atggatacca acaaaagggt      60
tcttcttttg attttgatcc tagcgctcct ccaccgttta agattgcaga aatcagagct    120
tcaataccaa aacattgctg ggtcaagaat ccatggagat ccctcagtta tgttctcagg    180
gatgtgcttg taattgctgc attggtggct gcagcaattc acttcgacaa ctggcttctc    240
tggctaatct attgccccat tcaaggcaca atgttctggg ctctctttgt tcttggacat    300
```

```
gattggtaat aattttttgtg tttcttactc tttttttttt tttttttgttt atgatatgaa    360 tctcacacat tgttctgtta tgtcatttct tcttcatttg gctttagaca acttaaattt    420
gagatcttta ttatgttttt gcttatatgg taaagtgatt cttcattatt tcattcttca    480
ttgattgaat tgaacagtgg ccatggaagc ttttcagata gccctttgct gaatagcctg    540
gtgggacaca tcttgcattc ctcaattctt gtgccatacc atggatggtt agttcatact    600
ggcttttttg tttgttcatt tgtcattgaa aaaaaatctt ttgttgattc aattattttt    660
atagtgtgtt tggaagcccg tttgagaaaa taagaaatcg catctggaat gtgaaagtta    720
taactattta gcttcatctg tcgttgcaag ttcttttatt ggttaaattt ttatagcgtg    780
ctaggaaacc cattcgagaa aataagaaat cacatctgga atgtgaaagt tataactgtt    840
agcttctgag taaacgtgga aaaccacat tttggatttg gaaccaaatt ttatttgata    900
aatgacaacc aaattgattt tgatggattt tgcaggagaa ttagccacag aactcaccat    960 caaaccatg gacacattga aaggatgag tcatgggttc cagtatgtga ttaattgctt    1020
ctcctatagt tgttcttgat tcaattacat tttatttatt tggtaggtcc aagaaaaaag    1080
ggaatcttta tgcttcctga ggctgttctt gaacatggct cttttttatg tgtcattatc    1140
ttagttaaca gagaagattt acaagaatct agacagcatg acaagactca ttagattcac    1200
tgtgccattt ccattgtttg tgtatccaat ttatttggtg agtgattttt tgacttggaa    1260
gacaacaaca cattattatt ataatatggt tcaaaacaat gacttttttct ttatgatgtg    1320 aactccattt tttagttttc aagaagcccc ggaaggaag gctctcactt caatccctac    1380
agcaatctgt ttccacccag tgagagaaaa ggaatagcaa tatcaacact gtgttgggct    1440
accatgtttt ctctgcttat ctatctctca ttcataacta gtccacttct agtgctcaag    1500
ctctatggaa ttccatattg ggtaactaaa ttactcctac attgttactt tttcctcctt    1560
tttttattta tttcaattct ccaattggaa atttgaaata gttaccataa ttatgtaatt    1620
gtttgatcat gtgcagatat ttgttatgtg gctggacttt gtcacatact tgcatcacca    1680
tggtcaccac cagaaactgc cttggtaccg cggcaaggta acaaaaataa atagaaaata    1740
gtgggtgaac acttaaatgc gagatagtaa tacctaaaaa aagaaaaaaa tataggtata    1800
ataaataata taactttcaa aataaaaaga aatcatagag tctagcgtag tgtttggagt    1860
gaaatgatgt tcacctacca ttactcaaag attttgttgt gtcccttagt tcattcttat    1920
tattttacat atcttacttg aaaagacttt ttaattattc attgagatct taaagtgact    1980
gttaaattaa aataaaaaac aagtttgtta aaacttcaaa taaataagag tgaagggagt    2040
gtcatttgtc ttctttcttt tattgcgtta ttaatcacgt ttctcttctc tttttttttt    2100
tttcttctct gctttccacc cattatcaag ttcatgtgaa gcagtggcgg atctatgtaa    2160
atgagtgggg ggcaattgca cccacaagat tttattttt atttgtacag gaataataaa    2220
ataaaacttt gcccccataa aaaataaata ttttttctta aaataatgca aaataaatat    2280
aagaaataaa aagagaataa attattatta atttattat tttgtacttt ttatttagtt    2340
tttttagcgg ttagattttt ttttcatgac attatgtaat cttttaaaag catgtaatat    2400 ttttatttg tgaaaataaa tataaatgat catattagtc tcagaatgta taaactaata    2460 ataatttttat cactaaaaga aattctaatt tagtccataa ataagtaaaa caagtgacaa    2520 ttatattta tatttactta atgtgaaata atacttgaac attataataa aacttaatga    2580
caggagatat tacatagtgc cataaagata tttttaaaaaa taaaatcatt aatacactgt    2640
actactatat aatattcgat atatattttt aacatgattc tcaatagaaa aattgtattg    2700
```

-continued

```
attatatttt attagacatg aatttacaag ccccgttttt catttatagc tcttacctgt    2760
gatctattgt tttgcttcgc tgttttttgtt ggtcaaggga cttagatgtc acaatattaa   2820
tactagaagt aaatatttat gaaaacatgt accttacctc aacaaagaaa gtgtggtaag    2880
tggcaacaca cgtgttgcat ttttggccca gcaataacac gtgttttttgt ggtgtactaa   2940 aatggacagg aatggagtta tttaagaggt ggcctcacca ctgtggatcg tgactatggt    3000
tggatcaata acattcacca tgacattggc acccatgtta tccaccatct tttcccccaa    3060
attcctcatt atcacctcgt tgaagcggta cattttattg cttattcacc taaaaacaat    3120
acaattagta catttgtttt atctcttgga agttagtcat tttcagttgc atgattctaa    3180
tgctctctcc attcttaaat catgttttca cacccacttc atttaaaata agaacgtggg    3240
tgttatttta atttctattc actaacatga gaaattaact tatttcaagt aataattttta   3300 aaatatttttt atgctattat tttattacaa ataattatgt atattaagtt tattgatttt    3360
ataataatta tattaaaatt atatcgatat taattttttga ttcactgata gtgttttata    3420
ttgttagtac tgtgcattta ttttaaaatt ggcataaata atatatgtaa ccagctcact    3480
atactatact gggagcttgg tggtgaaagg ggttcccaac cctccttttct aggtgtacat    3540 gctttgatac ttctggtacc ttcttatatc aatataaatt atattttgct gataaaaaaa    3600
catggttaac cattaaattc tttttttttaaa aaaaaaactg tatctaaact ttgtattatt   3660
aaaaagaagt ctgagattaa caataaacta acactcattt gaattcactg cagacacaag    3720
cagcaaaacc agttcttgga gattactacc gtgagccaga aagatctgcg ccattaccat    3780
ttcatctaat aaagtattta attcagagta tgagacaaga ccacttcgta agtgacactg    3840
gagatgttgt ttattatcag actgattctc tgctcctcca ctcgcaacga gactga        3896
```

<210> SEQ ID NO 69
<211> LENGTH: 1164
<212> TYPE: DNA
<213> ORGANISM: Glycine max

<400> SEQUENCE: 69

```
atgggtctag caaaggaaac aacaatggga ggtagaggtc gtgtggccaa agtggaagtt     60
caagggaaga agcctctctc aagggttcca aacacaaagc caccattcac tgttggccaa    120
ctcaagaaag caattccacc acactgcttt cagcgctccc tcctcacttc attctcctat    180
gttgtttatg acctttcatt tgccttcatt ttctacattg ccaccaccta cttccacctc    240
cttcctcaac cctttttccct cattgcatgg ccaatctatt gggttctcca aggttgcctt    300
ctcactggtg tgtgggtgat tgctcacgag tgtggtcacc atgccttcag caagtaccaa    360
tgggttgatg atgttgtggg tttgaccctt cactcaacac ttttagtccc ttatttctca    420
tggaaaataa gccatcgccg ccatcactcc aacacaggtt cccttgaccg tgatgaagtg    480
tttgtcccaa aaccaaaatc caaagttgca tggttttcca agtacttaaa caaccctcta    540
ggaagggctg tttctcttct cgtcacactc acaatagggt ggcctatgta tttagccttc    600
aatgtctctg gtagacccta tgatagtttt gcaagccact accacccttta tgctcccata    660 tattctaacc gtgagaggct tctgatctat gtctctgatg ttgctttgtt ttctgtgact    720
tactctctct accgtgttgc aaccctgaaa gggttggttt ggctgctatg tgtttatggg    780
gtgcctttgc tcattgtgaa cggttttctt gtgactatca catatttgca gcacacacac    840
tttgccttgc ctcattacga ttcatcagaa tgggactggc tgaagggagc tttggcaact    900
```

```
atggacagag attatgggat tctgaacaag gtgtttcatc acataactga tactcatgtg    960
gctcaccatc tcttctctac aatgccacat taccatgcaa tggaggcaac caatgcaatc   1020
aagccaatat tgggtgagta ctaccaattt gatgacacac cattttacaa ggcactgtgg   1080
agagaagcga gagagtgcct ctatgtggag ccagatgaag aacatccga aagggcgtg    1140 tattggtaca ggaacaagta ttga                                          1164
```

<210> SEQ ID NO 70
<211> LENGTH: 386
<212> TYPE: PRT
<213> ORGANISM: Glycine max

<400> SEQUENCE: 70

```
Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
    290                 295                 300

Tyr Gly Ile Leu Asn Lys Val Phe His His Ile Thr Asp Thr Val Ala
305                 310                 315                 320

His His Leu Phe Ser Thr Met Pro His Tyr His Ala Met Glu Ala Thr
```

325                 330                 335
Asn Ala Ile Lys Pro Ile Leu Gly Glu Tyr Tyr Gln Phe Asp Asp Thr
                340                 345                 350

Pro Phe Tyr Lys Ala Leu Trp Arg Glu Ala Arg Glu Cys Leu Tyr Val
            355                 360                 365

Glu Pro Asp Glu Gly Thr Ser Glu Lys Gly Val Tyr Trp Tyr Arg Asn
        370                 375                 380

Lys Tyr
385

<210> SEQ ID NO 71
<211> LENGTH: 1164
<212> TYPE: DNA
<213> ORGANISM: Glycine max

<400> SEQUENCE: 71
atgggtctag caaaggaaac aataatggga ggtggaggcc gtgtggccaa agttgaaatt      60
cagcagaaga agcctctctc aagggttcca aacacaaagc caccattcac tgttggccaa     120
ctcaagaaag ccattccacc gcactgcttt cagcgttccc tcctcacttc attgtcctat     180
gttgtttatg acctttcatt ggctttcatt ttctacattg ccaccaccta cttccacctc     240
ctccctcacc ccttttccct cattgcatgg ccaatctatt gggttctcca aggttgcatt     300
cttactggcg tgtgggtgat tgctcacgag tgtggtcacc atgccttcag caagtaccca     360
tgggttgatg atgttatggg tttgaccgtt cactcagcac ttttagtccc ttatttctca     420
tggaaaataa gccatcgccg ccaccactcc aacacgggtt cccttgaccg tgatgaagtg     480
tttgtcccaa aaccaaaatc caaagttgca tggtacacca agtacctgaa caaccctcta     540
ggaagggctg cttctcttct catcacactc acaataggg t ggcctttgta tttagccttc     600
aatgtctctg gcagacccta tgatggtttt gctagccact accacccttat gctcccata      660 tattcaaatc gtgagaggct tttgatctat gtctctgatg ttgctttgtt ttctgtgact     720
tacttgctct accgtgttgc aactatgaaa gggttggttt ggctgctatg tgtttatggg     780
gtgccattgc tcattgtgaa cggttttctt gtgaccatca catatctgca gcacacacac     840
tatgccttgc ctcactatga ttcatcagaa tgggattggc tgagggggtgc tttggcaact     900 atggacagag attatggaat tctgaacaag gtgtttcacc acataactga tactcatgtg     960
gctcaccatc ttttctctac aatgccacat taccatgcaa cggaggcaac caatgcaatg    1020
aagccaaatg tgggtgagta ctaccgattt gatgacacac cattttacaa ggcactgtgg    1080
agagaagcaa gagagtgcct ctatgtggag ccagatgaag gaacatccga agggcgtgg     1140 tattggtaca ggaacaagta ttga                                            1164

<210> SEQ ID NO 72
<211> LENGTH: 386
<212> TYPE: PRT
<213> ORGANISM: Glycine max

<400> SEQUENCE: 72

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

```
            Cys Phe Gln Arg Ser Leu Leu Thr Ser Leu Ser Tyr Val Val Tyr Asp
             50                  55                  60

Leu Ser Leu Ala Phe Ile Phe Tyr Ile Ala Thr Thr Tyr Phe His Leu
         65                  70                  75                  80

Leu Pro His Pro Phe Ser Leu Ile Ala Trp Pro Ile Tyr Trp Val Leu
                             85                  90                  95

Gln Gly Cys Ile Leu Thr Gly Val Trp Val Ile Ala His Glu Cys Gly
                        100                 105                 110

His His Ala Phe Ser Lys Tyr Pro Trp Val Asp Val Met Gly Leu
                    115                 120                 125

Thr Val His Ser Ala Leu Leu Val Pro Tyr Phe Ser Trp Lys Ile Ser
                130                 135                 140

His Arg Arg His His Ser Asn Thr Gly Ser Leu Asp Arg Asp Val Phe
        145                 150                 155                 160

Val Pro Lys Pro Lys Ser Lys Val Ala Trp Tyr Thr Lys Tyr Leu Asn
                            165                 170                 175

Asn Pro Leu Gly Arg Ala Ala Ser Leu Leu Ile Thr Leu Thr Ile Gly
                        180                 185                 190

Trp Pro Leu Tyr Leu Ala Phe Asn Val Ser Gly Arg Pro Tyr Asp Gly
                    195                 200                 205

Phe Ala Ser His Tyr His Pro Tyr Ala Pro Ile Tyr Ser Asn Arg Glu
                210                 215                 220

Arg Leu Leu Ile Tyr Val Ser Asp Val Ala Leu Phe Ser Val Thr Tyr
        225                 230                 235                 240

Leu Leu Tyr Arg Val Ala Thr Met Lys Gly Leu Val Trp Leu Leu Cys
                            245                 250                 255

Val Tyr Gly Val Pro Leu Leu Ile Val Asn Gly Phe Leu Val Thr Ile
                        260                 265                 270

Thr Tyr Leu Gln His Thr His Tyr Ala Leu Pro His Tyr Asp Ser Ser
                    275                 280                 285

Glu Trp Asp Trp Leu Arg Gly Ala Leu Ala Thr Met Asp Arg Asp Tyr
                290                 295                 300

Gly Ile Leu Asn Lys Val Phe His His Ile Thr Asp Thr His Val Ala
        305                 310                 315                 320

His His Leu Phe Ser Thr Met Pro His Tyr His Ala Thr Glu Ala Thr
                            325                 330                 335

Asn Ala Met Lys Pro Ile Leu Gly Glu Tyr Tyr Arg Phe Asp Asp Thr
                        340                 345                 350

Pro Phe Tyr Lys Ala Leu Trp Arg Glu Ala Arg Glu Cys Leu Tyr Val
                    355                 360                 365

Glu Pro Asp Glu Gly Thr Ser Glu Lys Gly Val Tyr Trp Tyr Arg Asn
                370                 375                 380

Lys Tyr
            385

<210> SEQ ID NO 73
            <211> LENGTH: 1131
            <212> TYPE: DNA
            <213> ORGANISM: Glycine max

<400> SEQUENCE: 73
atggttaaag acacaaagcc tttagcctat gctgctaata atggatacca aaaggaagct        60
tttgatccca gtgctcctcc accgtttaag attgcagaaa tcagagttgc aataccaaaa       120
cattgctggg tcaagaatcc atggagatcc ctcagttatg ttctcaggga tgtgcttgta       180
```

```
attgctgcat tgatggctgc tgcaagtcac ttcaacaact ggcttctctg ctaatctat      240 tggcccattc aaggaacaat gttctgggct ctgtttgttc ttggacatga ttgtggccat     300
ggaagctttt cagacagccc ttttctaaat agcctggtgg acacatcttt gcattcctca    360
attcttgtgc ataccatgg atggagaatt agccacagaa ctcaccatca aaatcatgga     420
cacattgaga aggatgaatc ctgggttcca ttaaccgaga agatttacaa gaatctagac    480
aacatgacaa gacttgttag attcactgtg ccatttccat tgtttgtgta tccaatttat    540
ttgttctcaa gaagccccgg aaaggaaggt tctcacttca atccctacag caatctgttc    600
ccacccagtg agagaaaggg aatagcaata tcaacactgt gttgggttac catgttttct   660
atgcttatct atctctcctt cataactagt ccagttctat tgctcaagct ctatggaatt    720
ccatattgga tatttgttat gtggctggac tttgtcacat acttgcatca ccatggtcat    780
catcagaaac tgccttggta tcgcggcaag gaatggagtt atttaagagg tggtctcaca    840
actgtggatc gtgactatgg ttggatcaat aacattcacc atgacattgg cacccatgtt    900
attcaccatc tttttccctca aattcctcat tatcacctcg ttgaagcgac acaagcagca   960
aaatcagttc ttggagagta ttaccgtgag ccagaaagat ctgcaccatt accatttcat   1020
ctaataaagt atttaattca gagtatgaga caagaccact tcgtaagtga cactggagat   1080
gtggtttatt atcagactga ttctctgcac cttcactcgc accgagactg a             1131
```

<210> SEQ ID NO 74
<211> LENGTH: 376
<212> TYPE: PRT
<213> ORGANISM: Glycine max

<400> SEQUENCE: 74

```
Met Val Lys Asp Thr Lys Pro Leu Ala Tyr Ala Ala Asn Asn Gly Tyr
1               5                   10                  15

Gln Lys Glu Ala Phe Asp Pro Ser Ala Pro Pro Phe Lys Ile Ala
            20                  25                  30

Glu Ile Arg Val Ala Ile Pro Lys His Cys Trp Val Lys Asn Pro Trp
        35                  40                  45

Arg Ser Leu Ser Tyr Val Leu Arg Asp Val Leu Val Ile Ala Ala Leu
    50                  55                  60

Met Ala Ala Ala Ser His Phe Asn Asn Trp Leu Leu Trp Leu Ile Tyr
65                  70                  75                  80

Trp Pro Ile Gln Gly Thr Met Phe Trp Ala Leu Phe Val Leu Gly His
                85                  90                  95

Asp Cys Gly His Gly Ser Phe Ser Asp Ser Pro Phe Leu Asn Ser Leu
            100                 105                 110

Val Gly His Ile Leu His Ser Ser Ile Leu Val Pro Tyr His Gly Trp
        115                 120                 125

Arg Ile Ser His Arg Thr His His Gln Asn His Gly His Ile Glu Lys
    130                 135                 140

Asp Glu Ser Trp Val Pro Leu Thr Glu Lys Ile Tyr Lys Asn Leu Asp
145                 150                 155                 160

Asn Met Thr Arg Leu Val Arg Phe Thr Val Pro Phe Pro Leu Phe Val
                165                 170                 175

Tyr Pro Ile Tyr Leu Phe Ser Arg Ser Pro Gly Lys Glu Gly Ser His
            180                 185                 190

Phe Asn Pro Tyr Ser Asn Leu Phe Pro Pro Ser Glu Arg Lys Gly Ile
        195                 200                 205
```

```
Ala Ile Ser Thr Leu Cys Trp Val Thr Met Phe Ser Met Leu Ile Tyr
    210                 215                 220
Leu Ser Phe Ile Thr Ser Pro Val Leu Leu Lys Leu Tyr Gly Ile
225                 230                 235                 240
Pro Tyr Trp Ile Phe Val Met Trp Leu Asp Phe Val Thr Tyr Leu His
                245                 250                 255
His His Gly His His Gln Lys Leu Pro Trp Tyr Arg Gly Lys Glu Trp
            260                 265                 270
Ser Tyr Leu Arg Gly Gly Leu Thr Thr Val Asp Arg Asp Tyr Gly Trp
        275                 280                 285
Ile Asn Asn Ile His His Asp Ile Gly Thr His Val Ile His His Leu
    290                 295                 300
Phe Pro Gln Ile Pro His Tyr His Leu Val Glu Ala Thr Gln Ala Ala
305                 310                 315                 320
Lys Ser Val Leu Gly Glu Tyr Tyr Arg Glu Pro Glu Arg Ser Ala Pro
                325                 330                 335
Leu Pro Phe His Leu Ile Lys Tyr Leu Ile Gln Ser Met Arg Gln Asp
                340                 345                 350
His Phe Val Ser Asp Thr Gly Asp Val Val Tyr Gln Thr Asp Ser
            355                 360                 365
Leu His Leu His Ser His Arg Asp
    370                 375

<210> SEQ ID NO 75
<211> LENGTH: 1143
<212> TYPE: DNA
<213> ORGANISM: Glycine max

<400> SEQUENCE: 75
atggttaaag acacaaagcc tttagcctat gctgccaata tggatacca acaaaagggt     60 tcttcttttg attttgatcc tagcgctcct ccaccgttta agattgcaga atcagagct    120 tcaataccaa acattgctg ggtcaagaat ccatggagat ccctcagtta tgttctcagg    180
gatgtgcttt taattgctgc attggtggct gcagcaattc acttcgacaa ctggcttctc    240
tggctaatct attgccccat tcaaggcaca atgttctggg ctctctttgt tcttggacat    300
gattgtggcc atgaagcttt tcagatagc cctttgctga atagcctggt gggacacatc    360
ttgcattcct caattcttgt gccataccat ggatggagaa ttagccacag aactcaccat    420
caaaaccatg acacattga aaggatgag tcatgggttc cattaacaga aagatttac     480 aagaatctag acagcatgac aagactcatt agattcactg tgccatttcc attgtttgtg    540
tatccaattt atttgttttc aagaagcccc ggaaaggaag ctctcacctt caatccctac    600
agcaatctgt ttccacccag tgagagaaaa ggaatagcaa tcaacact gtgttgggct    660 accatgtttt ctctgcttat ctatctctca ttcataacta gtccacttct agtgctcaag    720
ctctatggaa ttccatattg gatatttgtt atgtggctgg actttgtcac atacttgcat    780
caccatggtc accaccagaa actgccttgg taccgcggca aggaatggag ttatttaaga    840
ggtggcctca ccactgtgga tcgtgactat ggttggatca taacattca ccatgacatt    900 ggcacccatg ttatccacca tcttttcccc caaattcctc attatcacct cgttgaagcg    960
acacaagcag caaaaccagt tcttggagat tactaccgtg agccagaaag atctgcgcca   1020
ttaccatttc atctaataaa gtatttaatt cagagtatga caagacca cttcgtaagt   1080 gacactggag atgttgttta ttatcagact gattctctgc tcctccactc gcaacgagac   1140
``` tga                                                                1143

<210> SEQ ID NO 76
<211> LENGTH: 380
<212> TYPE: PRT
<213> ORGANISM: Glycine max

<400> SEQUENCE: 76

Met Val Lys Asp Thr Lys Pro Leu Ala Tyr Ala Ala Asn Asn Gly Tyr
1               5                   10                  15

Gln Gln Lys Gly Ser Ser Phe Asp Phe Asp Pro Ser Ala Pro Pro Pro
            20                  25                  30

Phe Lys Ile Ala Glu Ile Arg Ala Ser Ile Pro Lys His Cys Trp Val
        35                  40                  45

Lys Asn Pro Trp Arg Ser Leu Ser Tyr Val Leu Arg Asp Val Leu Val
    50                  55                  60

Ile Ala Ala Leu Val Ala Ala Ile His Phe Asp Asn Trp Leu Leu
65                  70                  75                  80

Trp Leu Ile Tyr Cys Pro Ile Gln Gly Thr Met Phe Trp Ala Leu Phe
                85                  90                  95

Val Leu Gly His Asp Cys Gly His Gly Ser Phe Ser Asp Ser Pro Leu
            100                 105                 110

Leu Asn Ser Leu Val Gly His Ile Leu His Ser Ser Ile Leu Val Pro
        115                 120                 125

Tyr His Gly Trp Arg Ile Ser His Arg Thr His His Gln Asn His Gly
    130                 135                 140

His Ile Glu Lys Asp Glu Ser Trp Val Pro Leu Thr Glu Lys Ile Tyr
145                 150                 155                 160

Lys Asn Leu Asp Ser Met Thr Arg Leu Ile Arg Phe Thr Val Pro Phe
                165                 170                 175

Pro Leu Phe Val Tyr Pro Ile Tyr Leu Phe Ser Arg Ser Pro Gly Lys
            180                 185                 190

Glu Gly Ser His Phe Asn Pro Tyr Ser Asn Leu Phe Pro Pro Ser Glu
        195                 200                 205

Arg Lys Gly Ile Ala Ile Ser Thr Leu Cys Trp Ala Thr Met Phe Ser
    210                 215                 220

Leu Leu Ile Tyr Leu Ser Phe Ile Thr Ser Pro Leu Leu Val Leu Lys
225                 230                 235                 240

Leu Tyr Gly Ile Pro Tyr Trp Ile Phe Val Met Trp Leu Asp Phe Val
                245                 250                 255

Thr Tyr Leu His His His Gly His His Gln Lys Leu Pro Trp Tyr Arg
            260                 265                 270

Gly Lys Glu Trp Ser Tyr Leu Arg Gly Gly Leu Thr Thr Val Asp Arg
        275                 280                 285

Asp Tyr Gly Trp Ile Asn Asn Ile His Asp Ile Gly Thr His Val
    290                 295                 300

Ile His His Leu Phe Pro Gln Ile Pro His Tyr His Leu Val Glu Ala
305                 310                 315                 320

Thr Gln Ala Ala Lys Pro Val Leu Gly Asp Tyr Tyr Arg Glu Pro Glu
                325                 330                 335

Arg Ser Ala Pro Leu Pro Phe His Leu Ile Lys Tyr Leu Ile Gln Ser
            340                 345                 350

Met Arg Gln Asp His Phe Val Ser Asp Thr Gly Asp Val Val Tyr Tyr
        355                 360                 365

Gln Thr Asp Ser Leu Leu Leu His Ser Gln Arg Asp
    370                 375                 380

<210> SEQ ID NO 77
<211> LENGTH: 49
<212> TYPE: DNA
<213> ORGANISM: Artificial Sequence
<220> FEATURE:
<223> OTHER INFORMATION: Synthetic

<400> SEQUENCE: 77
gtggaagttc aagggaagaa gcctcaaaca caaagccacc attcactgt            49

<210> SEQ ID NO 78
<211> LENGTH: 58
<212> TYPE: DNA
<213> ORGANISM: Artificial Sequence
<220> FEATURE:
<223> OTHER INFORMATION: Synthetic

<400> SEQUENCE: 78
gctgggtcaa gaatccatgg acctcagtta tgttctcagg gatgtgcttg taattgct      58

<210> SEQ ID NO 79
<211> LENGTH: 60
<212> TYPE: DNA
<213> ORGANISM: Artificial Sequence
<220> FEATURE:
<223> OTHER INFORMATION: Synthetic

<400> SEQUENCE: 79
gctgggtcaa gaatccatgg atccctcagt tatgttctca gggatgtgct tgtaattgct    60

<210> SEQ ID NO 80
<211> LENGTH: 23
<212> TYPE: DNA
<213> ORGANISM: Artificial Sequence
<220> FEATURE:
<223> OTHER INFORMATION: Synthetic

<400> SEQUENCE: 80
ttcaagttgg gctttttcag aag                                        23

<210> SEQ ID NO 81
<211> LENGTH: 22
<212> TYPE: DNA
<213> ORGANISM: Artificial Sequence
<220> FEATURE:
<223> OTHER INFORMATION: Synthetic

<400> SEQUENCE: 81
tctccttggt gctctcatca ca                                         22

<210> SEQ ID NO 82
<211> LENGTH: 15
<212> TYPE: DNA
<213> ORGANISM: Artificial Sequence
<220> FEATURE:
<223> OTHER INFORMATION: Synthetic

<400> SEQUENCE: 82
ctgcagcaga accaa                                                 15

<210> SEQ ID NO 83
<211> LENGTH: 62

<212> TYPE: DNA
<213> ORGANISM: Glycine max

<400> SEQUENCE: 83
gtggaagttc aagggaagaa gcctctctca agggttccaa acacaaagcc accattcact    60
gt                                                                  62

<210> SEQ ID NO 84
<211> LENGTH: 55
<212> TYPE: DNA
<213> ORGANISM: Artificial Sequence
<220> FEATURE:
<223> OTHER INFORMATION: Synthetic

<400> SEQUENCE: 84
gtggaagttc aagggaagaa gcctctcttc aaacacaaa gccaccattc actgt          55

<210> SEQ ID NO 85
<211> LENGTH: 60
<212> TYPE: DNA
<213> ORGANISM: Artificial Sequence
<220> FEATURE:
<223> OTHER INFORMATION: Synthetic

<400> SEQUENCE: 85
gtggaagttc aagggaagaa gcctctctag ggttccaaac acaaagccac cattcactgt    60

<210> SEQ ID NO 86
<211> LENGTH: 57
<212> TYPE: DNA
<213> ORGANISM: Artificial Sequence
<220> FEATURE:
<223> OTHER INFORMATION: Synthetic

<400> SEQUENCE: 86
gtggaagttc aagggaagaa gcctctctgt tccaaacaca aagccaccat tcactgt       57

<210> SEQ ID NO 87
<211> LENGTH: 51
<212> TYPE: DNA
<213> ORGANISM: Artificial Sequence
<220> FEATURE:
<223> OTHER INFORMATION: Synthetic

<400> SEQUENCE: 87
gtggaagttc aagggaagaa gcctctcaaa cacaaagcca ccattcactg t              51

<210> SEQ ID NO 88
<211> LENGTH: 54
<212> TYPE: DNA
<213> ORGANISM: Artificial Sequence
<220> FEATURE:
<223> OTHER INFORMATION: Synthetic

<400> SEQUENCE: 88
gtggaagttc aagggaagaa gcctcgttcc aaacacaaag ccaccattca ctgt           54

<210> SEQ ID NO 89
<211> LENGTH: 58
<212> TYPE: DNA
<213> ORGANISM: Artificial Sequence
<220> FEATURE:
<223> OTHER INFORMATION: Synthetic

<400> SEQUENCE: 89
gtggaagttc aagggaagaa gcctctctgg ttccaaacac aaagccacca ttcactgt    58

<210> SEQ ID NO 90
<211> LENGTH: 54
<212> TYPE: DNA
<213> ORGANISM: Artificial Sequence
<220> FEATURE:
<223> OTHER INFORMATION: Synthetic

<400> SEQUENCE: 90
gtggaagttc aagggaagaa gcctctctcc aaacacaaag ccaccattca ctgt    54

<210> SEQ ID NO 91
<211> LENGTH: 55
<212> TYPE: DNA
<213> ORGANISM: Artificial Sequence
<220> FEATURE:
<223> OTHER INFORMATION: Synthetic

<400> SEQUENCE: 91
gtggaagttc aagggaagaa gcctctgttc caaacacaaa gccaccattc actgt    55

<210> SEQ ID NO 92
<211> LENGTH: 62
<212> TYPE: DNA
<213> ORGANISM: Glycine max

<400> SEQUENCE: 92
gttgaaattc agcagaagaa gcctctctca agggttccaa acacaaagcc accattcact    60
gt    62

<210> SEQ ID NO 93
<211> LENGTH: 55
<212> TYPE: DNA
<213> ORGANISM: Artificial Sequence
<220> FEATURE:
<223> OTHER INFORMATION: Synthetic

<400> SEQUENCE: 93
gttgaaattc agcagaagaa gcctctcttc caaacacaaa gccaccattc actgt    55

<210> SEQ ID NO 94
<211> LENGTH: 46
<212> TYPE: DNA
<213> ORGANISM: Artificial Sequence
<220> FEATURE:
<223> OTHER INFORMATION: Synthetic

<400> SEQUENCE: 94
gttgaaattc agcagaagaa gccaacacaa agccaccatt cactgt    46

<210> SEQ ID NO 95
<211> LENGTH: 57
<212> TYPE: DNA
<213> ORGANISM: Artificial Sequence
<220> FEATURE:
<223> OTHER INFORMATION: Synthetic

<400> SEQUENCE: 95
gttgaaattc agcagaagaa gcctctctgt tccaaacaca aagccaccat tcactgt    57

<210> SEQ ID NO 96
<211> LENGTH: 58
<212> TYPE: DNA
<213> ORGANISM: Artificial Sequence

```
<220> FEATURE:
<223> OTHER INFORMATION: Synthetic

<400> SEQUENCE: 96
gttgaaattc agcagaagaa gcctctctgg ttccaaacac aaagccacca ttcactgt     58

<210> SEQ ID NO 97
<211> LENGTH: 57
<212> TYPE: DNA
<213> ORGANISM: Artificial Sequence
<220> FEATURE:
<223> OTHER INFORMATION: Synthetic

<400> SEQUENCE: 97
gttgaaattc agcagaagaa gcctctcggt tccaaacaca aagccaccat tcactgt      57

<210> SEQ ID NO 98
<211> LENGTH: 54
<212> TYPE: DNA
<213> ORGANISM: Artificial Sequence
<220> FEATURE:
<223> OTHER INFORMATION: Synthetic

<400> SEQUENCE: 98
gttgaaattc agcagaagaa gcctctttcc aaacacaaag ccaccattca ctgt         54

<210> SEQ ID NO 99
<211> LENGTH: 60
<212> TYPE: DNA
<213> ORGANISM: Artificial Sequence
<220> FEATURE:
<223> OTHER INFORMATION: Synthetic

<400> SEQUENCE: 99
gttgaaattc agcagaagaa gcctctcaag ggttccaaac acaaagccac cattcactgt   60

<210> SEQ ID NO 100
<211> LENGTH: 55
<212> TYPE: DNA
<213> ORGANISM: Artificial Sequence
<220> FEATURE:
<223> OTHER INFORMATION: Synthetic

<400> SEQUENCE: 100
gttgaaattc agcagaagaa gccagggttc caaacacaaa gccaccattc actgt        55

<210> SEQ ID NO 101
<211> LENGTH: 62
<212> TYPE: DNA
<213> ORGANISM: Glycine max

<400> SEQUENCE: 101
gtggaagttc aagggaagaa gcctctctca agggttccaa acacaaagcc accattcact   60
gt                                                                  62

<210> SEQ ID NO 102
<211> LENGTH: 60
<212> TYPE: DNA
<213> ORGANISM: Artificial Sequence
<220> FEATURE:
<223> OTHER INFORMATION: Synthetic

<400> SEQUENCE: 102
gtggaagttc aagggaagaa gcctctctag ggttccaaac acaaagccac cattcactgt   60
```

```
<210> SEQ ID NO 103
<211> LENGTH: 54
<212> TYPE: DNA
<213> ORGANISM: Artificial Sequence
<220> FEATURE:
<223> OTHER INFORMATION: Synthetic

<400> SEQUENCE: 103
gtggaagttc aagggaagaa gcctctctcc aaacacaaag ccaccattca ctgt        54

<210> SEQ ID NO 104
<211> LENGTH: 57
<212> TYPE: DNA
<213> ORGANISM: Artificial Sequence
<220> FEATURE:
<223> OTHER INFORMATION: Synthetic

<400> SEQUENCE: 104
gtggaagttc aagggaagaa gcctctctgt tccaaacaca agccaccat tcactgt     57

<210> SEQ ID NO 105
<211> LENGTH: 55
<212> TYPE: DNA
<213> ORGANISM: Artificial Sequence
<220> FEATURE:
<223> OTHER INFORMATION: Synthetic

<400> SEQUENCE: 105
gtggaagttc aagggaagaa gcctctcttc caaacacaaa gccaccattc actgt       55

<210> SEQ ID NO 106
<211> LENGTH: 54
<212> TYPE: DNA
<213> ORGANISM: Artificial Sequence
<220> FEATURE:
<223> OTHER INFORMATION: Synthetic

<400> SEQUENCE: 106
gtggaagttc aagggaagaa gcctggttcc aaacacaaag ccaccattca ctgt        54

<210> SEQ ID NO 107
<211> LENGTH: 57
<212> TYPE: DNA
<213> ORGANISM: Artificial Sequence
<220> FEATURE:
<223> OTHER INFORMATION: Synthetic

<400> SEQUENCE: 107
gtggaagttc aagggaagaa gcctctcggt tccaaacaca agccaccat tcactgt     57

<210> SEQ ID NO 108
<211> LENGTH: 60
<212> TYPE: DNA
<213> ORGANISM: Artificial Sequence
<220> FEATURE:
<223> OTHER INFORMATION: Synthetic

<400> SEQUENCE: 108
gtggaagttc aagggaagaa gcctctcaag ggttccaaac acaaagccac cattcactgt     60

<210> SEQ ID NO 109
<211> LENGTH: 52
<212> TYPE: DNA
<213> ORGANISM: Artificial Sequence
<220> FEATURE:
<223> OTHER INFORMATION: Synthetic
```

```
<400> SEQUENCE: 109
gtggaagttc aagggaagaa gcctctctaa acacaaagcc accattcact gt          52

<210> SEQ ID NO 110
<211> LENGTH: 62
<212> TYPE: DNA
<213> ORGANISM: Glycine max

<400> SEQUENCE: 110
gttgaaattc agcagaagaa gcctctctca agggttccaa acacaaagcc accattcact  60
gt                                                                62

<210> SEQ ID NO 111
<211> LENGTH: 55
<212> TYPE: DNA
<213> ORGANISM: Artificial Sequence
<220> FEATURE:
<223> OTHER INFORMATION: Synthetic

<400> SEQUENCE: 111
gttgaaattc agcagaagaa gcctctcttc caaacacaaa gccaccattc actgt       55

<210> SEQ ID NO 112
<211> LENGTH: 60
<212> TYPE: DNA
<213> ORGANISM: Artificial Sequence
<220> FEATURE:
<223> OTHER INFORMATION: Synthetic

<400> SEQUENCE: 112
gttgaaattc agcagaagaa gcctctcaag ggttccaaac acaaagccac cattcactgt  60

<210> SEQ ID NO 113
<211> LENGTH: 57
<212> TYPE: DNA
<213> ORGANISM: Artificial Sequence
<220> FEATURE:
<223> OTHER INFORMATION: Synthetic

<400> SEQUENCE: 113
gttgaaattc agcagaagaa gcctctctgt tccaaacaca aagccaccat tcactgt     57

<210> SEQ ID NO 114
<211> LENGTH: 51
<212> TYPE: DNA
<213> ORGANISM: Artificial Sequence
<220> FEATURE:
<223> OTHER INFORMATION: Synthetic

<400> SEQUENCE: 114
gttgaaattc agcagaagaa gcctctcaaa cacaaagcca ccattcactg t           51

<210> SEQ ID NO 115
<211> LENGTH: 54
<212> TYPE: DNA
<213> ORGANISM: Artificial Sequence
<220> FEATURE:
<223> OTHER INFORMATION: Synthetic

<400> SEQUENCE: 115
gttgaaattc agcagaagaa gcctctctcc aaacacaaag ccaccattca ctgt        54

<210> SEQ ID NO 116
```

```
<211> LENGTH: 49
<212> TYPE: DNA
<213> ORGANISM: Artificial Sequence
<220> FEATURE:
<223> OTHER INFORMATION: Synthetic

<400> SEQUENCE: 116
gttgaaattc agcagaagaa gttccaaaca caaagccacc attcactgt          49

<210> SEQ ID NO 117
<211> LENGTH: 57
<212> TYPE: DNA
<213> ORGANISM: Artificial Sequence
<220> FEATURE:
<223> OTHER INFORMATION: Synthetic

<400> SEQUENCE: 117
gttgaaattc agcagaagaa gctcaagggt tccaaacaca aagccaccat tcactgt  57

<210> SEQ ID NO 118
<211> LENGTH: 58
<212> TYPE: DNA
<213> ORGANISM: Artificial Sequence
<220> FEATURE:
<223> OTHER INFORMATION: Synthetic

<400> SEQUENCE: 118
gttgaaattc agcagaagaa gcctctctgg ttccaaacac aaagccacca ttcactgt  58

<210> SEQ ID NO 119
<211> LENGTH: 62
<212> TYPE: DNA
<213> ORGANISM: Glycine max

<400> SEQUENCE: 119
gctgggtcaa gaatccatgg agatccctca gttatgttct cagggatgtg cttgtaattg  60
ct                                                                62

<210> SEQ ID NO 120
<211> LENGTH: 60
<212> TYPE: DNA
<213> ORGANISM: Artificial Sequence
<220> FEATURE:
<223> OTHER INFORMATION: Synthetic

<400> SEQUENCE: 120
gctgggtcaa gaatccatgg atccctcagt tatgttctca gggatgtgct tgtaattgct  60

<210> SEQ ID NO 121
<211> LENGTH: 58
<212> TYPE: DNA
<213> ORGANISM: Artificial Sequence
<220> FEATURE:
<223> OTHER INFORMATION: Synthetic

<400> SEQUENCE: 121
gctgggtcaa gaatccatgg ccctcagtta tgttctcagg gatgtgcttg taattgct   58

<210> SEQ ID NO 122
<211> LENGTH: 57
<212> TYPE: DNA
<213> ORGANISM: Artificial Sequence
<220> FEATURE:
<223> OTHER INFORMATION: Synthetic

<400> SEQUENCE: 122
```
gctgggtcaa gaatccatgg cctcagttat gttctcaggg atgtgcttgt aattgct    57

<210> SEQ ID NO 123
<211> LENGTH: 55
<212> TYPE: DNA
<213> ORGANISM: Artificial Sequence
<220> FEATURE:
<223> OTHER INFORMATION: Synthetic

<400> SEQUENCE: 123
gctgggtcaa gaatccatcc tcagttatgt tctcagggat gtgcttgtaa ttgct    55

<210> SEQ ID NO 124
<211> LENGTH: 58
<212> TYPE: DNA
<213> ORGANISM: Artificial Sequence
<220> FEATURE:
<223> OTHER INFORMATION: Synthetic

<400> SEQUENCE: 124
gctgggtcaa gaatccatgg acctcagtta tgttctcagg gatgtgcttg taattgct    58

<210> SEQ ID NO 125
<211> LENGTH: 61
<212> TYPE: DNA
<213> ORGANISM: Artificial Sequence
<220> FEATURE:
<223> OTHER INFORMATION: Synthetic

<400> SEQUENCE: 125
gctgggtcaa gaatccatgg aatccctcag ttatgttctc aggatgtgc ttgtaattgc    60
t    61

<210> SEQ ID NO 126
<211> LENGTH: 62
<212> TYPE: DNA
<213> ORGANISM: Glycine max

<400> SEQUENCE: 126
gctgggtcaa gaatccatgg agatccctca gttatgttct cagggatgtg cttgtaattg    60
ct    62

<210> SEQ ID NO 127
<211> LENGTH: 60
<212> TYPE: DNA
<213> ORGANISM: Artificial Sequence
<220> FEATURE:
<223> OTHER INFORMATION: Synthetic

<400> SEQUENCE: 127
gctgggtcaa gaatccatgg atccctcagt tatgttctca gggatgtgct tgtaattgct    60

<210> SEQ ID NO 128
<211> LENGTH: 58
<212> TYPE: DNA
<213> ORGANISM: Artificial Sequence
<220> FEATURE:
<223> OTHER INFORMATION: Synthetic

<400> SEQUENCE: 128
gctgggtcaa gaatccatgg acctcagtta tgttctcagg gatgtgcttg taattgct    58

<210> SEQ ID NO 129

<210> SEQ ID NO 129
<211> LENGTH: 51
<212> TYPE: DNA
<213> ORGANISM: Artificial Sequence
<220> FEATURE:
<223> OTHER INFORMATION: Synthetic

<400> SEQUENCE: 129
gctgggtcaa gaatccatgg atatgttctc agggatgtgc ttgtaattgc t          51

<210> SEQ ID NO 130
<211> LENGTH: 60
<212> TYPE: DNA
<213> ORGANISM: Artificial Sequence
<220> FEATURE:
<223> OTHER INFORMATION: Synthetic

<400> SEQUENCE: 130
gctgggtcaa gaatccatag atccctcagt tatgttctca gggatgtgct tgtaattgct    60

<210> SEQ ID NO 131
<211> LENGTH: 58
<212> TYPE: DNA
<213> ORGANISM: Artificial Sequence
<220> FEATURE:
<223> OTHER INFORMATION: Synthetic

<400> SEQUENCE: 131
gctgggtcaa gaatccatgg ccctcagtta tgttctcagg gatgtgcttg taattgct     58

<210> SEQ ID NO 132
<211> LENGTH: 55
<212> TYPE: DNA
<213> ORGANISM: Artificial Sequence
<220> FEATURE:
<223> OTHER INFORMATION: Synthetic

<400> SEQUENCE: 132
gctgggtcaa gaatccatgg acagttatgt tctcagggat gtgcttgtaa ttgct        55

<210> SEQ ID NO 133
<211> LENGTH: 57
<212> TYPE: DNA
<213> ORGANISM: Artificial Sequence
<220> FEATURE:
<223> OTHER INFORMATION: Synthetic

<400> SEQUENCE: 133
gctgggtcaa gaatccatgg cctcagttat gttctcaggg atgtgcttgt aattgct      57

<210> SEQ ID NO 134
<211> LENGTH: 55
<212> TYPE: DNA
<213> ORGANISM: Artificial Sequence
<220> FEATURE:
<223> OTHER INFORMATION: Synthetic

<400> SEQUENCE: 134
gctgggtcaa gaatccatcc tcagttatgt tctcagggat gtgcttgtaa ttgct        55

<210> SEQ ID NO 135
<211> LENGTH: 61
<212> TYPE: DNA
<213> ORGANISM: Artificial Sequence
<220> FEATURE:
<223> OTHER INFORMATION: Synthetic

<400> SEQUENCE: 135

```
gctgggtcaa gaatccatgg aatccctcag ttatgttctc agggatgtgc ttgtaattgc    60
t                                                                    61
```

<210> SEQ ID NO 136
<211> LENGTH: 52
<212> TYPE: DNA
<213> ORGANISM: Artificial Sequence
<220> FEATURE:
<223> OTHER INFORMATION: Synthetic

<400> SEQUENCE: 136

```
gtggaagttc aagggaagaa gcctctccaa acacaaagcc accattcact gt            52
```

<210> SEQ ID NO 137
<211> LENGTH: 52
<212> TYPE: DNA
<213> ORGANISM: Artificial Sequence
<220> FEATURE:
<223> OTHER INFORMATION: Synthetic

<400> SEQUENCE: 137

```
gttgaaattc agcagaagaa gcctttccaa acacaaagcc accattcact gt            52
```

<210> SEQ ID NO 138
<211> LENGTH: 58
<212> TYPE: DNA
<213> ORGANISM: Artificial Sequence
<220> FEATURE:
<223> OTHER INFORMATION: Synthetic

<400> SEQUENCE: 138

```
gttgaaattc agcagaagaa gcctctcggg ttccaaacac aaagccacca ttcactgt     58
```

<210> SEQ ID NO 139
<211> LENGTH: 63
<212> TYPE: DNA
<213> ORGANISM: Artificial Sequence
<220> FEATURE:
<223> OTHER INFORMATION: Synthetic

<400> SEQUENCE: 139

```
gttgaaattc agcagaagaa gcctctcttc aagggttcca acacaaagc caccattcac    60 tgt                                                                  63
```

<210> SEQ ID NO 140
<211> LENGTH: 54
<212> TYPE: DNA
<213> ORGANISM: Artificial Sequence
<220> FEATURE:
<223> OTHER INFORMATION: Synthetic

<400> SEQUENCE: 140

```
gttgaaattc agcagaagaa gcctctctcc aaacacaaag ccaccattca ctgt          54
```

<210> SEQ ID NO 141
<211> LENGTH: 55
<212> TYPE: DNA
<213> ORGANISM: Artificial Sequence
<220> FEATURE:
<223> OTHER INFORMATION: Synthetic

<400> SEQUENCE: 141

```
gttgaaattc agcagaagaa gcctctgttc caaacacaaa gccaccattc actgt         55
```

```
<210> SEQ ID NO 142
<211> LENGTH: 40
<212> TYPE: DNA
<213> ORGANISM: Artificial Sequence
<220> FEATURE:
<223> OTHER INFORMATION: Synthetic

<400> SEQUENCE: 142
gttgaaattc agcagaagaa gcctagccac cattcactgt                    40

<210> SEQ ID NO 143
<211> LENGTH: 54
<212> TYPE: DNA
<213> ORGANISM: Artificial Sequence
<220> FEATURE:
<223> OTHER INFORMATION: Synthetic

<400> SEQUENCE: 143
gctgggtcaa gaatccatgt cagttatgtt ctcagggatg tgcttgtaat tgct    54

<210> SEQ ID NO 144
<211> LENGTH: 61
<212> TYPE: DNA
<213> ORGANISM: Artificial Sequence
<220> FEATURE:
<223> OTHER INFORMATION: Synthetic

<400> SEQUENCE: 144
gctgggtcaa gaatccatgg gatccctcag ttatgttctc agggatgtgc ttgtaattgc    60
t                                                                    61

<210> SEQ ID NO 145
<211> LENGTH: 63
<212> TYPE: DNA
<213> ORGANISM: Artificial Sequence
<220> FEATURE:
<223> OTHER INFORMATION: Synthetic

<400> SEQUENCE: 145
gctgggtcaa gaatccatgg aagatccctc agttatgttc tcaggatgt gcttgtaatt    60 gct                                                                 63
```

COMPOSITIONS AND METHODS FOR MODIFICATION OF FATTY ACIDS IN SOYBEAN

CROSS-REFERENCE TO RELATED APPLICATIONS

This application claims the benefit of priority to U.S. Provisional Application Nos. 62/640,682 filed on Mar. 9, 2018, 62/721,331 filed Aug. 22, 2018 and 62/753,718 filed Oct. 31, 2018, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "7489WOPCT_SEQLIST_2019.txt" created on Feb. 26, 2019 and having a size of 92 kilobytes and is filed concurrently with the specification. The sequence listing contained in this ASCII formatted document is part of the specification and is herein incorporated by reference in its entirety.

BACKGROUND

Soybean oil produced in the US is extracted from soybean seeds and has its major use in food products such as cooking oils, shortenings and margarines. The soybean oil can be refined, bleached and deodorized (RBD) and may be hydrogenated to facilitate its use in shortenings. It is nutritionally desirable to produce soybean oils rich in monounsaturated fatty acids with reduced linolenic acid and saturated fatty acids. Recent advances in plant genetic engineering have facilitated the engineering of plants to have improved seed composition, such as improved fatty acid content and composition.

SUMMARY

Provided are methods of altering the fatty acid profile in the seed of a plant, such as an oil seed crop such as soybean, by introducing four or more nucleotide modifications through four or more targeted DNA breaks at four or more genomic loci of a plant, which loci include polynucleotides encoding a FAD2 and a FAD3 polypeptide, such as FAD2-1A, FAD2-1B, FAD3a and FAD3b. The oleic acid content in the seed is increased and the linolenic acid content is decreased compared to the seed of a control plant not comprising the one or more introduced genetic modifications. The modifications can be introduced through targeted DNA breaks at the same time in a reaction vessel and can be introduced using no more than two guide RNAs. In some embodiments, the modifications target more than four distinct genomic loci that are involved in fatty acid metabolism.

The increase in oleic acid content in the seed or oil produced therefrom can be about 70% to about 90% by weight of the total fatty acids and the decrease in linolenic acid content can be less than about 3% by weight of the total fatty acids. In some embodiments, the yield or standard agronomic performance of the plant is not affected by the modifications or altered fatty acid profile.

In some embodiments, the modifications are targeted such that more than one genetic modifications are present within the same coding region; non-coding region; regulatory sequence; or untranslated region of an endogenous polynucleotide encoding a polypeptide that is involved in fatty acid metabolism. In some embodiments, the target site comprises SEQ ID NO: 6 or SEQ ID NO:7. In some embodiments, the double strand break is induced by using a guide RNA that corresponds to a target sequence selected from the group consisting of SEQ ID NOS: 6 and 7.

In some embodiments, the polynucleotides encode a polypeptide comprising an amino acid sequence that is at least 90% identical to SEQ ID NOS: 70, 72 or a combination thereof, and may include at least one of SEQ ID NOS: 35-58, 77, 84-118 and 136-142 and an amino acid sequence that is at least 90% identical to SEQ ID NOS: 74, 76 or a combination thereof and may include at least one of SEQ ID NOS: 59-64, 78, 79, 119-135 and 143-145. The first polynucleotide may comprise SEQ ID NO: 54, the second polynucleotide may comprise SEQ ID NO: 60, the third polynucleotide may comprise SEQ ID NO: 57, and the fourth polynucleotide may comprise SEQ ID NO: 63. In some embodiments, the polynucleotides comprise SEQ ID NO: 55, SEQ ID NO: 61, SEQ ID NO: 58, and SEQ ID NO: 64.

In some embodiments, the genomic loci comprise an edit in a polynucleotide that encodes a FAD3 or FAD2-1 polypeptide comprising an amino acid sequence that is at least 90% identical SEQ ID NOS: 74 or 76 or of SEQ ID NOS: 70 or 72 such that the edit results in reduced expression of a polynucleotide encoding the FAD3 or FAD2-1 polypeptide, reduced activity of the FAD3 or FAD2-polypeptide, generation of one or more alternative spliced transcripts of a polynucleotide encoding the FAD3 or FAD2-1 polypeptide, deletion of one or more active sites of the FAD3 or FAD2-1 polypeptide, frameshift mutation in one or more exons of a polynucleotide encoding the FAD3 or FAD2-1 polypeptide, deletion of a substantial portion of the polynucleotide encoding the FAD3 or FAD2-1 polypeptide or deletion of the polynucleotide encoding the full-length FAD3 or FAD2-1 polypeptide, repression of an enhancer motif present within a regulatory region encoding the FAD3 or FAD2-1 polypeptide, or modification of one or more nucleotides or deletion of a regulatory element operably linked to the expression of the polynucleotide encoding the FAD3 or FAD2-1 polypeptide, wherein the regulatory element is present within a promoter, intron, 3'UTR, terminator, or any combination thereof.

Examples of FAD2 polynucleotides which can be modified include the seed-preferred or seed-specific sequences FAD2-1A, FAD2-1B and the sequences FAD2-2A, FAD2-2B, FAD2-2C, FAD2-2D and FAD2-2E which tend to be constitutively expressed. Examples of FAD3 polynucleotides which can be modified include the seed-preferred sequences FAD3A, FAD3B and the sequences FAD3C and FAD3C-x2 which tend to be constitutively expressed.

Provided are soybean plants comprising four genomic loci, each locus comprising one or more mutations compared to a control plant and encoding a polypeptide that is at least 95% identical to the amino acid sequence of SEQ ID NOS: 70, 72, 74 and 76 and having an altered fatty acid profile and containing no heterologous or foreign DNA at the modified genomic loci. In some embodiments, the four genomic loci comprise SEQ ID NOS: 54, 57, 60, and 63, comprise SEQ ID NOS: 55, 58, 61, and 64 or comprise SEQ ID NOS: 77, 57, 78 and 79. In some embodiments, the oleic acid content in a seed produced by the plant is increased to about 70% to about 90% by weight of the total fatty acids and/or the linolenic acid content in a seed produced by the plant is decreased to less than about 3% by weight of the total fatty acids. In some embodiments, the soybean plant having an altered fatty acid profile does not have substantially affected yield.

In some embodiments, a container is provided comprising a first guide RNA sequence that targets at two different genomic loci of a plant cell, which loci comprise a polynucleotide that encodes a polypeptide comprising an amino acid sequence that is at least 90% identical to SEQ ID NOS:

70 and 72 respectively, and a second guide RNA sequence that targets at least a further two different genomic loci, which loci comprise a polynucleotide that encodes a polypeptide comprising an amino acid sequence that is at least 90% identical to SEQ ID NOS: 74 and 76 respectively. The first and second guide RNA sequences may comprise sequences corresponding to SEQ ID NO: 6 and SEQ ID NO:7 or a fragment there of, respectively. Also provided are plants and plant cells, such as soybean plants and plant cells, and seeds produced therefrom comprising the guide RNA sequences. Also provided are recombinant DNA constructs that express or comprise the guide RNA sequences, and plants and plant cells such as soybean plants and plant cells and seeds produced therefrom, comprising the DNA construct which may be stably incorporated into the genome of the plant cell.

Provided are methods of detecting the presence of a polynucleotide comprising SEQ ID NOs: 36-43, 45-52, 54, 55, 57, 58, 60, 61, 63, 64, 77, 84-91, 93-100, 102-109, 111-118 or 136-145 which is indicative of the presence of a deletion modification in a FAD2-1 or FAD3 allele. The method includes step of contacting a DNA sample obtained from a soybean plant or part thereof with a pair of DNA primer molecules. The first in the pair comprises at least 12 contiguous nucleotides of SEQ ID NOs: 36-43, 45-52, 54, 55, 57, 58, 60, 61, 63, 64, 77, 84-91, 93-100, 102-109, 111-118 or 136-145 and which includes the junction sequence nucleotides at positions 18-19 for SEQ ID NOs: 43, 123, 130 and 134; positions 19-20 for SEQ ID NO: 143; positions 20-21 for SEQ ID NOs: 60-61, 63-64, 116, 120-122, 127, 131, 133 and 144; positions 20-22 for SEQ ID NO: 145; positions 21-22 for SEQ ID NOs: 78-79, 124, 125, 128, 129, 132 and 135; positions 22-23 for SEQ ID NOs: 36 and 117; positions 23-24 for SEQ ID NOs: 55, 94 and 100; positions 24-25 for SEQ ID NOs: 106, 137 and 142; positions 25-26 for SEQ ID NOs: 47 and 88; positions 26-27 for SEQ ID NOs: 46, 48, 87, 91, 98, 99, 108, 112, 114 and 141; positions 27-28 for SEQ ID NOs: 37-40, 45, 50-52, 54, 57, 58, 84, 90, 93, 97, 103, 105, 107, 111, 115, 136 and 138; positions 27-29 for SEQ ID NOs: 49 and 139; positions 28-29 for SEQ ID NOs: 41, 42, 85, 86, 89, 95, 96, 102, 104, 109, 113 and 118; positions 29-30 for SEQ ID NO: 140; or the reverse complement thereof. The second DNA molecule in the pair is complementary to at least 12 contiguous nucleotides of soybean genomic DNA in proximity to and upstream or downstream of the binding site of the first DNA primer molecule, conditions which facilitate a nucleic acid amplification reaction are provided and the nucleic acid amplification reaction is performed, producing a DNA amplicon molecule which is detected, indicating the presence of a deletion modification in a FAD2-1 or FAD3 allele. The first DNA primer molecule in the pair can comprise no more than 0, 1, 2, 3, 4 or 5 nucleotides following the pair of junction sequence nucleotides between which the deletion or insertion was made.

In some embodiments, a method of screening for the presence or absence of a polynucleotide comprising one or more of SEQ ID NOs: 36-43, 45-52, 54, 55, 57, 58, 60, 61, 63, 64, 77, 84-91, 93-100, 102-109, 111-118 and 136-145 in multiple genomic soybean DNA samples is provided. A plurality of genomic soybean DNA samples are contacted with a first and a second DNA primer molecule, comprising SEQ ID NO: 10 and 11 respectively with a DNA probe comprising SEQ ID NO.12, a first and a second DNA primer molecule comprising SEQ ID NO: 13 and 11 respectively with a DNA probe comprising SEQ ID NO: 14, a first and a second DNA primer molecule comprising SEQ ID NO: 15 and 16 respectively with a DNA probe comprising SEQ ID NO: 17, or a first and a second DNA primer molecule comprising SEQ ID NO: 18 and 16 respectively with a DNA probe comprising SEQ ID NO: 17. Conditions which facilitate a nucleic acid amplification reaction are provided and the nucleic acid amplification reactions are performed to produce a DNA amplicon molecule indicating the presence of a wild-type FAD2-1A allele when the first and second DNA primer molecules comprise SEQ ID NOs: 10 and 11 respectively, a wild-type FAD2-1B allele when the first and second DNA primer molecules comprise SEQ ID NO: 13 and 11 respectively, a wild-type FAD3a allele when the first and second DNA primer molecules comprise SEQ ID NO: 15 and 16 respectively, and a wild-type FAD3b allele, when the first and second DNA primer molecules comprise SEQ ID NO: 18 and 16 respectively. The DNA amplicon molecules are detected, and at least one of the genomic soybean DNA samples does not result in the production of the DNA amplicon molecule, thereby indicating the presence of one or more of SEQ ID NOs: 36-43, 45-52, 54, 55, 57, 58, 60, 61, 63, 64, 77, 84-91, 93-100, 102-109, 111-118 or 136-145 in that sample. The nucleic acid reaction conditions may include SEQ ID NO: 12, when the first and second DNA primer molecules comprise SEQ ID NOs: 10 and 11 respectively, SEQ ID NO: 14, when the first and second DNA primer molecules comprise SEQ ID NO: 13 and 11, SEQ ID NO: 17, when the first and second DNA primer molecules comprise SEQ ID NO: 15 and 16 respectively, and SEQ ID NO: 17, when the first and second DNA primer molecules comprise SEQ ID NO: 18 and 16 respectively.

BRIEF DESCRIPTION OF THE DRAWINGS AND SEQUENCE LISTING

The disclosure can be more fully understood from the following detailed description and the accompanying drawings and Sequence Listing that form a part of this application, which are incorporated herein by reference.

FIG. 1A shows edits made to the FAD2-1A coding sequence as described herein, such as in the Mega74 experiment.

FIG. 1B shows edits made to the FAD2-1B coding sequence coding sequence as described herein, such as in the Mega74 experiment FIG. 2 shows edits made to the FAD2-1, FAD2-1B, FAD3a and FAD3b coding sequences as described herein, such as in the Mega82 Experiment FIG. 3A shows the edits made to the FAD2-1A coding sequence as described herein, such as the RV019927 experiment of Example 7.

FIG. 3B shows the edits made to the FAD2-1B coding sequence as described herein, such as the RV019927 experiment of Example 7.

FIG. 4A shows the edits made to the FAD2-1A coding sequence as described herein, such as the RV019929 experiment of Example 7.

FIG. 4B shows the edits made to the FAD2-1B coding sequence as described herein, such as the RV019929 experiment of Example 7.

FIG. 5A shows the edits made to the FAD3a coding sequence as described herein, such as the RV019929 experiment of Example 7.

FIG. 5B shows the edits made to the FAD3b coding sequence as described herein, such as the RV019929 experiment of Example 7.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

Sequence Listing Description
FAD2 and 3 nucleotide and polypeptide sequences; other fatty acid target sequences

| SEQ ID NOS | Description |
| --- | --- |
| SEQ ID NO: 1 | Nucleotide sequence of soybean codon optimized Cas9 |
| SEQ ID NO: 2 | Amino acid sequence of the SV40 nuclear localization signal |
| SEQ ID NO: 3 | Amino acid sequence of the VirD2 nuclear localization signal |
| SEQ ID NO: 4 | Nucleotide sequence of soybean constitutive promoter GM-EF1A2 |
| SEQ ID NO: 5 | Nucleotide sequence of soybean GM-U6-13.1 promoter |
| SEQ ID NO: 6 | Nucleotide sequence of GM-FAD2-1 CR1 |
| SEQ ID NO: 7 | Nucleotide sequence of GM-FAD3 CR2 |
| SEQ ID NO: 8 | Nucleotide sequence of RTW1211 construct |
| SEQ ID NO: 9 | Nucleotide sequence of RTW1312 construct |
| SEQ ID NO: 10 | Nucleotide sequence of FAD2-F1 primer |
| SEQ ID NO: 11 | Nucleotide sequence of FAD2-R1 primer |
| SEQ ID NO: 12 | Nucleotide sequence of FAD2-T1 probe |
| SEQ ID NO: 13 | Nucleotide sequence of FAD2-F2 primer |
| SEQ ID NO: 14 | Nucleotide sequence of FAD2-T2 probe |
| SEQ ID NO: 15 | Nucleotide sequence of FAD3-F1 primer |
| SEQ ID NO: 16 | Nucleotide sequence of FAD3-R2 primer |
| SEQ ID NO: 17 | Nucleotide sequence of FAD3-T2 probe |
| SEQ ID NO: 18 | Nucleotide sequence of FAD3-F2 primer |
| SEQ ID NO: 19 | Nucleotide sequence of Cas9-F primer |
| SEQ ID NO: 20 | Nucleotide sequence of Cas9-R primer |
| SEQ ID NO: 21 | Nucleotide sequence of Cas9-T probe |
| SEQ ID NO: 22 | Nucleotide sequence of PinII-99F primer |
| SEQ ID NO: 23 | Nucleotide sequence of PinII-13R primer |
| SEQ ID NO: 24 | Nucleotide sequence of PinII-69T probe |
| SEQ ID NO: 25 | Nucleotide sequence of SIP-130F primer |
| SEQ ID NO: 26 | Nucleotide sequence of SIP-198R primer |
| SEQ ID NO: 27 | Nucleotide sequence of SIP-170T probe |
| SEQ ID NO: 28 | Nucleotide sequence of PCR primer WOL1007 |
| SEQ ID NO: 29 | Nucleotide sequence of PCR primer WOL1008 |
| SEQ ID NO: 30 | Nucleotide sequence of PCR primer WOL1009 |
| SEQ ID NO: 31 | Nucleotide sequence of PCR primer WOL1100 |
| SEQ ID NO: 32 | Nucleotide sequence of PCR primer WOL1101 |
| SEQ ID NO: 33 | Nucleotide sequence of PCR primer WOL1102 |
| SEQ ID NO: 34 | Nucleotide sequence of PCR primer WOL1103 |
| SEQ ID NO: 35 | Nucleotide sequence of FAD2-1A WT allele near GM-FAD2-1 CR1 site |
| SEQ ID NO: 36 | Nucleotide sequence of FAD2-1A edited allele of the 1.1 variant near GM-FAD2-1 CR1 site |
| SEQ ID NO: 37 | Nucleotide sequence of FAD2-1A edited allele of the 1.2 variant near GM-FAD2-1 CR1 site |
| SEQ ID NO: 38 | Nucleotide sequence of FAD2-1A edited allele of the 1.3 variant near GM-FAD2-1 CR1 site |
| SEQ ID NO: 39 | Nucleotide sequence of FAD2-1A edited allele of the 6.1 variant near GM-FAD2-1 CR1 site |
| SEQ ID NO: 40 | Nucleotide sequence of FAD2-1A edited allele of the 1.4 variant near GM-FAD2-1 CR1 site |
| SEQ ID NO: 41 | Nucleotide sequence of FAD2-1A edited allele of the 1.5 variant near GM-FAD2-1 CR1 site |
| SEQ ID NO: 42 | Nucleotide sequence of FAD2-1A edited allele of the 1.6 variant near GM-FAD2-1 CR1 site |
| SEQ ID NO: 43 | Nucleotide sequence of FAD2-1A edited allele of the 1.7 variant near GM-FAD2-1 CR1 site |
| SEQ ID NO: 44 | Nucleotide sequence of FAD2-1B WT allele near GM-FAD2-1 CR1 site |
| SEQ ID NO: 45 | Nucleotide sequence of FAD2-1B edited allele of the 1.1 variant near GM-FAD2-1 CR1 site |
| SEQ ID NO: 46 | Nucleotide sequence of FAD2-1B edited allele of the 1.2 variant near GM-FAD2-1 CR1 site |
| SEQ ID NO: 47 | Nucleotide sequence of FAD2-1B edited allele of the 1.3 variant near GM-FAD2-1 CR1 site |
| SEQ ID NO: 48 | Nucleotide sequence of FAD2-1B edited allele of the 6.1 variant near GM-FAD2-1 CR1 site |
| SEQ ID NO: 49 | Nucleotide sequence of FAD2-1B edited allele of the 1.4 variant near GM-FAD2-1 CR1 site |
| SEQ ID NO: 50 | Nucleotide sequence of FAD2-1B edited allele of the 1.5 variant near GM-FAD2-1 CR1 site |
| SEQ ID NO: 51 | Nucleotide sequence of FAD2-1B edited allele of the 1.6 variant near GM-FAD2-1 CR1 site |
| SEQ ID NO: 52 | Nucleotide sequence of FAD2-1B edited allele of the 1.7 variant near GM-FAD2-1 CR1 site |
| SEQ ID NO: 53 | Nucleotide sequence of FAD2-1A WT allele near GM-FAD2-1 CR1 site |
| SEQ ID NO: 54 | Nucleotide sequence of FAD2-1A edited allele of the 3.1 variant near GM-FAD2-1 CR1 site |

TABLE 1-continued

Sequence Listing Description
FAD2 and 3 nucleotide and polypeptide sequences; other fatty acid target sequences

| SEQ ID NOS | Description |
| --- | --- |
| SEQ ID NO: 55 | Nucleotide sequence of FAD2-1A edited allele of the 5.3 variant near GM-FAD2-1 CR1 site |
| SEQ ID NO: 56 | Nucleotide sequence of FAD2-1B WT allele near GM-FAD2-1 CR1 site |
| SEQ ID NO: 57 | Nucleotide sequence of FAD2-1B edited allele of the 3.1 and 1.5a variants near GM-FAD2-1 CR1 site |
| SEQ ID NO: 58 | Nucleotide sequence of FAD2-1B edited allele of the 5.3 variant near GM-FAD2-1 CR1 site |
| SEQ ID NO: 59 | Nucleotide sequence of FAD3a WT allele near GM-FAD3 CR2 site |
| SEQ ID NO: 60 | Nucleotide sequence of FAD3a edited allele of the 3.1 variant near GM-FAD3 CR2 site |
| SEQ ID NO: 61 | Nucleotide sequence of FAD3a edited allele of the 5.3 variant near GM-FAD3 CR2 site |
| SEQ ID NO: 62 | Nucleotide sequence of FAD3b WT allele near GM-FAD3 CR2 site |
| SEQ ID NO: 63 | Nucleotide sequence of FAD3b edited allele of the 3.1 variant near GM-FAD3 CR2 site |
| SEQ ID NO: 64 | Nucleotide sequence of FAD3b edited allele of the 5.3 variant near GM-FAD3 CR2 site |
| SEQ ID NO: 65 | Nucleotide sequence of soybean FAD2-1A gene. |
| SEQ ID NO: 66 | Nucleotide sequence of soybean FAD2-1B gene |
| SEQ ID NO: 67 | Nucleotide sequence of soybean FAD3a gene |
| SEQ ID NO: 68 | Nucleotide sequence of soybean FAD3b gene |
| SEQ ID NO: 69 | Nucleotide sequence of soybean FAD2-1A coding sequence (CDS) |
| SEQ ID NO: 70 | Amino acid sequence of soybean FAD2-1A gene |
| SEQ ID NO: 71 | Nucleotide sequence of soybean FAD2-1B coding sequence (CDS) |
| SEQ ID NO: 72 | Amino acid sequence of soybean FAD2-1B gene |
| SEQ ID NO: 73 | Nucleotide sequence of soybean FAD3a coding sequence (CDS) |
| SEQ ID NO: 74 | Amino acid sequence of soybean FAD3a gene |
| SEQ ID NO: 75 | Nucleotide sequence of soybean FAD3b coding sequence (CDS) |
| SEQ ID NO: 76 | Amino acid sequence of soybean FAD3b gene |
| SEQ ID NO: 77 | Nucleotide sequence of FAD2-1A edited allele of the 1.5a variant near GM-FAD2-1 CR1 site |
| SEQ ID NO: 78 | Nucleotide sequence of FAD3a edited allele of the 1.5a variant near GM-FAD3 CR2 site |
| SEQ ID NO: 79 | Nucleotide sequence of FAD3b edited allele of the 1.5a variant near GM-FAD3 CR2 site |
| SEQ ID NO: 80 | Nucleotide sequence of SIP-130F primer |
| SEQ ID NO: 81 | Nucleotide sequence of SIP-198R primer |
| SEQ ID NO: 82 | Nucleotide sequence of SIP-170T probe |
| SEQ ID NO: 83 | Nucleotide sequence of FAD2-1A WT allele near GM-FAD2-1 CR1 site RV019927 experiment |
| SEQ ID NO: 84 | Nucleotide sequence of FAD2-1A edited allele of the 1.1 variant near GM-FAD2-1 CR1 site RV019927 experiment |
| SEQ ID NO: 85 | Nucleotide sequence of FAD2-1A edited allele of the 1.2 variant near GM-FAD2-1 CR1 site RV019927 experiment |
| SEQ ID NO: 86 | Nucleotide sequence of FAD2-1A edited allele of the 1.3 variant near GM-FAD2-1 CR1 site RV019927 experiment |
| SEQ ID NO: 87 | Nucleotide sequence of FAD2-1A edited allele of the 1.4 variant near GM-FAD2-1 CR1 site RV019927 experiment |
| SEQ ID NO: 88 | Nucleotide sequence of FAD2-1A edited allele of the 1.5 variant near GM-FAD2-1 CR1 site RV019927 experiment |
| SEQ ID NO: 89 | Nucleotide sequence of FAD2-1A edited allele of the 1.6 variant near GM-FAD2-1 CR1 site RV019927 experiment |
| SEQ ID NO: 90 | Nucleotide sequence of FAD2-1A edited allele of the 1.7 variant near GM-FAD2-1 CR1 site RV019927 experiment |
| SEQ ID NO: 91 | Nucleotide sequence of FAD2-1A edited allele of the 1.8 variant near GM-FAD2-1 CR1 site RV019927 experiment |
| SEQ ID NO: 92 | Nucleotide sequence of FAD2-1B WT allele near GM-FAD2-1 CR1 site RV019927 experiment |
| SEQ ID NO: 93 | Nucleotide sequence of FAD2-1B edited allele of the 1.1 variant near GM-FAD2-1 CR1 site RV019927 experiment |
| SEQ ID NO: 94 | Nucleotide sequence of FAD2-1B edited allele of the 1.2 variant near GM-FAD2-1 CR1 site RV019927 experiment |
| SEQ ID NO: 95 | Nucleotide sequence of FAD2-1B edited allele of the 1.3 variant near GM-FAD2-1 CR1 site RV019927 experiment |
| SEQ ID NO: 96 | Nucleotide sequence of FAD2-1B edited allele of the 1.4 variant near GM-FAD2-1 CR1 site RV019927 experiment |
| SEQ ID NO: 97 | Nucleotide sequence of FAD2-1B edited allele of the 1.5 variant near GM-FAD2-1 CR1 site RV019927 experiment |
| SEQ ID NO: 98 | Nucleotide sequence of FAD2-1B edited allele of the 1.6 variant near GM-FAD2-1 CR1 site RV019927 experiment |
| SEQ ID NO: 99 | Nucleotide sequence of FAD2-1B edited allele of the 1.7 variant near GM-FAD2-1 CR1 site RV019927 experiment |
| SEQ ID NO: 100 | Nucleotide sequence of FAD2-1B edited allele of the 1.8 variant near GM-FAD2-1 CR1 site RV019927 experiment |

TABLE 1-continued

Sequence Listing Description
FAD2 and 3 nucleotide and polypeptide sequences; other fatty acid target sequences

| SEQ ID NOS | Description |
| --- | --- |
| SEQ ID NO: 101 | Nucleotide sequence of FAD2-1A WT allele near GM-FAD2-1 CR1 site RV019929 experiment |
| SEQ ID NO: 102 | Nucleotide sequence of FAD2-1A edited allele of the 1.1 variant near GM-FAD2-1 CR1 site RV019929 experiment |
| SEQ ID NO: 103 | Nucleotide sequence of FAD2-1A edited allele of the 1.2 variant near GM-FAD2-1 CR1 site RV019929 experiment |
| SEQ ID NO: 104 | Nucleotide sequence of FAD2-1A edited allele of the 1.3 variant near GM-FAD2-1 CR1 site RV019929 experiment |
| SEQ ID NO: 105 | Nucleotide sequence of FAD2-1A edited allele of the 1.4 variant near GM-FAD2-1 CR1 site RV019929 experiment |
| SEQ ID NO: 106 | Nucleotide sequence of FAD2-1A edited allele of the 1.5 variant near GM-FAD2-1 CR1 site RV019929 experiment |
| SEQ ID NO: 107 | Nucleotide sequence of FAD2-1A edited allele of the 1.6 variant near GM-FAD2-1 CR1 site RV019929 experiment |
| SEQ ID NO: 108 | Nucleotide sequence of FAD2-1A edited allele of the 1.7 variant near GM-FAD2-1 CR1 site RV019929 experiment |
| SEQ ID NO: 109 | Nucleotide sequence of FAD2-1A edited allele of the 1.8 variant near GM-FAD2-1 CR1 site RV019929 experiment |
| SEQ ID NO: 110 | Nucleotide sequence of FAD2-1B WT allele near GM-FAD2-1 CR1 site RV019929 experiment |
| SEQ ID NO: 111 | Nucleotide sequence of FAD2-1B edited allele of the 1.1 variant near GM-FAD2-1 CR1 site RV019929 experiment |
| SEQ ID NO: 112 | Nucleotide sequence of FAD2-1B edited allele of the 1.2 variant near GM-FAD2-1 CR1 site RV019929 experiment |
| SEQ ID NO: 113 | Nucleotide sequence of FAD2-1B edited allele of the 1.3 variant near GM-FAD2-1 CR1 site RV019929 experiment |
| SEQ ID NO: 114 | Nucleotide sequence of FAD2-1B edited allele of the 1.4 variant near GM-FAD2-1 CR1 site RV019929 experiment |
| SEQ ID NO: 115 | Nucleotide sequence of FAD2-1B edited allele of the 1.5 variant near GM-FAD2-1 CR1 site RV019929 experiment |
| SEQ ID NO: 116 | Nucleotide sequence of FAD2-1B edited allele of the 1.6 variant near GM-FAD2-1 CR1 site RV019929 experiment |
| SEQ ID NO: 117 | Nucleotide sequence of FAD2-1B edited allele of the 1.7 variant near GM-FAD2-1 CR1 site RV019929 experiment |
| SEQ ID NO: 118 | Nucleotide sequence of FAD2-1B edited allele of the 1.8 variant near GM-FAD2-1 CR1 site RV019929 experiment |
| SEQ ID NO: 119 | Nucleotide sequence of FAD3a WT allele near GM-FAD3 CR2 site RV019929 experiment |
| SEQ ID NO: 120 | Nucleotide sequence of FAD3a edited allele of the 1.1 variant near GM-FAD3 CR2 site RV019929 experiment |
| SEQ ID NO: 121 | Nucleotide sequence of FAD3a edited allele of the 1.2 variant near GM-FAD3 CR2 site RV019929 experiment |
| SEQ ID NO: 122 | Nucleotide sequence of FAD3a edited allele of the 1.3 variant near GM-FAD3 CR2 site RV019929 experiment |
| SEQ ID NO: 123 | Nucleotide sequence of FAD3a edited allele of the 1.4 variant near GM-FAD3 CR2 site RV019929 experiment |
| SEQ ID NO: 124 | Nucleotide sequence of FAD3a edited allele of the 1.5 variant near GM-FAD3 CR2 site RV019929 experiment |
| SEQ ID NO: 125 | Nucleotide sequence of FAD3a edited allele of the 1.6 variant near GM-FAD3 CR2 site RV019929 experiment |
| SEQ ID NO: 126 | Nucleotide sequence of FAD3b WT allele near GM-FAD3 CR2 site |
| SEQ ID NO: 127 | Nucleotide sequence of FAD3b edited allele of the 1.1 variant near GM-FAD3 CR2 site RV019929 experiment |
| SEQ ID NO: 128 | Nucleotide sequence of FAD3b edited allele of the 1.2 variant near GM-FAD3 CR2 site RV019929 experiment |
| SEQ ID NO: 129 | Nucleotide sequence of FAD3b edited allele of the 1.3 variant near GM-FAD3 CR2 site RV019929 experiment |
| SEQ ID NO: 130 | Nucleotide sequence of FAD3b edited allele of the 1.4 variant near GM-FAD3 CR2 site RV019929 experiment |
| SEQ ID NO: 131 | Nucleotide sequence of FAD3b edited allele of the 1.5 variant near GM-FAD3 CR2 site RV019929 experiment |
| SEQ ID NO: 132 | Nucleotide sequence of FAD3b edited allele of the 1.6 variant near GM-FAD3 CR2 site RV019929 experiment |
| SEQ ID NO: 133 | Nucleotide sequence of FAD3b edited allele of the 1.7 variant near GM-FAD3 CR2 site RV019929 experiment |
| SEQ ID NO: 134 | Nucleotide sequence of FAD3b edited allele of the 1.8 variant near GM-FAD3 CR2 site RV019929 experiment |
| SEQ ID NO: 135 | Nucleotide sequence of FAD3b edited allele of the 1.9 variant near GM-FAD3 CR2 site RV019929 experiment |
| SEQ ID NO: 136 | Nucleotide sequence of FAD2-1A edited allele of the 1.9 variant near GM-FAD2-1 CR1 site RV019929 experiment |
| SEQ ID NO: 137 | Nucleotide sequence of FAD2-1B edited allele of the 1.9 variant near GM-FAD2-1 CR1 site RV019929 experiment |
| SEQ ID NO: 138 | Nucleotide sequence of FAD2-1B edited allele of the 1.10 variant near GM-FAD2-1 CR1 site RV019929 experiment |

TABLE 1-continued

Sequence Listing Description
FAD2 and 3 nucleotide and polypeptide sequences; other fatty acid target sequences

| SEQ ID NOS | Description |
|---|---|
| SEQ ID NO: 139 | Nucleotide sequence of FAD2-1B edited allele of the 1.11 variant near GM-FAD2-1 CR1 site RV019929 experiment |
| SEQ ID NO: 140 | Nucleotide sequence of FAD2-1B edited allele of the 1.12 variant near GM-FAD2-1 CR1 site RV019929 experiment |
| SEQ ID NO: 141 | Nucleotide sequence of FAD2-1B edited allele of the 1.13 variant near GM-FAD2-1 CR1 site RV019929 experiment |
| SEQ ID NO: 142 | Nucleotide sequence of FAD2-1B edited allele of the 1.14 variant near GM-FAD2-1 CR1 site RV019929 experiment |
| SEQ ID NO: 143 | Nucleotide sequence of FAD3a edited allele of the 1.7 variant near GM-FAD3 CR2 site RV019929 experiment |
| SEQ ID NO: 144 | Nucleotide sequence of FAD3a edited allele of the 1.8 variant near GM-FAD3 CR2 site RV019929 experiment |
| SEQ ID NO: 145 | Nucleotide sequence of FAD3a edited allele of the 1.9 variant near GM-FAD3 CR2 site RV019929 experiment |

DETAILED DESCRIPTION

Compositions and methods related to modified plants, such as soybean plants, producing seeds high in oleic acid and low linolenic acid are provided. Suitable plants include oil seed plants, such as canola, sunflower and soybean. Plants, such as soybean plants, that have been modified using genomic editing techniques to produce seeds having a desirable fatty acid profile are provided. The inventors found that modifying four or more targeted DNA breaks at four or more genomic loci of a plant in FAD2 and FAD3 alleles, such as both FAD2-1 alleles (FAD2-1A and FAD2-1B) and both FAD3 alleles (FAD3a and FAD3b), using genomic editing technology as described herein provided soybean plants that were robust, high-yielding and produced seeds which were both high in oleic acid and low in linolenic acid. Oil produced from the seeds had superior characteristics including stability, flavor profile, and fatty acid composition.

Modified seeds, such as soybean seeds, are provided with increased levels of oleic acid and decreased levels of linolenic acid. The soybeans described herein may further contain one or more of decreased levels of saturated fatty acids, such as one or more of palmitic and stearic acids, and decreased levels of linoleic acid.

Oils produced from seeds described herein may contain low levels of saturated fatty acids which are desirable in providing a healthy diet. Fats that are solid at room temperature can be used in applications such as the production of non-dairy margarines and spreads, and various applications in confections and in baking. Provided are oils and triglycerides for solid fat applications which may contain a predominance of the very high melting, long chain fatty acid stearic acid and a balance of monounsaturated fatty acid with very little polyunsaturated fat. Solid fat fractions having a triacylglyceride structure with saturated fatty acids occupying the sn-1 and sn-3 positions of the triglycerides and an unsaturated fatty acid at the sn-2 position are provided. This overall fatty acid composition and triglyceride structure confers an optimal solid fat crystal structure and a maximum melting point with minimal saturated fatty acid content.

The modified plants, seeds and oil compositions disclosed herein are produced by genomic editing techniques which facilitate the editing of the FAD2-1A, FAD-2-1B, FAD3a and FAD3b alleles. The sense strand or the complement thereof may be edited.

A "FAD2", "FAD2-1", "FAD2-1A" or FAD2-1B" or a "FAD2-modified plant", "FAD2-1-modified plant", "FAD2-1A-modified plant" or "FAD2-1B modified plant" generally refers to a modified plant or mutant plant that has one or more nucleotide changes in a genomic region that encodes a polypeptide that is at least 80%, 85%, 90%, 95% or 99% identical to one of SEQ ID NOS: 65-66 or an allelic variant thereof. A "FAD3", "FAD3a", "FAD3b", "FAD3-modified plant", "FAD3a-modified plant" or a "FAD3b-modified plant generally refers to a modified plant or mutant plant that has one or more nucleotide changes in a genomic region that encodes a polypeptide that is at least 80%, 85%, 90%, 95% or 99% identical to one of SEQ ID NOS: 67-68 or an allelic variant thereof. The nucleotide changes in the genomic regions of SEQ ID NOS: 65-68 can include modifications that result in one or more of SEQ ID NOs: 35-64 being contained within the genomic region. The seeds produced by the modified plant and the oil produced therefrom shows increased oleic acid including for example at least about 75% or 80% oleic acid and reduced linolenic acid, for example, less than about 3.5%, 3%, 2.5% or 2% linolenic acid.

In some embodiments the polynucleotides disclosed herein may be isolated polynucleotides. An "isolated polynucleotide" generally refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A regulatory element generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

An enhancer element is any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) is defined as any nucleic acid molecule which inhibits the transcription when functionally linked to a promoter regardless of relative position.

Promotors which may be useful in the methods and compositions provided include those containing cis elements, promoters functional in a plant cell, tissue specific and tissue-preferred promotors, developmentally regulated promoters and constitutive promoters. "Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

"Promoter functional in a plant" is a promoter capable of initiating transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" generally refers to a promoter whose activity is determined by developmental events.

"Constitutive promoter" generally refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

Provided are sequences which are heterologous nucleotide sequences which can be used in the methods and compositions disclosed herein. A "heterologous nucleotide sequence" generally refers to a sequence that is not naturally occurring with the sequence of the disclosure. While this nucleotide sequence is heterologous to the sequence, it may be homologous, or native, or heterologous, or foreign, to the plant host. However, it is recognized that the instant sequences may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Provided are functional fragments of the sequences disclosed herein. A "functional fragment" refers to a portion or subsequence of the sequence described in the present disclosure in which, the ability to modulate gene expression is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the Target sequences of the present disclosure is any nucleic acid fragment that is capable of modulating the expression of a coding sequence or functional RNA in a similar manner to the Target sequences of the present disclosure.

The polynucleotide sequence of the targets of the present disclosure (e.g., SEQ ID NOS: 65-68) and the coding sequences SEQ ID NO: 69, 71, 73, or 75, encoding the polypeptides 70, 72, 74 or 76 respectively, may be modified or altered to reduce their expression or the characteristics of the protein. Examples of such modifications are one or more of the sequences listed in Table 1. As one of ordinary skill in the art will appreciate, modification or alteration can also be made without substantially affecting the gene expression function. The methods are well known to those of skill in the art. Sequences can be modified, for example by insertion, deletion, or replacement of template sequences through any modification approach. The genomic sequences contain introns and exons which may be targeted according to the methods disclosed herein.

SEQ ID NO: 65 (soybean FAD2-1A gene) has the start codon at position 1-3 and the stop codon at position 1329-

1331, exon1 is from positions 1-3, intron1 is from positions 4-170, exon2 is from positions 171-1331.

SEQ ID NO: 66 (soybean FAD2-1B gene) has the start codon at position 1-3 and the stop codon at position 1322-1324, exon1 is from positions 1-3, intron1 is from positions 4-163, exon2 is from positions 164-1324.

SEQ ID NO: 67 (soybean FAD3a gene) has the start codon at position 1-3 and the stop codon at position 3866-3868, exon1 is from positions 1-293, intron1 is from positions 294-460, exon2 is from positions 461-550, intron2 is from positions 551-874, exon3 is from positions 875-941, intron3 is from positions 942-1076, exon4 is from positions 1077-1169, intron4 is from positions 1170-1278, exon5 is from positions 1279-1464, intron5 is from positions 1465-1756, exon6 is from positions 1757-1837, intron6 is from positions 1838-2874, exon7 is from positions 2875-3012, intron7 is from positions 3013-3685, exon8 is from positions 3686-3868.

SEQ ID NO: 68 (soybean FAD3b gene) has the start codon at position 1-3 and the stop codon at position 3894-3896, exon1 is from positions 1-305, intron1 is from positions 306-497, exon2 is from positions 498-587, intron2 is from positions 588-935, exon3 is from positions 936-1002, intron3 is from positions 1003-1144, exon4 is from positions 1145-1237, intron4 is from positions 1238-1335, exon5 is from positions 1336-1521, intron5 is from positions 1522-1636, exon6 is from positions 1637-1717, intron6 is from positions 1637-1717, exon7 is from positions 2950-3087, intron7 is from positions 3088-3713, exon8 is from positions 3714-3896.

Variant promotors can be used in the methods and compositions disclosed herein. A "variant promoter" as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

In some aspects of the present disclosure, the fragments of polynucleotide sequences disclosed herein (such as SEQ ID 65-69, 71, 73, or 75) can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides of nucleic acid sequences or polypeptides encoded by SEQ ID NOS: 69, 71, 73, or 75. In another aspect of the present disclosure, the fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides and further may include a sequence such as one or more of SEQ ID NOS: 1-64.

Provided are sequences that are a full complement or a full-length complement of those disclosed herein, such as the nucleotide sequences in Table 1. The terms "full complement" and "full-length complement" are used interchangeably herein, and refer to a complement of a given nucleotide sequence, wherein the complement and the nucleotide sequence consist of the same number of nucleotides and are 100% complementary.

Provided are sequences that are "substantially similar" or "corresponding substantially" to those disclosed herein which can be used in the methods and compositions described herein. The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

Provided are compositions and methods that includes materials, steps, features, components, or elements that consist essentially of a particular component. The transitional phrase "consisting essentially of" generally refers to a composition, method that includes materials, steps, features, components, or elements, in addition to those literally disclosed, provided that these additional materials, steps, features, components, or elements do not materially affect the basic and novel characteristic(s) of the claimed subject matter, e.g., one or more of the claimed sequences.

Isolated promoter sequences can be comprised in the methods and compositions, such as a recombinant DNA construct, of the present disclosure and can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended levels about $1/10,000$ transcripts to about $1/100,000$ transcripts to about $1/500,000$ transcripts. Conversely, a strong promoter drives expression of a coding sequence at high level, or at about $1/10$ transcripts to about $1/100$ transcripts to about $1/1,000$ transcripts. Similarly, a "moderate constitutive" promoter is somewhat weaker than a strong constitutive promoter like the maize ubiquitin promoter.

In addition to modulating gene expression, the expression modulating elements disclosed herein are also useful as probes or primers in nucleic acid hybridization experiments. The nucleic acid probes and primers hybridize under stringent conditions to a target DNA sequence. A "probe" is generally referred to an isolated/synthesized nucleic acid to which, is attached a conventional detectable label or reporter molecule, such as for example, a radioactive isotope, ligand, chemiluminescent agent, bioluminescent molecule, fluorescent label or dye, or enzyme. Such detectable labels may be covalently linked or otherwise physically associated with the probe. "Primers" generally referred to isolated/synthesized nucleic acids that hybridize to a complementary target DNA strand which is then extended along the target DNA strand by a polymerase, e.g., a DNA polymerase. Primer pairs often used for amplification of a target nucleic acid sequence, e.g., by the polymerase chain reaction (PCR) or other conventional nucleic-acid amplification methods. Primers are also used for a variety of sequencing reactions, sequence captures, and other sequence-based amplification methodologies. Primers are generally about 15, 20, 25 nucleotides or more, and probes can also be longer about 30, 40, 50 and up to a few hundred base pairs. Such probes and primers are used in hybridization reactions to target DNA or RNA sequences under high stringency hybridization conditions or under lower stringency conditions, depending on the need.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

In some embodiments, substantially similar nucleic acid sequences encompassed by this disclosure are those sequences that are 80% identical to the nucleic acid fragments reported herein or which are 80% identical to any portion of the nucleotide sequences reported herein. Nucleic acid fragments which are at least 90% or at least 95% identical to the nucleic acid sequences reported herein, or which are at least 90% or at least 95% identical to any portion of the nucleotide sequences reported herein are also provided. It is well understood by one skilled in the art that many levels of sequence identity are useful in identifying related polynucleotide sequences. Useful examples of percent identities are those listed above, or also preferred is any integer percentage from 71% to 100%, such as at least, at least about or about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, the sequences or isolated sequences of the present disclosure comprise a nucleotide or polypeptide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOS: 65-69, 71, 73 or 75. It is known to one of skilled in the art that a 5' UTR region can be altered (deletion or substitutions of bases) or replaced by an alternative 5'UTR while maintaining promoter activity.

Provided are substantially similar sequences useful in compositions and methods provided herein. A "substantially similar sequence" generally refers to variants of the disclosed sequences such as those that result from site-directed mutagenesis, as well as synthetically derived sequences. A substantially similar promoter sequence of the present disclosure also generally refers to those fragments of a particular promoter nucleotide sequence disclosed herein that operate to promote the constitutive expression of an operably linked heterologous nucleic acid fragment. These promoter fragments comprise at least about 20 contiguous nucleotides, at least about 50 contiguous nucleotides, at least about 75 contiguous nucleotides, preferably at least about 100 contiguous nucleotides of the particular promoter nucleotide sequence disclosed herein or a sequence that is at least 95 to about 99% identical to such contiguous sequences. The nucleotides of such fragments will usually include the TATA recognition sequence (or CAAT box or a CCAAT) of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. Variants of these promoter fragments, such as those resulting from site-directed mutagenesis, are encompassed by the compositions of the present disclosure.

Provided are sequences which contain one or more degenerate codons to those provided in the sequence listing. "Codon degeneracy" generally refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect similar or identical sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CAB/OS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS*. 5:151-153 (1989); Higgins, D. G. et al., *Comput. Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid). A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN generally refers to a BLAST program that compares a nucleotide query sequence against a nucleotide sequence database.

The present disclosure provides genes, mutated genes, chimeric genes and recombinant expression constructs. "Gene" includes a nucleic acid fragment that expresses a functional molecule such as, but not limited to, a specific protein, including regulatory sequences preceding (5' non-coding sequences) and following (3' non-coding sequences) the coding sequence. "Native gene" generally refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

"Chimeric gene" or "recombinant expression construct", which are used interchangeably, includes any gene that is not a native gene, comprising regulatory and coding sequences that are not found together in nature. Accordingly, a chimeric gene may comprise regulatory sequences and coding sequences that are derived from different sources.

"Coding sequence" generally refers to a polynucleotide sequence which codes for a specific amino acid sequence.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" generally refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") generally refers to RNA that is without introns and that can be translated into protein by the cell. "cDNA" generally refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA generally refers to RNA transcript that includes mRNA and so can be translated into protein within a cell or in vitro. "Antisense RNA" generally refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" generally refers to antisense RNA, ribozyme RNA, or other RNA that may not be translated but yet has an effect on cellular processes.

The term "operably linked" or "functionally linked" generally refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, generally refers to the production of a functional end-product e.g., an mRNA or a protein (precursor or mature).

The term "expression cassette" as used herein, generally refers to a discrete nucleic acid fragment into which a nucleic acid sequence or fragment can be cloned or synthesized through molecular biology techniques.

Expression or overexpression of a gene involves transcription of the gene and translation of the mRNA into a precursor or mature protein. "Antisense inhibition" generally refers to the production of antisense RNA transcripts capable of suppressing the expression of the target protein. "Overexpression" generally refers to the production of a gene product in transgenic organisms that exceeds levels of production in normal or non-transformed organisms. "Co-suppression" generally refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

As stated herein, "suppression" includes a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" generally refers to an enzyme that is produced naturally in a non-transgenic or wild type cell. The terms "non-transgenic" and "wild type" are used interchangeably herein.

"Altering expression" or "modulating expression" generally refers to the production of gene product(s) in plants in amounts or proportions that differ significantly from the amount of the gene product(s) produced by the corresponding wild-type plants (i.e., expression is increased or decreased).

"Transformation" as used herein generally refers to both stable transformation and transient transformation.

"Stable transformation" generally refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" generally refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Genome" as it applies to plant cells encompasses not only chromosomal DNA found within the nucleus, but organelle DNA found within subcellular components (e.g., mitochondrial, plastid) of the cell.

"Genetic modification" generally refers to modification of any nucleic acid sequence or genetic element by insertion, deletion, or substitution of one or more nucleotides in an endogenous nucleotide sequence by genome editing or by insertion of a recombinant nucleic acid, e.g., as part of a vector or construct in any region of the plant genomic DNA by routine transformation techniques. Examples of modification of genetic components include, but are not limited to, promoter regions, 5' untranslated leaders, introns, genes, 3' untranslated regions, and other regulatory sequences or sequences that affect transcription or translation of one or more nucleic acid sequences.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

Provided are plants which are dicots. The terms "dicot" and "dicotyledonous plant" are used interchangeably herein. A dicot of the current disclosure includes the following families: Brassicaceae, Leguminosae, and Solanaceae.

Progeny plants are provided. "Progeny" comprises any subsequent generation of a plant, and can include F1 progeny, F2 progeny F3 progeny and so on.

The heterologous polynucleotide can be stably integrated within the genome such that the polynucleotide is passed on to successive generations. The heterologous polynucleotide may be integrated into the genome alone or as part of a recombinant DNA construct. The alterations of the genome (chromosomal or extra-chromosomal) by conventional plant breeding methods, by genome editing procedures that do not result in an insertion of a foreign polynucleotide, or by naturally occurring events such as random cross-fertilization, non-recombinant viral infection, non-recombinant bacterial transformation, non-recombinant transposition, or spontaneous mutation are also methods of modifying a host genome.

"Transient expression" generally refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

Provided are plasmids, vectors and cassettes which contain one or more of the sequences provided, including any combination of sequence components disclosed in the Examples. The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Provided are recombinant DNA constructs or recombinant expression constructs which contain the sequences disclosed herein, including any combination of sequence components disclosed in the Examples. The term "recombinant DNA construct" or "recombinant expression construct" is used interchangeably and generally refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, seed or oil extracted therefrom, altering the fatty acid profile of a plant seed, altering the amounts of fatty acids in a plant seed on seed oil, and the like as disclosed herein. Plants having a desirable phenotype and seed and oil compositions having a fatty acid profile as disclosed herein can be generated by modulating the suppression of FAD2 and FAD3, for example by modulating the suppression of multiple FAD2 and FAD3 alleles, such as one, two, three or all of FAD2-1A, FAD2-1B, FAD-3a and FAD3b alleles. Target sites within the FAD2 and FAD3 alleles can be used to generate short deletions and modifications such as described in Table 1. In an embodiment, the plants and seeds modified as disclosed herein, contain only modified genomic sequence, with no heterologous or foreign DNA remaining in the plant from the modification or in the genomic region of the modification or at the target site. Examples of target sites in soybean include GM-FAD2-1 CR1 (SEQ ID NO: 6) at Gm10:50014185..50014166 and Gm20: 35317773..35317754 and GM-FAD3 CR2 (SEQ ID NO: 7) at Gm14:45939600..445939618 and Gm02: 41423563..41423581.

Provided are seeds, such as soybean seeds, which can be processed to produce oils, and the oils produced therefrom, which contain any combination of oleic acid, linolenic acid, linoleic acid, erucic acid (C:22:1) and saturated fatty acids such as stearic acid and palmitic acid in the amounts disclosed herein. Other saturated fatty acids in the soybean seeds and oils which may be increased or decreased compared with a control plant, seed or oil include myristic acid (C:14:0), and long chain saturated fatty acids arachidic acid (C20:0), behenic acid (C22:0) and lignoceric acid (C24:0).

Provided are seeds, such as soybean seeds, which can be processed to produce oils, and the oils produced therefrom, which have at least or at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 percent oleic (C 18:1) acid of the total fatty acids by weight and less than or less than about 100, 99, 98, 97, 96, 95, 94, 93, 92, 91, 90, 89, 88, 87, 86, 85, 84, 83, 82, 81, 80, 79, 78, 76, 75, 74, 73, 72, 71 or 70 percent oleic acid of the total fatty acids by weight.

Provided are seeds, such as soybean seeds, which can be processed to produce oils, and the oils produced therefrom, which have at least or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 percent linolenic (C 18:3) acid of the total fatty acids by weight and less than or less than about 6, 5.5, 5, 4.5, 4, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or 2.0 percent linolenic acid of the total fatty acids by weight.

Provided are soybean seeds which can be processed to produce oils, and the oils produced therefrom, which have at least or at least about 0.5, 1, 2, 3, 4, 5, 6, or 7 percent linoleic (C 18:2) acid of the total fatty acids by weight and less than or less than about 55, 50, 45, 40, 35, 30, 25, 20, 15, 10, 9, 8, 7, 6, 5, 4, or 3 percent linoleic acid of the total fatty acids by weight.

Provided are seeds, such as soybean seeds, which can be processed to produce oils, and the oils produced therefrom, which have at least or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 percent stearic acid (C 18:0) of the total fatty acids by weight and less than or less than about 6, 5.5, 5, 4.5, 4, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or 2.0 percent stearic acid of the total fatty acids by weight.

Provided are seeds, such as soybean seeds, which can be processed to produce oils, and the oils produced therefrom, which have at least or at least about 0.1, 0.5, 1.0, 1.5, 2.0, 2.5, 3.0, 3.5, 4.0, 4.5, 5.0, 5.5, 6.0, 6.5 or 7.0 percent palmitic acid (C 16:0) of the total fatty acids by weight and less than or less than about 12, 11.5, 11.0, 10.5, 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, or 1.0 percent palmitic acid of the total fatty acids by weight.

Provided are seeds, such as soybean seeds, which can be processed to produce oils, and the oils produced therefrom, which have at least or at least about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 percent total saturated fatty acids of the total fatty acids by weight and less than or less than about 16, 15.5, 15, 14.5, 14, 13.5, 13.0, 12.5, 12.0, 11.5, 11.0, 10.5, 10.0, 9.5, 9.0, 8.5, 8.0, 7.5, 7.0, 6.5, 6.0, 5.5, 5.0, 4.5, 4.0, 3.5, 3.0, 2.5 or 2.0 percent total saturated fatty acids of the total fatty acids by weight.

In an embodiment the seeds, such as soybean seeds, which can be processed to produce oils, and the oils produced therefrom, contain elevated oleic and reduced linolenic acid as described herein, and optionally other modified amounts of other fatty acids as described herein.

In an embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

I. Gene Editing

In some embodiments, gene editing may be facilitated through the induction of a double-stranded break (DSB) or single-strand break, in a defined position in the genome near the desired alteration. DSBs can be induced using any DSB-inducing agent available, including, but not limited to, TALENs (transcription activator-like effector nucleases), meganucleases, zinc finger nucleases, Cas9-gRNA and RNA-guided Cas endonuclease systems (based on bacterial CRISPR-Cas systems, such as but not limited to Type I-E, Cas9, Cpf1, and others), guided cpf1 endonuclease systems, and the like. The DSB may be repaired via a Non-Homologous End Joining (NHEJ) pathway in the absence of any additional composition, via template-directed repair in the presence of a polynucleotide modification template, or via homologous recombination with a heterologous polynucleotide (donor DNA molecule). The HDR pathway repairs double-stranded DNA breaks and includes homologous recombination (HR) and single-strand annealing (SSA) (Lieber. 2010 Annu. Rev. Biochem. 79:181-211). In some embodiments, the introduction of a DSB can be combined with the introduction of a polynucleotide modification template or a donor DNA molecule. In some embodiments, the methods do not use TALENs enzymes or technology and plants and seeds are produced from methods which do not use TALENs enzymes or technology.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, (iv) chemical alteration of at least one nucleotide, or (v) any combination of (i)-(iv).

The term "polynucleotide modification template" includes a polynucleotide that comprises at least one nucleotide modification when compared to the nucleotide sequence to be edited.

A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB with or without a modification template or using a DSB-inducing agent, such as an RNA-guided Cas endonuclease, generally comprises: providing to a host cell a DSB-inducing agent, or a nucleic acid encoding a DSB-inducing agent, that recognizes and binds to a target sequence in the chromosomal sequence and is able to induce a DSB in the genomic sequence. In some aspects, at least one polynucleotide modification template comprising at least one nucleotide alteration when compared to the nucleotide sequence to be edited is provided. The polynucleotide modification template can further comprise nucleotide sequences flanking the at least one nucleotide alteration, in which the flanking sequences are substantially homologous to the chromosomal region flanking the DSB.

In addition to the double-strand break inducing agents, site-specific base conversions can also be achieved to engineer one or more nucleotide changes to create one or more edits described herein into the genome. These include for example, a site-specific base edit mediated by an C•G to T•A or an A•T to G•C base editing deaminase enzymes (Gaudelli et al., Programmable base editing of A•T to G•C in genomic DNA without DNA cleavage. Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C->T (or G->A on the opposite strand) or an adenine base editor that would convert adenine to inosine, resulting in an A->G change within an editing window specified by the gRNA.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. Methods for the introduction of Cas endonucleases and guide polynucleotide into plant cells are described, for example, in US 2016/0208272 A1, published 21 Jul. 2016, and in US 2016/0201072 A1, published 14 Jul. 2016. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896.

Other Cas endonuclease systems have been described in PCT patent applications PCT/US16/32073, filed May 12, 2016 and PCT/US16/32028 filed May 12, 2016.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

Provided are plants and seeds which contain an altered or modified target site or sequence. An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide a guide polynucleotide/Cas endonuclease complex to a unique DNA target site.

Provided are plants and seeds in which a functional sequence has been knocked out. The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

In some aspects, the guide polynucleotide/Cas endonuclease system can be used in combination with a co-delivered polynucleotide modification template to allow for editing (modification) of a genomic nucleotide sequence of interest (see also U.S. Patent Application US 2015-0082478 A1, published on Mar. 19, 2015 and WO2015/026886 A1, published on Feb. 26, 2015), or co-delivered with a heterologous (donor) DNA molecule for integration at the double-strand break via homologous recombination.

Provided are plants and seeds in which a functional sequence has been knocked in. The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of sequence identity shared by a target and a donor polynucleotide can vary and includes total lengths and/or regions having unit integer values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of at least or at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% and less than or less than about 100%, 99%, 98%, 97%, 96%, 95%, 94%, 93%, 92%, 91% or 90%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and, Tijssen (1993) Laboratory Techniques in Biochemistry and Molecular Biology—Hybridization with Nucleic Acid Probes, (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, PCT application publication WO2016007347A1, published 14 Jan. 2016, and PCT application publication WO2016025131A1, published 18 Feb. 2016) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569, 834, 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

This disclosure also concerns a method of decreasing the expression of at least one nucleic acid such as a heterologous nucleic acid fragment in a plant cell which comprises:
 (a) transforming a plant cell with the recombinant expression construct described herein;
 (b) growing fertile mature plants from the transformed plant cell of step (a);
 (c) selecting plants containing a transformed plant cell wherein the expression of the nucleic acid such as a heterologous nucleic acid fragment is increased or decreased.

Transformation and selection can be accomplished using methods well-known to those skilled in the art including, but not limited to, the methods described herein.

The soybean seeds can be processed to produce oil and protein. Methods of processing the soybean seeds to produce oil and protein are provided which include one or more steps of dehulling the seeds, crushing the seeds, heating the seeds, such as with steam, extracting the oil, roasting, and extrusion. Processing and oil extraction can be done using solvents or mechanical extraction.

Products formed following processing include, without limitation, soy nuts, soy milk, tofu, texturized soy protein, soybean oil, soy protein flakes, isolated soy protein. Crude or partially degummed oil can be further processed by one or more of degumming, alkali treatment, silica absorption, vacuum bleaching, hydrogenation, interesterification, filtration, deodorization, physical refining, refractionation, and optional blending to produce refined bleached deodorized (RBD) oil.

The oil and protein can be used in animal feed and in food products for human consumption. Provided are food products and animal feed comprising oils, protein and compositions described herein. The food products and animal feed may comprise nucleotides comprising one or more of the modified alleles disclosed herein.

Methods of detecting the modified polynucleotides are provided. Methods of extracting modified DNA from a sample or detecting the presence of DNA corresponding to the modified genomic sequences comprising deletions of FAD2-1 and FAD3, such as presented in FIGS. 1-5 can be carried out. Such methods comprise contacting a sample comprising soybean genomic DNA with a DNA primer set, that when used in a nucleic acid amplification reaction, such as the polymerase chain reaction (PCR), with genomic DNA extracted from soybeans produces an amplicon that is diagnostic for either the presence or absence of the modified FAD2-1A and FAD3 alleles. The methods include the steps of performing a nucleic acid amplification reaction, thereby producing the amplicon and detecting the amplicon.

In some embodiments one of the pair of DNA molecules comprises the wild type sequence where the modification occurs with the second of the pair being upstream or downstream as appropriate and suitably in proximity to the wild type sequence where the modification occurs, such that an amplicon is produced when the wild type allele is present, but no amplicon is produced when the modified allele is present. Suitable primers and probes for use in reactions to detect the presence of the alleles of FAD2-1A (e.g. SEQ ID NOs: 10, 11 and 12 and functional fragments thereof), FAD2-1B (e.g. SEQ ID NOs: 13, 11 and 14 and functional fragments thereof), FAD3a (e.g. SEQ ID NOs: 15, 16 and 17 and functional fragments thereof) and FAD3b (e.g. SEQ ID NOs: 18, 16 and 17 and functional fragments thereof) are provided in Table 2 and described in Example 4. In the context of the methods, in proximity means sufficiently close such that the distance between the first and second of the pair of DNA molecules facilitates the production of an amplicon when included in a DNA amplification reaction comprising soybean genomic DNA. For example, the second primer may bind at a location beginning at, within or less than 1, 2, 5, 10, 20, 30, 40, 50, 60, 70, 80, 90, 100, 150, 200, 250, 300, 350, 400, 450, 500, 600, 700, 800, 900, 1000, 1500, 16, 1700, 1800, 1900, 2000, 2100, 2200, 2300, 2400, 2500, 2600, 2700, 2800, 2900, 3000, 3500, 4000, 4500 or 5000 nucleotides upstream or downstream of the end of the binding site of the first DNA primer molecule.

Probes and primers are provided which are of sufficient nucleotide length to bind specifically to the target DNA sequence under the reaction or hybridization conditions. Suitable probes and primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 25, 24, 23, 22, 21, 20, 19, 18, 17, 16, 15, 14, 13, or 12 nucleotides in length. Such probes and primers can hybridize specifically to a target sequence under high stringency hybridization conditions. Preferably, probes and primers have complete or 100% DNA sequence similarity of contiguous nucleotides with the target sequence, although probes which differ from the target DNA sequence but retain the ability to hybridize to target DNA sequence may be also be used. Reverse complements of the primers and probes disclosed herein are also provided and can be used in the methods and compositions described herein.

In some embodiments, one of the pair of DNA molecules comprises the modification or traverses the modification junction such as the deletion junctions depicted in FIGS. 1-5, with the second DNA molecule of the pair being upstream or downstream of the genomic sequence as appropriate, such that an amplicon is produced when the modified allele is present, but no amplicon is produced when the wild type allele is present. Suitable primers for use in reactions to detect the presence of the modified alleles can be designed based on the junction sequences depicted in FIGS. 1-5 for the modified alleles.

For example, for SEQ ID NO: 54, the deletion junction occurs between positions 27 and 28; a primer can be designed which begins (or includes if beginning before position 1) at position 1 through position 27 and ends (or includes if ending after position 55) at position 29 to 55, provided that the primer is of sufficient length to function in the amplification reaction. The reverse complement of such a primer is also provided.

For example, for SEQ ID NO: 55, the deletion junction occurs between positions 23 and 24; a primer can be designed which begins (or includes if beginning before position 1) at position 1 through position 23 and ends (or includes if ending after position 55) at position 24 to 55, provided that the primer is of sufficient length to function in the amplification reaction. The reverse complement of such a primer is also provided.

For example, for SEQ ID NO: 57, the deletion junction occurs between positions 27 and 28; a primer can be designed which begins (or includes if beginning before position 1) at position 1 through position 27 and ends (or includes if ending after position 57) at position 28 to 57, provided that the primer is of sufficient length to function in the amplification reaction. The reverse complement of such a primer is also provided.

For example, for SEQ ID NO: 58, the deletion junction occurs between positions 27 and 28; a primer can be designed which begins (or includes if beginning before position 1) at position 1 through position 27 and ends (or includes if ending after position 55) at position 29 to 55, provided that the primer is of sufficient length to function in the amplification reaction. The reverse complement of such a primer is also provided.

For example, for SEQ ID NO: 60, the deletion junction occurs between positions 20 and 21; a primer can be designed which begins (or includes if beginning before position 1) at position 1 through position 20 and ends (or includes if ending after position 60) at position 22 to 60, provided that the primer is of sufficient length to function in the amplification reaction. The reverse complement of such a primer is also provided.

For example, for SEQ ID NO: 61, the deletion junction occurs between positions 20 and 21; a primer can be designed which begins (or includes if beginning before position 1) at position 1 through position 20 and ends (or includes if ending after position 58) at position 21 to 58, provided that the primer is of sufficient length to function in the amplification reaction. The reverse complement of such a primer is also provided.

For example, for SEQ ID NOs: 63 and 64, the deletion junction occurs between positions 20 and 21; a primer can be designed which begins (or includes if beginning before position 1) at position 1 through position 20 and ends (or includes if ending after position 60) at position 22 to 60, provided that the primer is of sufficient length to function in the amplification reaction. The reverse complement of such a primer is also provided.

According to another aspect of the invention, methods of detecting the presence of a DNA molecule corresponding to the modified FAD2-1 and FAD3 alleles in a sample, include contacting the sample comprising DNA extracted from a soybean plant, cell or seed with a DNA probe molecule that hybridizes under stringent hybridization conditions with genomic DNA from a soybean comprising the modified FAD2-1 or FAD3 alleles and does not hybridize under stringent hybridization conditions with a control soybean plant DNA, The sample and probe are subjected to stringent hybridization conditions and hybridization of the probe to the DNA from the soybean plant, cell or seed comprising the modified FAD2-1 or FAD3

In some embodiments the primers and probes bind and traverse the modification, such as a deletion junction, in the genomic DNA and have a sequence following the modification or junction in the 5' to 3' direction which is less than 10, 9, 8, 7, 6, 5, 4, 3, or 2 nucleotides in length and at least 1, 2, 3, 4 or 5 nucleotides in length.

EXAMPLES

The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Such modifications are also intended to fall within the scope of the appended claims. For example, one of skill in the art could use template directed repair, insertion of a heterologous polynucleotide to disrupt the native gene, or modification using a deaminase to alter a base to create the same or similar edits to those disclosed in these examples.

Example 1

Soybean Optimized Expression Cassettes for Guide RNA/Cas Endonuclease Based Genome Modification in Soybean Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Natl. Acad. Sci. USA* 109: E2579-86, Jinek et al. (2012) *Science* 337:816-21, Mali et al. (2013) *Science* 339:823-26, and Cong et al. (2013) *Science* 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand -break into said target site.

To use the guide RNA/Cas endonuclease system in soybean, the Cas9 gene from *Streptococcus pyogenes* M1 GAS (SF370) was soybean codon optimized (SEQ ID NO: 1) per standard techniques known in the art. To facilitate nuclear localization of the Cas9 protein in soybean cells, Simian virus 40 (SV40) monopartite amino terminal nuclear localization signal (MAPKKKRKV, SEQ ID NO: 2) and *Agrobacterium tumefaciens* bipartite VirD2 T-DNA border endonuclease carboxyl terminal nuclear localization signal (KRPRDRHDGELGGRKRAR, SEQ ID NO: 3) were incorporated at the amino and carboxyl-termini of the Cas9 open reading frame, respectively. The soybean optimized Cas9 gene was operably linked to a soybean constitutive promoter such as the strong soybean constitutive promoter GM-EF1A2 (US patent application 20090133159 (SEQ ID NO: 4). or regulated promoter by standard molecular biological techniques.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in soybean, the soybean U6 polymerase III promoter and U6 polymerase III terminator were used.

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter for example, GM-U6-13.1 promoter (SEQ ID NO:5), to express guide RNA to direct Cas9 nuclease to designated genomic site. The guide RNA coding sequence was 76 bp long and comprised a 20 bp variable targeting domain from a chosen soybean genomic target site on the 5' end and a tract of 4 or more T residues as a transcription terminator on the 3' end. The first nucleotide of the 20 bp variable targeting domain was a G residue to be used by RNA polymerase III for transcription. Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct.

Example 2

Selection of Soybean FAD2 and FAD3 Target Sites to be Cleaved by the Guide RNA/Cas Endonuclease System A. guideRNA/Cas9 Endonuclease Target Site Design on the Soybean FAD2-1 and FAD3 Genes There are two seed-preferred FAD2-1 genes in soybean (FAD2-1A for Glyma.10g278000 and FAD2-1B for Glyma.20g111000). One guide RNA/Cas9 endonuclease target site (GM-FAD2-1 CR1) was designed to target both the FAD2-1 genes (Table 1). There are also two major FAD3 genes in soybean (FAD3a for Glyma.14g194300 and FAD3b for Glyma.02g227200). The GM-FAD3 CR2 site was designed to target both FAD3 genes (Table 1)

TABLE 1

Guide RNA/Cas9 endonuclease target sites on soybean FAD2-1 genes and FAD3 genes

| Name of gRNA-Cas9 endonuclease target site | Cas endonuclease target sequence (SEQ ID NO:) | Physical location |
| --- | --- | --- |
| GM-FAD2-1 CR1 | 6 | Gm10: 50014185..50014166<br>Gm20: 35317773..35317754 |
| GM-FAD3 CR2 | 7 | Gm14: 45939600..445939618<br>Gm02: 41423563..41423581 |

B. Guide-RNA Expression Cassettes, Cas9 Endonuclease Expression Cassettes and Knockout of the Soybean FAD2-1 and FAD3 Genes.

The soybean U6 small nuclear RNA promoter, GM-U6-13.1 (SEQ ID NO: 5), was used to express guide RNAs to direct Cas9 nuclease to designated genomic target sites. A soybean codon optimized Cas9 endonuclease (SEQ ID NO: 1) expression cassette and a guide RNA expression cassette were linked in the plasmid (RTW1211 or RTW1312). For examples, the RTW1211 construct (SEQ ID NO.8), which contained the GM-FAD2-1 CR1 gRNA expression cassette and the cas9 expression cassette, was made to target both the FAD2-1A and FAD2-1B genes simultaneously. Similarly, the RTW1312 construct (SEQ ID NO.9) was made to target both the FAD3a and Fad3b genes at the same time.

Example 3

Delivery of the Guide RNA/Cas9 Endonuclease System DNA to Soybean by Stable Transformation Soybean somatic embryogenic suspension cultures were induced from a DuPont Pioneer proprietary elite cultivar 93Y21 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8-hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 μl of a 60 mg/ml 1.0 mm gold particle suspension were added in order: 30 μl of equal amount (30 ng/μl) plasmid DNA, 20 μl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or T0 leaf stage for molecular analysis.

Example 4

Detection of Site-Specific Mutations with NHEJ Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, Calif.) with target site-specific primers and FAM-labeled fluorescence probe to check copy number changes of the target sites. The qPCR analysis was done in duplex reactions with a syringolide induced protein (SIP) gene as the endogenous controls and a wild type 93Y21 genomic DNA sample that contains one copy of the target site with 2 alleles, as the single copy calibrator. The endogenous control probe SIP-T was labeled with VIC and the gene-specific probes FAD2-T1, FAD2-T2 and FAD3-T2 were labeled with FAM (Table 2) for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

TABLE 2

Primers/probes used in qPCR analyses of transgenic soybean events.

| Target Site | Primer/Probe Name | Sequences | SEQ ID NOs: |
|---|---|---|---|
| FAD2-1A | FAD2-F1 | TCGTGTGGCCAAAGTGGAA | 10 |
|  | FAD2-R1 | TTTGTGTTTGGAACCCTTGAGA | 11 |
|  | FAD2-T1 (FAM-MGB) | TTCAAGGGAAGAAGCC | 12 |
| FAD2-1B | FAD2-F2 | CCGTGTGGCCAAAGTTGAA | 13 |
|  | FAD2-R1 | TTTGTGTTTGGAACCCTTGAGA | 11 |
|  | FAD2-T2 (FAM-MGB) | TTCAGCAGAAGAAGCC | 14 |
| FAD3a | FAD3-F1 | TAATGGATACCAAAAGGAAGC | 15 |
|  | FAD3-R2 | CAAGCACATCCCTGAGAACATAAC | 16 |
|  | FAD3-T2 (FAM-MGB) | AATCCATGGAGATCCCT | 17 |
| FAD3b | FAD3-F2 | ATACCAACAAAAGGGTTCTTC | 18 |
|  | FAD3-R2 | CAAGCACATCCCTGAGAACATAAC | 16 |
|  | FAD3-T2 (FAM-MGB) | AATCCATGGAGATCCCT | 17 |
| CAS9 | Cas9-F | CCTTCTTCCACCGCCTTGA | 19 |
|  | Cas9-R | TGGGTGTCTCTCGTGCTTTTT | 20 |
|  | Cas9-T (FAM-MGB) | AATCATTCCTGGTGGAGGA | 21 |

TABLE 2-continued

Primers/probes used in qPCR analyses of transgenic soybean events.

| Target Site | Primer/Probe Name | Sequences | SEQ ID NOs: |
|---|---|---|---|
| pINII | pINII-99F | TGATGCCCACATTATAGTGATTAGC | 22 |
|  | pINII-13R | CATCTTCTGGATTGGCCAACTT | 23 |
|  | pINII-69T (FAM-MGB) | ACTATGTGTGCATCCTT | 24 |
| SIP | SIP-130F | TTCAAGTTGGGCTTTTTCAGAAG | 25 |
|  | SIP-198R | TCTCCTTGGTGCTCTCATCACA | 26 |
|  | SIP-170T (VIC-MGB) | CTGCAGCAGAACCAA | 27 |

Since the wild type 93Y21 genomic DNA with two alleles of the target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). Two soybean transformation experiments were carried out. The Mega74 experiment was to use the RTW1211 construct to knockout only the two FAD2-1 genes. Both NHEJ-Hemi and NHEJ-Null were detected in FAD2-1A and FAD2-1B genes (Table 3). In the second Mega82 experiment, the RTW1312 was added in additional to the RTW1211 construct to knockout both the two FAD2-1 genes and the two FAD3 genes. Efficient quadra gene knockout were detected in FAD2-1A, FAD2-1B, FAD3a and FAD3b genes (Table 4).

TABLE 3

FAD2-1 Target site mutations induced by the guide RNA/Cas9 system in 93Y21. Numbers indicate number of events (numbers in parentheses are %).

| Target site | Total event | Wt-Homo (%) | NHEJ-Hemi (%) | NHEJ-Null (%) |
|---|---|---|---|---|
| FAD2-1A | 84 | 29 (35%) | 49 (58%) | 6 (7%) |
| FAD2-1B |  | 25 (30%) | 23 (27%) | 36 (43%) |

TABLE 4

FAD2-1 and FAD3 target site mutations induced by the guide RNA/Cas9 system in 93Y21. Numbers indicate number of events (numbers in parentheses are % of the total analyzed events).

| Target Site | Total event | Wt-Homo (%) | NHEJ-Hemi (%) | NHEJ-Null (%) |
|---|---|---|---|---|
| FAD2-1A | 64 | 7 (11%) | 15 (23%) | 42 (66%) |
| FAD2-1B |  | 11 (17%) | 10 (16%) | 43 (67%) |
| FAD3a |  | 6 (9%) | 8 (13%) | 50 (78%) |
| FAD3b |  | 2 (3%) | 8 (13%) | 54 (84%) |

The target regions of NHEJ-Null events were amplified by regular PCR from the same genomic DNA samples using primers specific respectively to FAD2-1A, FAD2-1B, FAD3a and FAD3b genes (Table 5). The PCR bands were cloned into pCR2.1 vector using a TOPO-TA cloning kit (Invitrogen) and multiple clones were sequenced to check for target site sequence changes as the results of NHEJ. Various small deletions at the Cas9 cleavage site, 3 bp upstream of the PAM, were revealed at all four tested target sites, with most of them resulting in frame-shift knockouts (Table 6, FIG. 1A, FIG. 1B and FIG. 2). These sequence analyses confirmed the occurrence of NHEJ mediated by the guide RNA/Cas9 system at the specific Cas9 target sites.

TABLE 5

PCR primers for the gRNA targets of the FAD2-1 and FAD3 genes

| Target Site | Primer1 | SEQ ID NO: | Primer2 | SEQ ID NO: |
|---|---|---|---|---|
| FAD2-1A | WOL1007 | 28 | WOL1009 | 30 |
| FAD2-1B | WOL1008 | 29 | WOL1009 | 30 |
| FAD3a | WOL1100 | 31 | WOL1101 | 32 |
| FAD3b | WOL1102 | 33 | WOL1103 | 34 |

TABLE 6

Edited Alleles of the FAD2-1A, FAD2-1B, FAD3a and FAD3b genes

| Variant | FAD2-1A | FAD2-1B | FAD3a | FAD3b |
|---|---|---|---|---|
| 1.1 | 11 bp del | 4 bp del |  |  |
| 1.2 | 7 bp del | 11 bp del |  |  |
| 1.3 | 8 bp del | 16 bp del |  |  |
| 6.1 | 5 bp del | 11 bp del |  |  |
| 1.4 | 7 bp del | 1 bp insert |  |  |
| 1.5 | 4 bp del | 7 bp del |  |  |
| 1.6 | 1 bp del | 8 bp del |  |  |
| 1.7 | 26 bp del | 8 bp del |  |  |
| 3.1 | 7 bp del | 5 bp del | 2 bp del | 2 bp del |
| 5.3 | 7 bp del | 7 bp del | 4 bp del | 2 bp del |
| 1.5a | 13 bp del | 5 bp del | 4 bp del | 2 bp del |

Example 5

Compositional Analysis of the Soybean Seeds and Identification of Lead Variants

Screening of seed from edited events was performed using non-destructive single seed Near Infrared analysis (SS-NIR). The instrument used had been calibrated to determine the fatty acid profiles in intact seed while maintaining the seeds individual identity. By so doing seed displaying the desired phenotype could be selected for propagation. SS-NIR calibration models were created using proprietary seed displaying a wide dynamic range in the constituents of interest, e.g., oleic and linolenic acids, as described below.

A Single Seed Near Infrared (SS-NIR) spectrometer (U.S. Pat. No. 7,274,456 B2, issued Sep. 25, 2007; U.S. Pat. No. 7,508,517B2, issued Mar. 24, 2009) was used. In the SS-NIR system an individual bean was introduced into the analytical cell where it was illuminated from all points in three dimensions. The seed was tumbled with an air stream, within an approximated integrating sphere constructed from a 16-mm-diameter quartz cup coated with 6080 white reflectance coating (Labsphere, North Hutton, N.H.). Illumination was provided through 12 optical fibers, connected to four 20 Watt 8211-002 light bulbs (Welch Allyn, Skaneateles Falls, N.Y.), the ends of which were incorporated into the cell cover. The reflected spectral region from 904 to 1686 nm was collected through the apex of the cover of the sampling cell by an NIR512 spectrometer (Control Development, South Bend, Ind.). Each seed was scanned for 6 seconds to collect spectra that were optimized for maximal signal to noise ratio. Spectral quality was monitored during each sample scan by regularly checking the Root Mean Square (RMS) noise of the 100% lines. The 100% lines were computed by the ratio between every two spectra of the triplicate measurement for each sample. Under ideal, noise-free conditions, the 100% lines would be straight horizontal lines at zero absorbance units (AU) since all replicate spectra come from the same sample providing the same spectral features. To minimize instrumental drift, system noise, seed condition and other environmental changes, noise and off-sets were observed in the actual 100% lines. After scanning, the seed was ejected from the sample cup and transferred to an indexed sample tray. The individual identity of each seed was therefore preserved, facilitating instrument calibration.

Separate calibration models were generated for each constituent of interest using Partial Least Square (PLS) analysis coupled with an optimized number of latent variables, spectral range and spectral preprocessing, before being applied to online/offline compositional analysis of the individual seed components, such as the oleic and linolenic acid. The optimized number of latent variables, spectral range and spectral preprocessing were determined by analyzing the training and monitoring subset from the calibration data where the calibration performance reached an optimum level, in terms of Root Mean Square Error of Calibration (RMSEC) and Root Mean Square Error of Cross Validation (RMSECV). For those co-constituents with distinct spectra, such as oil, a few PLS latent variables were used to capture enough information. More PLS latent variables were needed for components with less distinct spectra. After the spectra were preprocessed for multiplicative scatter corrections, Savitsky-Golay derivatives and polynomial smoothing were applied in the spectral region between 904-1540 nm. The number of latent variables was determined as the fewest number of latent variables that resulted in an optimal calibration/cross validation accuracy as determined by the RMSEC (Root Mean Square Error of Calibration) and RMSECV (Root Mean Square Error of Cross Validation), respectively. The optimum calibration model was selected based on the $R^2$ (statistical measure of how close the predicted and reference chemistry data are fitted by the regression line), RMSEC (Root Mean Square Error of Calibration) and RMSECV (Root Mean Square Error of Cross Validation) statistics.

TABLE 7

Statistics for the oleic and linolenic Acid SS-NIR calibrations. The number of reference chemistry measurements used to develop the calibrations for each constituent are shown in column n. The dynamic range in composition underpinning each constituent calibration is shown in the range column.

| Constituent | n | Range (rel %-rel %) | $R^2$ | RMSEC | RMSECV |
|---|---|---|---|---|---|
| Oleic acid | 2725 | 12.8-90.1 | 0.99 | 2.80% | 2.83% |
| Linolenic acid | 2725 | 1.1-12.7 | 0.92 | 0.81% | 0.86% |

$R^2$ = regression coefficient;
RMSEC = Root Mean Square Error of Calibration;
RMSECV = Root Mean Square Error of Cross Validation Thirty-six seed from each $T_0$ edited event were subjected to SS-NIR and the predicted oleic and linolenic acid contents of the seed were used to identify those carrying the desired High Oleic or High Oleic/Low Linolenic phenotype.
Sample Preparation $T_2$ or $T_3$ Homozygous Seed.

Eight soybean seeds were placed in a Spex Certiprep 13/16×2" polycarbonate vial with cap (MedPlast, Monticello, Iowa; cat #1076). A 9/16" stainless steel ball bearing was added. Grinding was performed in a Spex Certiprep 2000 Geno/Grinder at 1500 strokes/min for three 30 second intervals with a 1-minute rest between each cycle. The grinding ball was removed and the powder was thoroughly dispersed with a spatula and analyzed as described below.
GC Fatty Acid Profile Determinations
Two replicate extractions were performed on each sample, as follows:
- Weigh ground sample (approximately 20-30 mg; to an accuracy of 0.1 mg) into 13×100 mm tube (with Teflon® lined cap; VWR (53283-800) and record weight.
- Add 2 mL Heptane, vortex and place into an ultrasonic bath (VWR Scientific Model 750D) at 60° C. for 15 min at full sonification-power (~360 W).
- Centrifuge for 5 min at 1700×g at room temperature.
- Decant the supernatant to a clean 13×100 mm glass tube.
Fatty Acid Methyl Ester Profile Determination: GC Method:
- Transfer 1000 uL aliquot of the heptane extract into a screw top GC vial National Scientific (C4000-186W)
- Add 100 uL trimethylsulfonium hydroxide in methanol (JenaChem) and cap the vial.
- Shake the vials on an orbital shaker at room temperature for 15 minutes.
- The fatty acid methyl esters were analyzed by directly injecting 1 uL samples (at a 5:1 split ratio) onto an Agilent 7890 gas chromatography system fitted with a Supelco Omegawax 320 (30m×0.320 mm×0.25 um film) capillary column. Hydrogen was used as the carrier gas (39 cm/sec average linear velocity). Inlet and FID detector temperatures were held at 260° C. and the oven column temperature was ramped from 180 to 240° C. at a rate of 12° C. per minute.
- The relative percentages of the individual fatty acid methyl esters were determined using ChemStation.

Fatty Acid Profiling in Homozygous Mega74 and Mega82 Seeds.

Fatty acid compositions of the homozygous Mega74 T3 seeds (FAD2-1A/FAD2-1B knockout) grown in Johnston 2016 field test were analyzed by the GC method described above and the results are shown in Table 8.

TABLE 8

Fatty acid profiles (relative area %) of T3 seeds harvested from field grown Mega74 events, commodity (93Y21) and transgenic high oleic soybean varieties JH89136339 (FAD2 transgene knockout) and P31T96PR (FAD2 transgenic knockout plus 2 FAD3 recessive alleles).

| Description | Name | 16:00 | 16:01 | 17:00 | 17:01 | 18:00 | 18:1 Total | 18:02 | 18:03 |
|---|---|---|---|---|---|---|---|---|---|
| Mega 74 | entry1 | 6.8 | 0.1 | 0.1 | 0.1 | 3.3 | 83.2 | 1.3 | 3.3 |
| Mega 74 | entry2 | 6.9 | 0.1 | 0.1 | 0.1 | 3.6 | 82.7 | 1.6 | 3.3 |
| Mega 74 | entry3 | 6.8 | 0.1 | 0.1 | 0.1 | 3.3 | 82.3 | 2.1 | 3.5 |
| Mega 74 | entry4 | 6.9 | 0.1 | 0.1 | 0.1 | 3.5 | 83.0 | 1.4 | 3.2 |
| Mega 74 | entry5 | 6.8 | 0.1 | 0.1 | 0.1 | 3.5 | 82.6 | 1.5 | 3.4 |
| Mega 74 | entry6 | 6.9 | 0.1 | 0.1 | 0.1 | 3.6 | 82.4 | 1.4 | 3.6 |
| Mega 74 | entry7 | 6.9 | 0.1 | 0.1 | 0.1 | 3.6 | 82.7 | 1.4 | 3.3 |
| Mega 74 | entry8 | 6.8 | 0.1 | 0.1 | 0.1 | 3.6 | 83.1 | 1.3 | 3.2 |
| Mega 74 | entry9 | 6.7 | 0.1 | 0.1 | 0.1 | 3.4 | 83.2 | 1.3 | 3.3 |
| Mega 74 | entry10 | 6.9 | 0.1 | 0.1 | 0.1 | 3.5 | 82.3 | 2.0 | 3.3 |
| Mega 74 | entry11 | 6.9 | 0.1 | 0.1 | 0.1 | 3.5 | 83.2 | 1.3 | 3.1 |
| Mega 74 | entry12 | 6.8 | 0.1 | 0.1 | 0.1 | 3.5 | 83.1 | 1.3 | 3.3 |
| Mega 74 | entry13 | 6.8 | 0.1 | 0.1 | 0.1 | 3.5 | 82.8 | 1.4 | 3.4 |
| Mega 74 | entry14 | 6.9 | 0.1 | 0.1 | 0.1 | 3.4 | 82.8 | 1.4 | 3.3 |
| Mega 74 | entry15 | 6.8 | 0.1 | 0.1 | 0.1 | 3.5 | 83.0 | 1.3 | 3.3 |
| Mega 74 | entry16 | 6.7 | 0.1 | 0.1 | 0.1 | 3.5 | 83.4 | 1.2 | 3.1 |
| Mega 74 | entry17 | 6.8 | 0.1 | 0.1 | 0.1 | 3.6 | 82.8 | 1.4 | 3.4 |
| Mega 74 | entry18 | 6.9 | 0.1 | 0.1 | 0.1 | 3.5 | 83.0 | 1.3 | 3.2 |
| HO parent | JH89136339 | 6.2 | 0.1 | 0.7 | 1.2 | 3.3 | 80.2 | 2.0 | 4.3 |
| Plenish | P31T96PR | 6.0 | 0.1 | 0.7 | 1.1 | 3.6 | 80.6 | 4.3 | 1.7 |
| 93Y21 | 93Y21 | 11.0 | 0.1 | 0.1 | 0.1 | 3.8 | 23.4 | 53.1 | 7.5 |

The relative area percent is representative of a fatty acid weight percent when expressed as a percentage of the total fatty acids by weight. The data show that the knockout of the FAD2-1A and FAD2-1B in soybean delivered a high oleic phenotype. The linolenic acid level is around 3.1-3.6%.

Fatty acid compositions of the homozygous Mega82 T2 seeds (FAD2-1A/FAD2-1B/FAD3a/FAD3b knockout) grown in greenhouse 2016 were analyzed by the GC method described above and the results are shown in Table 9.

TABLE 9

Fatty acid profiles (relative area %) of T2 seeds harvested from Mega82 events in greenhouse, commodity (93Y21) and transgenic high oleic soybean varieties JH89136339 (FAD2 transgene knockout) and P31T96PR (FAD2 transgenic knockout plus 2 FAD3 recessive alleles).

| Description | Name | 16:0 Area | 16:1 Area | 17:0 Area | 17:1 Area | 18:0 Area | 18:1 Area | 18:2 Area | 18:3 Area |
|---|---|---|---|---|---|---|---|---|---|
| Mega 82 | entry1 | 7.6 | 0.1 | 0.1 | 0.1 | 3.9 | 78.1 | 5.8 | 2.1 |
| Mega 82 | entry2 | 7.6 | 0.1 | 0.1 | 0.1 | 3.5 | 80.4 | 4.8 | 1.3 |
| Mega 82 | entry3 | 7.5 | 0.1 | 0.1 | 0.1 | 3.5 | 80.4 | 4.9 | 1.3 |
| Mega 82 | entry4 | 7.3 | 0.1 | 0.1 | 0.1 | 3.5 | 80.9 | 4.2 | 1.6 |
| Mega 82 | entry5 | 7.5 | 0.1 | 0.1 | 0.1 | 3.6 | 80.5 | 4.3 | 1.6 |
| Mega 82 | entry6 | 7.3 | 0.1 | 0.1 | 0.1 | 3.7 | 80.7 | 4.1 | 1.6 |
| Mega 82 | entry7 | 7.6 | 0.1 | 0.1 | 0.1 | 3.8 | 78.6 | 5.9 | 1.7 |
| Mega 82 | entry8 | 7.3 | 0.1 | 0.1 | 0.1 | 3.7 | 79.8 | 5.1 | 1.7 |
| Mega 82 | entry9 | 7.4 | 0.1 | 0.1 | 0.1 | 4.1 | 77.6 | 6.3 | 2.1 |
| Mega 82 | entry10 | 7.5 | 0.1 | 0.1 | 0.1 | 3.8 | 80.1 | 4.7 | 1.5 |
| Mega 82 | entry11 | 7.4 | 0.1 | 0.1 | 0.1 | 4.1 | 78.5 | 5.7 | 1.8 |
| Mega 82 | entry12 | 7.6 | 0.1 | 0.1 | 0.1 | 3.7 | 78.3 | 5.8 | 1.9 |
| Mega 82 | entry13 | 7.7 | 0.1 | 0.1 | 0.1 | 3.5 | 80.4 | 4.4 | 1.6 |
| Mega 82 | entry14 | 8.0 | 0.1 | 0.1 | 0.1 | 3.3 | 80.0 | 4.8 | 1.6 |
| Mega 82 | entry15 | 7.7 | 0.1 | 0.1 | 0.1 | 3.3 | 81.3 | 3.6 | 1.6 |
| Mega 82 | entry16 | 7.6 | 0.1 | 0.1 | 0.1 | 3.5 | 79.4 | 5.4 | 1.7 |
| Mega 82 | entry17 | 7.6 | 0.1 | 0.1 | 0.1 | 3.6 | 80.2 | 4.5 | 1.6 |
| Mega 82 | entry18 | 7.7 | 0.1 | 0.1 | 0.1 | 3.5 | 80.9 | 3.8 | 1.6 |

TABLE 9-continued

Fatty acid profiles (relative area %) of T2 seeds harvested from Mega82 events in greenhouse, commodity (93Y21) and transgenic high oleic soybean varieties JH89136339 (FAD2 transgene knockout) and P31T96PR (FAD2 transgenic knockout plus 2 FAD3 recessive alleles).

| Description | Name | 16:0 Area | 16:1 Area | 17:0 Area | 17:1 Area | 18:0 Area | 18:1 Area | 18:2 Area | 18:3 Area |
|---|---|---|---|---|---|---|---|---|---|
| HO parent | JH89136339 | 6.2 | 0.1 | 0.7 | 1.2 | 3.3 | 80.2 | 2.0 | 4.3 |
| Plenish | P31T96PR | 6.0 | 0.1 | 0.7 | 1.1 | 3.6 | 80.6 | 4.3 | 1.7 |
| 93Y21 | 93Y21 | 11.0 | 0.1 | 0.1 | 0.1 | 3.8 | 23.4 | 53.1 | 7.5 |

The relative area percent is representative of a fatty acid weight percent when expressed as a percentage of the total fatty acids by weight. The data show that the knockout of the FAD2-1A, FAD2-1B, FAD3a and Fad3b genes in soybean delivered both the high oleic and linolenic phenotype.

Fatty Acid Profiling in Non-Target Tissues.

Homozygous Mega74, Mega82 events, commodity (93Y21 and 93B86) and transgenic high oleic soybean varieties 93M02P (FAD2 transgene knockout) and P34T90PR (FAD2 transgenic knockout plus 2 FAD3 recessive alleles) were grown in short rows in the field in Johnston Iowa during the 2017 growing season. Forty-two days after flowering, when the plants were at the R5 stage, individual plants were pulled from within the test rows. Leaf, stem and washed root material were harvested, flash frozen in liquid nitrogen and transported back to the laboratory where they were stored at −80° C. until further processing.

The tissue was ground to a fine powder in a mortar and pestle in the presence of liquid nitrogen. Twenty mg aliquots of the powders were transferred to 13×100 mm test tubes and 2 ml of freshly prepared 5% concentrated sulfuric acid in anhydrous methanol was added to each. The threads on the tubes were wrapped with Teflon® pipe tape and sealed with a Teflon® lined cap. Samples were vortex mixed and heated for 1 h at 80° C. The samples were allowed to cool to room temperature and 1 ml of 1M aqueous sodium chloride was added to each tube followed by 500 ul of heptane. The tubes were vortexed and allowed to stand. Once the phases had separated, 200 ul of the upper heptane phase was transferred to a GC-vial fitted with a volume reducing liner. The samples were then subjected to fatty acid methyl ester analysis, as described above, using 2 ul injections.

TABLE 10

Fatty acid profiles (relative area %) of non-target tissue harvested from field grown Mega74, Mega82 events, commodity (93Y21 and 93B86) and transgenic high oleic soybean varieties 93M02P (FAD2 transgene knockout) and P34T90PR (FAD2 transgenic knockout plus 2 FAD3 recessive alleles).

| Material | Name | 16:0 Area | 16:1 Area | 17:0 Area | 17:1 Area | 18:0 Area | Total 18:1 | 18:2 Area | 18:3 Area |
|---|---|---|---|---|---|---|---|---|---|
| 42 DAF leaf | P34T90PR | 12.4 | 0.2 | 0.2 | 0.1 | 3.8 | 0.9 | 8.6 | 73.8 |
| 42 DAF leaf | 93B86 | 11.2 | 0.3 | 0.1 | 0.2 | 3.5 | 2.0 | 12.5 | 70.3 |
| 42 DAF leaf | 93Y21 | 11.3 | 0.3 | 0.2 | 0.2 | 3.1 | 2.1 | 11.3 | 71.4 |
| 42 DAF leaf | 93M02P | 11.4 | 0.2 | 0.1 | 0.1 | 3.6 | 1.9 | 13.2 | 69.5 |
| 42 DAF leaf | Mega74 event 6.1 | 11.8 | 0.3 | 0.2 | 0.2 | 3.2 | 1.8 | 9.8 | 72.8 |
| 42 DAF leaf | Mega82 event 3.1 | 11.0 | 0.3 | 0.2 | 0.2 | 3.2 | 1.5 | 8.6 | 75.1 |
| 42 DAF leaf | Mega82 event 5.3 | 12.2 | 0.3 | 0.2 | 0.2 | 3.3 | 2.1 | 13.0 | 68.7 |
| 42 DAF root | P34T90PR | 19.2 | 0.7 | 0.7 | 0.2 | 3.6 | 4.6 | 51.0 | 20.1 |
| 42 DAF root | 93B86 | 18.1 | 0.2 | 0.4 | 0.1 | 2.9 | 3.3 | 43.7 | 31.2 |
| 42 DAF root | 93Y21 | 16.7 | 0.2 | 0.5 | 0.2 | 3.0 | 2.6 | 42.9 | 34.0 |
| 42 DAF root | 93M02P | 17.4 | 0.4 | 0.5 | 0.1 | 2.9 | 2.4 | 40.6 | 35.7 |
| 42 DAF root | Mega74 event 6.1 | 18.0 | 0.2 | 0.5 | 0.1 | 3.7 | 2.7 | 44.1 | 30.8 |
| 42 DAF root | Mega82 event 3.1 | 17.3 | 0.2 | 0.5 | 0.2 | 3.6 | 2.4 | 53.0 | 22.8 |
| 42 DAF root | Mega82 event 5.3 | 17.1 | 0.4 | 0.5 | 0.2 | 3.0 | 2.3 | 51.6 | 25.0 |
| 42 DAF stem | 93B86 | 16.2 | 0.2 | 0.3 | 0.0 | 3.9 | 3.1 | 33.5 | 42.8 |
| 42 DAF stem | 93Y21 | 16.0 | 0.2 | 0.3 | 0.0 | 3.9 | 3.2 | 33.1 | 43.2 |
| 42 DAF stem | 93M02P | 16.5 | 0.1 | 0.3 | 0.0 | 3.7 | 2.3 | 31.7 | 45.3 |
| 42 DAF stem | Mega74 event 6.1 | 16.0 | 0.3 | 0.3 | 0.0 | 3.8 | 3.4 | 32.9 | 43.3 |
| 42 DAF stem | Mega82 event 3.1 | 16.5 | 0.3 | 0.4 | 0.0 | 5.1 | 1.7 | 33.4 | 42.7 |
| 42 DAF stem | Mega82 event 5.3 | 15.1 | 0.2 | 0.3 | 0.0 | 4.2 | 2.5 | 36.5 | 41.1 |

The relative area percent is representative of a fatty acid weight percent when expressed as a percentage of the total fatty acids by weight. The data show that the off-target (non-seed) tissues in the Mega74 and Mega82 events had very low levels of oleic acid, which were indistinguishable from those in the comparable tissues harvested from the control tissues varieties. Subtle differences in the linoleic (18:2) and linolenic (18:3) acid contents of the root tissues were apparent. The Mega82 materials, which carry FAD3a and FAD3b knockouts, had higher linoleic and lower linolenic acid contents than Mega74, the commodity soy varieties (93B86 and 93Y21) and the transgenic FAD2 knockout variety 93M02P. High oleic variety P34T90PR, which carries two recessive FAD3 alleles in addition to a transgenic knockout of the FAD2 alleles, had a similar fatty acid profile the two Mega82 events.

Example 6

Agronomic Evaluation of CRISPR-Edited High-Oleic Low-Linolenic Variants

Seeds of the three soybean variants 3.1, 5.3 and 1.5a (each containing the FAD2-1A, FAD2-1B, FAD3a and FAD3b mutation edits shown in FIG. 2 which were generated simultaneously in each variant using two guide RNAs) were grown in the field at three varied locations in the United States alongside a 93Y21 elite soybean control to assess agronomic performance of the variants. Emergence, plant height, maturity and yield were measured and averaged across the locations. No measurable difference could be detected between the variants and the control for emergence, plant height, maturity and yield. Protein and oil was also measured in seeds harvested from the plants grown in the three varied locations. Seeds of the three variants 3.1, 5.3 and 1.5a were found to have comparable oil and protein content on a seed dry weight basis as the control 93Y21 seeds and control seeds having a FAD2 transgenic knockout plus 2 FAD3 recessive alleles.

Example 7

Detection of Site-Specific Mutations with NHEJ Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, Calif.) with target site-specific primers and a FAM-labeled fluorescence probe to check copy number changes of the target sites. The qPCR analysis was done in duplex reactions with a syringolide induced protein (SIP) gene as the endogenous control and a wild type 93Y21 genomic DNA sample that contains one copy of the target site with 2 alleles, as the single copy calibrator. The endogenous control probe SIP-T was labeled with VIC (2'-chloro-7'phenyl-1,4-dichloro-6-carboxy-fluorescein) and the gene-specific probes FAD2-T1, FAD2-T2 and FAD3-T2 were labeled with FAM (Fluorescein) (Table 11) for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

TABLE 11

Primers/probes used in qPCR analyses of transgenic soybean events.

| Target Site | Primer/Probe Name | Sequences | SEQ ID NOs: |
| --- | --- | --- | --- |
| FAD2-1A | FAD2-F1 | TCGTGTGGCCAAAGTGGAA | 11 |
| | FAD2-R1 | TTTGTGTTTGGAACCCTTGAGA | 12 |
| | FAD2-T1 (FAM-MGB) | TTCAAGGGAAGAAGCC | 13 |
| FAD2-1B | FAD2-F2 | CCGTGTGGCCAAAGTTGAA | 14 |
| | FAD2-R1 | TTTGTGTTTGGAACCCTTGAGA | 12 |
| | FAD2-T2 (FAM-MGB) | TTCAGCAGAAGAAGCC | 15 |
| FAD3a | FAD3-F1 | TAATGGATACCAAAAGGAAGC | 16 |
| | FAD3-R2 | CAAGCACATCCCTGAGAACATAAC | 17 |
| | FAD3-T2 (FAM-MGB) | AATCCATGGAGATCCCT | 18 |
| FAD3b | FAD3-F2 | ATACCAACAAAAGGGTTCTTC | 19 |
| | FAD3-R2 | CAAGCACATCCCTGAGAACATAAC | 17 |
| | FAD3-T2 (FAM-MGB) | AATCCATGGAGATCCCT | 18 |
| SIP | SIP-130F | TTCAAGTTGGGCTTTTTCAGAAG | 80 |
| | SIP-198R | TCTCCTTGGTGCTCTCATCACA | 81 |
| | SIP-170T (VIC-MGB) | CTGCAGCAGAACCAA | 82 |

Since the wild type 93Y21 genomic DNA with two alleles of the target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1).

In total, four soybean transformation experiments were carried out. In RV019927 and RV019929, the gRNA cassettes were near the right border and placed upstream of the Cas9 expression cassettes in the binary vectors. In contrast, in RV019928 and RV019930, the gRNA expression cassettes were near the left border and placed downstream of the Cas9 expression cassettes in the binary vectors. As shown in Table 12, Table 13, for the two experiments to knockout only the two FAD2-1 genes, the gRNA near the right border and placed upstream of Cas9 configuration design provided much higher gene knockout efficiency as compared to the design with the gRNA near the left border and placed downstream of Cas9. For example, the bi-allelic (NHEJ-Null) knockout efficiency reached 63% for the FAD2-1A gene and 56% for the FAD2-1B gene (Table 12) with the RV019927 vector. The bi-allelic (NHEJ-Null) knockout efficiency was only 7% for the FAD2-1 gene and 10% for the FAD2-1B gene (Table 13) with the RV019928 vector. The WT population only made up about 2-3% in the experiment with the RV019927 vector, as compared to 37-44% in the experiment with the RV019928 vector.

In the third and fourth experiments, either the RV019929 or RV019930 binary vectors was used to knockout the two FAD2-1 genes and the two FAD3 genes. As shown in Table 12, Table 13, these two experiments also demonstrated that RV019929 vector design, with the gRNA expression cassette near the right border and upstream of the Cas9 expression cassette, provided much higher quadra gene knockout efficiency as compared to the RV019930 binary vector in the FAD2-1A, FAD2-1B, FAD3a and FAD3b genes. These unexpected results demonstrated the different gRNA/Cas9 expression cassette configurations in the binary vectors had dramatic effects on the target gene editing efficiency. Vectors with gRNA cassettes near the right border and placed upstream of the Cas9 expression cassettes increased the efficiency of editing the target site.

TABLE 12

FAD2-1 Target Site Mutations Induced by the Guide RNA/Cas9 system in 93Y21 with RV019927. Numbers indicate no. of events (numbers in parentheses are %).

| Target site | Total events | Wt-Homo (%) | NHEJ-Hemi (%) | NHEJ-Null (%) |
|---|---|---|---|---|
| FAD2-1A | 106 | 2 (2%) | 37 (35%) | 67 (63%) |
| FAD2-1B |  | 3 (3%) | 44 (42%) | 59 (56%) |

TABLE 13

FAD2-1 Target Site Mutations Induced by the Guide RNA/Cas9 system in 93Y21 with RV019928. Numbers indicate no. of events (numbers in parentheses are %).

| Target site | Total event | Wt-Homo (%) | NHEJ-Hemi (%) | NHEJ-Null (%) |
|---|---|---|---|---|
| FAD2-1A | 41 | 15 (37%) | 23 (56%) | 3 (7%) |
| FAD2-1B |  | 18 (44%) | 19 (46%) | 4 (10%) |

TABLE 14

FAD2-1 and FAD3 Target Site Mutations Induced by the Guide RNA/Cas9 system in 93Y21 with RV019929. Numbers indicate no. of events (numbers in parentheses are % of the total analyzed events).

| Target Site | Total event | Wt-Homo (%) | NHEJ-Hemi (%) | NHEJ-Null (%) |
|---|---|---|---|---|
| FAD2-1A | 27 | 0 (0%) | 11 (41%) | 16 (59%) |
| FAD2-1B |  | 1 (4%) | 12 (44%) | 14 (52%) |
| FAD3a |  | 1 (4%) | 6 (22%) | 20 (74%) |
| FAD3b |  | 1 (4%) | 4 (15%) | 22 (81%) |

TABLE 15

FAD2-1 and FAD3 Target Site Mutations Induced by the Guide RNA/Cas9 system in 93Y21 with RV019930. Numbers indicate no. of events (numbers in parentheses are % of the total analyzed events).

| Target Site | Total event | Wt-Homo (%) | NHEJ-Hemi (%) | NHEJ-Null (%) |
|---|---|---|---|---|
| FAD2-1A | 42 | 20 (48%) | 17 (40%) | 5 (12%) |
| FAD2-1B |  | 7 (17%) | 32 (76%) | 3 (7%) |
| FAD3a |  | 7 (17%) | 32 (76%) | 3 (7%) |
| FAD3b |  | 12 (29%) | 22 (52%) | 8 (19%) |

The target regions of NHEJ-Null events were amplified by regular PCR from the same genomic DNA samples using primers specific respectively to FAD2-1A, FAD2-1B, FAD3a and FAD3b genes (Table 8).

TABLE 8

PCR primers for the gRNA targets of the FAD2-1 and FAD3 genes

| Target Site | Primer1 | SEQ ID NO: | Primer2 | SEQ ID NO: |
|---|---|---|---|---|
| FAD2-1A | WOL1007 | 23 | WOL1009 | 25 |
| FAD2-1B | WOL1008 | 24 | WOL1009 | 25 |

TABLE 8-continued

PCR primers for the gRNA targets of the FAD2-1 and FAD3 genes

| Target Site | Primer1 | SEQ ID NO: | Primer2 | SEQ ID NO: |
|---|---|---|---|---|
| FAD3a | WOL1100 | 26 | WOL1101 | 27 |
| FAD3b | WOL1102 | 28 | WOL1103 | 29 |

The PCR bands were cloned into pCR2.1 vector using a TOPO-TA cloning kit (Invitrogen) and multiple clones were sequenced to check for target site sequence changes as the results of NHEJ. Various small deletions near the Cas9 cleavage site, 3 bp upstream of the PAM, were revealed at all four tested target sites, with most of them resulting in frame-shift knockouts (FIG. 3A-FIG. 3B, FIG. 4A-FIG. 4B, FIG. 5A-FIG. 5B). These sequence analyses confirmed the occurrence of NHEJ mediated by the guide RNA/Cas9 system at the specific Cas9 target sites.

The foregoing invention has been described in detail by way of illustration and example for purposes of clarity and understanding. As is readily apparent to one skilled in the art, the foregoing disclosures are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

All publications, patents, and patent applications mentioned in the specification are incorporated by reference herein in their entireties for the purpose cited to the same extent as if each was specifically and individually indicated to be incorporated by reference herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present).

What is claimed is:

1. A method of altering the fatty add profile in the seed of a soybean plant, the method comprising introducing four or more nucleotide modifications through four or more targeted DNA breaks at four or more genomic loci of a plant at the same time, wherein
   (a) the genomic loci comprise a first polynucleotide encoding a FAD2-1A polypeptide, a second polynucleotide encoding a FAD3a polypeptide, a third polynucleotide encoding a FAD2-1 B polypeptide, and a fourth polynucleotide encoding a FAD3b polypeptide, and
   (b) wherein the oleic acid content is increased to at least 75% by weight of the total fatty acids and the linolenic acid content is decreased to less than 3% by weight of the total fatty acids in the seed compared to the seed of a control plant not comprising the four or more introduced nucleotide modifications.

2. The method of claim 1, wherein the nucleotide modifications are introduced by targeted DNA breaks using no more than two guide RNAs.

3. The method of claim 1, wherein the soybean plant has a similar yield as the control plant.

4. The method of claim 1, wherein the modifications target the genomic locus at a target site such that more than one genetic modifications at different sites are present within (a) the same coding region; (b) non-coding region; (c) regulatory sequence; or (d) untranslated region of an endogenous polynucleotide encoding a polypeptide that is involved in fatty acid metabolism.

5. The method of claim 1, wherein the target site comprises SEQ ID NO: 6 or SEQ ID NO: 7.

6. The method of claim 1, wherein the first polynucleotide comprises at least one of SEQ ID NOS: 35-43 wherein the second polynucleotide comprises at least one of SEQ ID NOS: 59-61, wherein the third polynucleotide comprises at least one of SEQ ID NOS: 44-58, and wherein the fourth polynucleotide comprises at least one of SEQ ID NOS: 62-64.

7. The method of claim 1, wherein the first polynucleotide encodes a FAD2-1A polypeptide having at least 90% identity to SEQ ID NO: 70, the second polynucleotide encodes a FAD3a polypeptide haying at least 90% identity to SEQ ID NO: 74, and wherein the genomic loci comprise a third polynucleotide encoding a FAD2-1 B polypeptide having at least 90% identity to SEQ ID NO: 72 and a fourth polynucleotide encoding a FAD3b polypeptide having at least 90% identity to SEQ ID NO: 76.

8. The method of claim 7, wherein the first polynucleotide comprises SEQ ID NO: 54, the second polynucleotide comprises SEQ ID NO: 60, the third polynucleotide comprises SEQ ID NO: 57, and the fourth polynucleotide comprises SEQ ID NO: 63.

9. The method of claim 7, wherein the first polynucleotide comprises SEQ ID NO: 55, the second polynucleotide comprises SEQ ID NO: 61, the third polynucleotide comprises SEQ ID NO: 58, and the fourth polynucleotide comprises SEQ ID NO: 64.

10. The method of claim 1, wherein the genomic loci comprise an edit in a polynucleotide that encodes a FAD3 polypeptide comprising an amino acid sequence that is at least 90% identical to a sequence selected from the group consisting of SEQ ID NOS: 74 or 76 such that the edit results in one or more of the following:
   (a) reduced expression of a polynucleotide encoding the FAD3 polypeptide;
   (b) reduced activity of the FAD3 polypeptide;
   (c) generation of one or more alternative spliced transcripts of a polynucleotide encoding the FAD3 polypeptide;
   (d) deletion of one or more active sites of the FAD3 polypeptide;
   (e) frameshift mutation in one or more exons of a polynucleotide encoding the FAD3 polypeptide;
   (f) deletion of a substantial portion of the polynucleotide encoding the FAD3 polypeptide or deletion of the polynucleotide encoding the full-length FAD3 polypeptide;
   (g) repression of an enhancer motif present within a regulatory region encoding the FAD3 polypeptide; and
   (h) modification of one or more nucleotides or deletion of a regulatory element operably linked to the expression of the polynucleotide encoding the FAD3 polypeptide, wherein the regulatory element is present within a promoter, intron, 3'UTR, terminator or a combination thereof.

11. The method of claim 1, wherein the genomic loci comprise an edit in a polynucleotide that encodes a FAD2-1 polypeptide comprising an amino acid sequence that is at least 90% identical to a sequence selected from the group consisting of SEQ ID NOS: 70 or 72 such that the edit results in one or more of the following:
   (a) reduced expression of a polynucleotide encoding the FAD2-1 polypeptide;
   (b) reduced activity of the FAD2-1 polypeptide;
   (c) generation of one or more alternative spliced transcripts of a polynucleotide encoding the FAD2-1 polypeptide;
   (d) deletion of one or more domains of the Br2 polypeptide;
   (e) frameshift mutation in one or more exons of a polynucleotide encoding the FAD2-1 polypeptide;
   (f) deletion of a substantial portion of the polynucleotide encoding the FAD2-1 polypeptide or deletion of the polynucleotide encoding the FAD2-1 polypeptide;
   (g) repression of an enhancer motif present within a regulatory region encoding the FAD2-1 polypeptide;
   (h) modification of one or more nucleotides or deletion of a regulatory element operably linked to the expression of the polynucleotide encoding the FAD2-1 polypeptide, wherein the regulatory element is present within a promoter, intron, 3'UTR, terminator or a combination thereof.

12. The method of claim 1, wherein the targeted DNA break is not effected using a TALEN (transcription activator-like effector nuclease).

* * * * *